United States Patent
Wang

(10) Patent No.: US 11,977,057 B2
(45) Date of Patent: May 7, 2024

(54) METHOD AND SYSTEM FOR NEOANTIGEN ANALYSIS

(71) Applicant: Complete Omics Inc., Baltimore, MD (US)

(72) Inventor: Qing Wang, Owings Mills, MD (US)

(73) Assignee: COMPLETE OMICS INTERNATIONAL INC., Baltimore, MD (US)

(*) Notice: Subject to any disclaimer, the term of this patent is extended or adjusted under 35 U.S.C. 154(b) by 66 days.

(21) Appl. No.: 17/346,282

(22) Filed: Jun. 13, 2021

(65) Prior Publication Data

US 2021/0389280 A1 Dec. 16, 2021

Related U.S. Application Data

(60) Provisional application No. 63/038,816, filed on Jun. 13, 2020.

(51) Int. Cl.
*G01N 30/06* (2006.01)
*G01N 1/28* (2006.01)
(Continued)

(52) U.S. Cl.
CPC ............ *G01N 30/06* (2013.01); *G01N 1/286* (2013.01); *G01N 1/34* (2013.01); *G01N 1/405* (2013.01);
(Continued)

(58) Field of Classification Search
CPC .......... G01N 30/06; G01N 1/286; G01N 1/34; G01N 1/405; G01N 30/7233; G01N 30/88;
(Continued)

(56) References Cited

U.S. PATENT DOCUMENTS

| | | | | |
|---|---|---|---|---|
| 2002/0098595 A1* | 7/2002 | Lubman | ............... | C07K 1/36 436/178 |
| 2004/0229283 A1* | 11/2004 | Gygi | ............... | G01N 33/6842 435/7.1 |

(Continued)

FOREIGN PATENT DOCUMENTS

| | | | | |
|---|---|---|---|---|
| WO | WO-2004031730 A2 * | 4/2004 | ....... | G01N 33/54306 |
| WO | WO 2010/117817 A2 | 10/2010 | | |
| WO | WO-2017173321 A1 * | 10/2017 | ......... | A61K 39/0011 |

OTHER PUBLICATIONS

Covaris, "Automated cryoPREP System User Manual," Aug. 2018, Covaris Inc., Accessed via Web Jan. 20, 2023, <https://www.covaris.com/wp/wp-content/uploads/resources_pdf/pn_010035.pdf>. (Year: 2018).*

(Continued)

*Primary Examiner* — Jill A Warden
*Assistant Examiner* — Michael Paul Shimek
(74) *Attorney, Agent, or Firm* — K&L Gates LLP

(57) ABSTRACT

A method for characterizing a target peptide through a detection approach such as mass spectrometry is provided, including: introducing at least one guard molecule to mix with the target peptide; and applying the detection approach for the characterization of the target peptide. Each guard molecule is configured to have similar characteristics as the target peptide, yet is still distinguishable therefrom by the detection approach, such as having a mass spectrometry-distinguishable different M/z value compared with the target peptide. The method can be used to characterize a neoantigen peptide through mass spectrometry, upstream of which the method can further include steps for tissue sample preparation, HLA molecules enrichment, elution, clean-up, and purification. Some or all of these steps can be configured to be executed in a substantially automatic manner with little (Continued)

or no manual intervention. A system for implementing the neoantigen analysis method is further provided.

15 Claims, 10 Drawing Sheets

Specification includes a Sequence Listing.

(51) Int. Cl.
  *G01N 1/34* (2006.01)
  *G01N 1/40* (2006.01)
  *G01N 30/72* (2006.01)
  *G01N 30/88* (2006.01)
  *G01N 33/68* (2006.01)

(52) U.S. Cl.
  CPC ......... *G01N 30/7233* (2013.01); *G01N 30/88* (2013.01); *G01N 33/6848* (2013.01); *G01N 2001/2866* (2013.01); *G01N 2030/8804* (2013.01); *G01N 2030/8831* (2013.01); *G01N 2333/70539* (2013.01)

(58) Field of Classification Search
  CPC ....... G01N 33/6848; G01N 2001/2866; G01N 2030/8804; G01N 2030/8831; G01N 2333/70539; G01N 2001/4083; G01N 1/4077; G01N 1/42
  See application file for complete search history.

(56) References Cited

U.S. PATENT DOCUMENTS

| | | |
|---|---|---|
| 2012/0070844 A1* | 3/2012 | Rodriguez Cutillas ..................... G01N 33/6848 435/7.1 |
| 2014/0187577 A1* | 7/2014 | Funahashi ........ G01N 33/57407 435/7.92 |
| 2019/0346442 A1 | 11/2019 | Carr et al. |

OTHER PUBLICATIONS

International Preliminary Report and Written Opinion for PCT/US2021/37141 dated Oct. 20, 2021 7 pages.
Abelin, "Defining HLA-II Ligand Processing and Binding Rules with Mass Spectrometry Enhances Cancer Epitope Prediction," Immunity 51, Oct. 15, 2019, 34 pages.
Vincelli, "Comparison of Tissue-Disruption Methods for PCR-Based Detection of Plant Pathogens," Plant Disease, vol. 97, No. 3, Mar. 2013, pp. 363-368.
Wang, "Direct Detection and Qualification of Neoantigens," Cancer Immunology Research, vol. 7, Ussue 11, Nov. 1, 2019, pp. 1748-1754.
Zhang, "Recent advances in absolute quantification of peptides and proteins using LC-MS," Reviews in Analytical Chemistry, vol. 33, Issue 1, 2014, p. 31-47.
Lamb, et al., "A practical approach" Gene Probes, Apr. 4, 1995, abstract 1 page.
Office Action for EP18781045.2, Oct. 17, 2023m 5 pages.

* cited by examiner

Step1. Enrichment of HLA molecules with repeated loading

Step2. Elution of HLA molecules and loading trap column

Step3. Flushing the trap column to remove large HLA molecules

Step4. Eluting neoantigens from trap column and loading to SEC column

Step5. Flushing through SEC column to further purify neoantigens

| Sample ID | Cancer type | Cancer Driver Gene | Mutation | 12-AA neoantigen reference sequence | 11-AA neoantigen reference sequence | 10-AA neoantigen reference sequence | 9-AA neoantigen reference sequence | 8-AA neoantigen reference sequence |
|---|---|---|---|---|---|---|---|---|
| 1 | Human Large Intestine Adenocarcinoma | K-Ras | Q61H | TCLLDILDTAGHEEYSAMRDQYM (SEQ ID NO. 1) | CLLDILDTAGHEEYSAMRDQY (SEQ ID NO. 118) | LLDILDTAGHEEYSAMRDQ (SEQ ID NO. 226) | LDILDTAGHEEYSAMRD (SEQ ID NO. 325) | DILDTAGHEEYSAMR (SEQ ID NO. 415) |
|  |  |  |  | TCLLDILDTAGH (SEQ ID NO. 2) | CLLDILDTAGH (SEQ ID NO. 119) | LLDILDTAGH (SEQ ID NO. 227) | LDILDTAGH (SEQ ID NO. 326) | DILDTAGH (SEQ ID NO. 416) |
|  |  |  |  | CLLDILDTAGHE (SEQ ID NO. 3) | LLDILDTAGHE (SEQ ID NO. 120) | LDILDTAGHE (SEQ ID NO. 228) | DILDTAGHE (SEQ ID NO. 327) | ILDTAGHE (SEQ ID NO. 417) |
|  |  |  |  | LLDILDTAGHEE (SEQ ID NO. 4) | LDILDTAGHEE (SEQ ID NO. 121) | DILDTAGHEE (SEQ ID NO. 229) | ILDTAGHEE (SEQ ID NO. 328) | LDTAGHEE (SEQ ID NO. 418) |
|  |  |  |  | LDILDTAGHEEY (SEQ ID NO. 5) | DILDTAGHEEY (SEQ ID NO. 122) | ILDTAGHEEY (SEQ ID NO. 230) | LDTAGHEEY (SEQ ID NO. 329) | DTAGHEEY (SEQ ID NO. 419) |
|  |  |  |  | DILDTAGHEEYS (SEQ ID NO. 6) | ILDTAGHEEYS (SEQ ID NO. 123) | LDTAGHEEYS (SEQ ID NO. 231) | DTAGHEEYS (SEQ ID NO. 330) | TAGHEEYS (SEQ ID NO. 420) |
|  |  |  |  | ILDTAGHEEYSA (SEQ ID NO. 7) | LDTAGHEEYSA (SEQ ID NO. 124) | DTAGHEEYSA (SEQ ID NO. 232) | TAGHEEYSA (SEQ ID NO. 331) | AGHEEYSA (SEQ ID NO. 421) |
|  |  |  |  | LDTAGHEEYSAM (SEQ ID NO. 8) | DTAGHEEYSAM (SEQ ID NO. 125) | TAGHEEYSAM (SEQ ID NO. 233) | AGHEEYSAM (SEQ ID NO. 332) | GHEEYSAM (SEQ ID NO. 422) |
|  |  |  |  | DTAGHEEYSAMR (SEQ ID NO. 9) | TAGHEEYSAMR (SEQ ID NO. 126) | AGHEEYSAMR (SEQ ID NO. 234) | GHEEYSAMR (SEQ ID NO. 333) | HEEYSAMR (SEQ ID NO. 423) |
|  |  |  |  | TAGHEEYSAMRD (SEQ ID NO. 10) | AGHEEYSAMRD (SEQ ID NO. 127) | GHEEYSAMRD (SEQ ID NO. 235) | HEEYSAMRD (SEQ ID NO. 334) |  |
|  |  |  |  | AGHEEYSAMRDQ (SEQ ID NO. 11) | GHEEYSAMRDQ (SEQ ID NO. 128) | HEEYSAMRDQ (SEQ ID NO. 236) |  |  |
|  |  |  |  | GHEEYSAMRDQY (SEQ ID NO. 12) | HEEYSAMRDQY (SEQ ID NO. 129) |  |  |  |
|  |  |  |  | HEEYSAMRDQYM (SEQ ID NO. 13) |  |  |  |  |
| 2 | Human Large Intestine Adenocarcinoma | K-Ras | Q61L | TCLLDILDTAGLEEYSAMRDQYM (SEQ ID NO. 14) | CLLDILDTAGLEEYSAMRDQY (SEQ ID NO. 130) | LLDILDTAGLEEYSAMRDQ (SEQ ID NO. 237) | LDILDTAGLEEYSAMRD (SEQ ID NO. 335) | DILDTAGLEEYSAMR (SEQ ID NO. 424) |
|  |  |  |  | TCLLDILDTAGL (SEQ ID NO. 15) | CLLDILDTAGL (SEQ ID NO. 131) | LLDILDTAGL (SEQ ID NO. 238) | LDILDTAGL (SEQ ID NO. 336) | DILDTAGL (SEQ ID NO. 425) |
|  |  |  |  | CLLDILDTAGLE (SEQ ID NO. 16) | LLDILDTAGLE (SEQ ID NO. 132) | LDILDTAGLE (SEQ ID NO. 239) | DILDTAGLE (SEQ ID NO. 337) | ILDTAGLE (SEQ ID NO. 426) |
|  |  |  |  | LLDILDTAGLEE (SEQ ID NO. 17) | LDILDTAGLEE (SEQ ID NO. 133) | DILDTAGLEE (SEQ ID NO. 240) | ILDTAGLEE (SEQ ID NO. 338) | LDTAGLEE (SEQ ID NO. 427) |
|  |  |  |  | LDILDTAGLEEY (SEQ ID NO. 18) | DILDTAGLEEY (SEQ ID NO. 134) | ILDTAGLEEY (SEQ ID NO. 241) | LDTAGLEEY (SEQ ID NO. 339) | DTAGLEEY (SEQ ID NO. 428) |
|  |  |  |  | DILDTAGLEEYS (SEQ ID NO. 19) | ILDTAGLEEYS (SEQ ID NO. 135) | LDTAGLEEYS (SEQ ID NO. 242) | DTAGLEEYS (SEQ ID NO. 340) | TAGLEEYS (SEQ ID NO. 429) |
|  |  |  |  | ILDTAGLEEYSA (SEQ ID NO. 20) | LDTAGLEEYSA (SEQ ID NO. 136) | DTAGLEEYSA (SEQ ID NO. 243) | TAGLEEYSA (SEQ ID NO. 341) | AGLEEYSA (SEQ ID NO. 430) |
|  |  |  |  | LDTAGLEEYSAM (SEQ ID NO. 21) | DTAGLEEYSAM (SEQ ID NO. 137) | TAGLEEYSAM (SEQ ID NO. 244) | AGLEEYSAM (SEQ ID NO. 342) | GLEEYSAM (SEQ ID NO. 431) |

FIG. 3A

| | | | | | | | |
|---|---|---|---|---|---|---|---|
| | | | | DTAGLEEYSAMR (SEQ ID NO. 22) | TAGLEEYSAMR (SEQ ID NO. 138) | AGLEEYSAMR (SEQ ID NO. 245) | GLEEYSAMR (SEQ ID NO. 343) | LEEYSAMR (SEQ ID NO. 432) |
| | | | | TAGLEEYSAMRD (SEQ ID NO. 23) | AGLEEYSAMRD (SEQ ID NO. 139) | GLEEYSAMRD (SEQ ID NO. 246) | LEEYSAMRD (SEQ ID NO. 344) | |
| | | | | AGLEEYSAMRDQ (SEQ ID NO. 24) | GLEEYSAMRDQ (SEQ ID NO. 140) | LEEYSAMRDQ (SEQ ID NO. 247) | | |
| | | | | GLEEYSAMRDQY (SEQ ID NO. 25) | LEEYSAMRDQY (SEQ ID NO. 141) | | | |
| | | | | LEEYSAMRDQYM (SEQ ID NO. 26) | | | | |
| 3 | Human Large Intestine Adenocarcinoma | K-Ras | Q61R | TCLLDILDTAGREEYSAMRDQYM (SEQ ID NO. 27) | CLLDILDTAGREEYSAMRDQY (SEQ ID NO. 142) | LLDILDTAGREEYSAMRDQ (SEQ ID NO. 248) | LDILDTAGREEYSAMRD (SEQ ID NO. 345) | DILDTAGREEYSAMR (SEQ ID NO. 433) |
| | | | | TCLLDILDTAGR (SEQ ID NO. 28) | CLLDILDTAGR (SEQ ID NO. 143) | LLDILDTAGR (SEQ ID NO. 249) | LDILDTAGR (SEQ ID NO. 346) | DILDTAGR (SEQ ID NO. 434) |
| | | | | CLLDILDTAGRE (SEQ ID NO. 29) | LLDILDTAGRE (SEQ ID NO. 144) | LDILDTAGRE (SEQ ID NO. 250) | DILDTAGRE (SEQ ID NO. 347) | ILDTAGRE (SEQ ID NO. 435) |
| | | | | LLDILDTAGREE (SEQ ID NO. 30) | LDILDTAGREE (SEQ ID NO. 145) | DILDTAGREE (SEQ ID NO. 251) | ILDTAGREE (SEQ ID NO. 348) | LDTAGREE (SEQ ID NO. 436) |
| | | | | LDILDTAGREEY (SEQ ID NO. 31) | DILDTAGREEY (SEQ ID NO. 146) | ILDTAGREEY (SEQ ID NO. 252) | LDTAGREEY (SEQ ID NO. 349) | DTAGREEY (SEQ ID NO. 437) |
| | | | | DILDTAGREEYS (SEQ ID NO. 32) | ILDTAGREEYS (SEQ ID NO. 147) | LDTAGREEYS (SEQ ID NO. 253) | DTAGREEYS (SEQ ID NO. 350) | TAGREEYS (SEQ ID NO. 438) |
| | | | | ILDTAGREEYSA (SEQ ID NO. 33) | LDTAGREEYSA (SEQ ID NO. 148) | DTAGREEYSA (SEQ ID NO. 254) | TAGREEYSA (SEQ ID NO. 351) | AGREEYSA (SEQ ID NO. 439) |
| | | | | LDTAGREEYSAM (SEQ ID NO. 34) | DTAGREEYSAM (SEQ ID NO. 149) | TAGREEYSAM (SEQ ID NO. 255) | AGREEYSAM (SEQ ID NO. 352) | GREEYSAM (SEQ ID NO. 440) |
| | | | | DTAGREEYSAMR (SEQ ID NO. 35) | TAGREEYSAMR (SEQ ID NO. 150) | AGREEYSAMR (SEQ ID NO. 256) | GREEYSAMR (SEQ ID NO. 353) | REEYSAMR (SEQ ID NO. 441) |
| | | | | TAGREEYSAMRD (SEQ ID NO. 36) | AGREEYSAMRD (SEQ ID NO. 151) | GREEYSAMRD (SEQ ID NO. 257) | REEYSAMRD (SEQ ID NO. 354) | |
| | | | | AGREEYSAMRDQ (SEQ ID NO. 37) | GREEYSAMRDQ (SEQ ID NO. 152) | REEYSAMRDQ (SEQ ID NO. 258) | | |
| | | | | GREEYSAMRDQY (SEQ ID NO. 38) | REEYSAMRDQY (SEQ ID NO. 153) | | | |
| | | | | REEYSAMRDQYM (SEQ ID NO. 39) | | | | |
| 4 | Human Lung Adenocarcinoma | K-Ras | G12V | MTEYKLVVVGAVGVGKSALTIQL (SEQ ID NO. 40) | TEYKLVVVGAVGVGKSALTIQ (SEQ ID NO. 154) | EYKLVVVGAVGVGKSALTI (SEQ ID NO. 259) | YKLVVVGAVGVGKSALT (SEQ ID NO. 355) | KLVVVGAVGVGKSAL (SEQ ID NO. 442) |
| | | | | MTEYKLVVVGAV (SEQ ID NO. 41) | TEYKLVVVGAV (SEQ ID NO. 155) | EYKLVVVGAV (SEQ ID NO. 260) | YKLVVVGAV (SEQ ID NO. 356) | KLVVVGAV (SEQ ID NO. 443) |
| | | | | TEYKLVVVGAVG (SEQ ID NO. 42) | EYKLVVVGAVG (SEQ ID NO. 156) | YKLVVVGAVG (SEQ ID NO. 261) | KLVVVGAVG (SEQ ID NO. 357) | LVVVGAVG (SEQ ID NO. 444) |
| | | | | EYKLVVVGAVGV (SEQ ID NO. 43) | YKLVVVGAVGV (SEQ ID NO. 157) | KLVVVGAVGV (SEQ ID NO. 262) | LVVVGAVGV (SEQ ID NO. 358) | VVVGAVGV (SEQ ID NO. 445) |
| | | | | YKLVVVGAVGVG (SEQ ID NO. 44) | KLVVVGAVGVG (SEQ ID NO. 158) | LVVVGAVGVG (SEQ ID NO. 263) | VVVGAVGVG (SEQ ID NO. 359) | VVGAVGVG (SEQ ID NO. 446) |

FIG. 3B

| | | | | | | | |
|---|---|---|---|---|---|---|---|
| | | | KLVVVGAVGVGK (SEQ ID NO. 45) | LVVVGAVGVGK (SEQ ID NO. 159) | VVVGAVGVGK (SEQ ID NO. 264) | VVGAVGVGK (SEQ ID NO. 360) | VGAVGVGK (SEQ ID NO. 447) |
| | | | LVVVGAVGVGKS (SEQ ID NO. 46) | VVVGAVGVGKS (SEQ ID NO. 160) | VVGAVGVGKS (SEQ ID NO. 265) | VGAVGVGKS (SEQ ID NO. 361) | GAVGVGKS (SEQ ID NO. 448) |
| | | | VVVGAVGVGKSA (SEQ ID NO. 47) | VVGAVGVGKSA (SEQ ID NO. 161) | VGAVGVGKSA (SEQ ID NO. 266) | GAVGVGKSA (SEQ ID NO. 362) | AVGVGKSA (SEQ ID NO. 449) |
| | | | VVGAVGVGKSAL (SEQ ID NO. 48) | VGAVGVGKSAL (SEQ ID NO. 162) | GAVGVGKSAL (SEQ ID NO. 267) | AVGVGKSAL (SEQ ID NO. 363) | VGVGKSAL (SEQ ID NO. 450) |
| | | | VGAVGVGKSALT (SEQ ID NO. 49) | GAVGVGKSALT (SEQ ID NO. 163) | AVGVGKSALT (SEQ ID NO. 268) | VGVGKSALT (SEQ ID NO. 364) | |
| | | | GAVGVGKSALTI (SEQ ID NO. 50) | AVGVGKSALTI (SEQ ID NO. 164) | VGVGKSALTI (SEQ ID NO. 269) | | |
| | | | AVGVGKSALTIQ (SEQ ID NO. 51) | VGVGKSALTIQ (SEQ ID NO. 165) | | | |
| | | | VGVGKSALTIQL (SEQ ID NO. 52) | | | | |
| 5 | Human Lung Adenocarcinoma | K-Ras | G12D | MTEYKLVVVGA<u>D</u>GVGKSALTIQL (SEQ ID NO. 53) | TEYKLVVVGADGV GKSALTIQ (SEQ ID NO. 166) | EYKLVVVGADGV GKSALTI (SEQ ID NO. 270) | YKLVVVGADGVG KSALT (SEQ ID NO. 365) | KLVVVGADGVGK SAL (SEQ ID NO. 451) |
| | | | | MTEYKLVVVGAD (SEQ ID NO. 54) | TEYKLVVVGAD (SEQ ID NO. 167) | EYKLVVVGAD (SEQ ID NO. 271) | YKLVVVGAD (SEQ ID NO. 366) | KLVVVGAD (SEQ ID NO. 452) |
| | | | | TEYKLVVVGADG (SEQ ID NO. 55) | EYKLVVVGADG (SEQ ID NO. 168) | YKLVVVGADG (SEQ ID NO. 272) | KLVVVGADG (SEQ ID NO. 367) | LVVVGADG (SEQ ID NO. 453) |
| | | | | EYKLVVVGADGV (SEQ ID NO. 56) | YKLVVVGADGV (SEQ ID NO. 169) | KLVVVGADGV (SEQ ID NO. 273) | LVVVGADGV (SEQ ID NO. 368) | VVVGADGV (SEQ ID NO. 454) |
| | | | | YKLVVVGADGVG (SEQ ID NO. 57) | KLVVVGADGVG (SEQ ID NO. 170) | LVVVGADGVG (SEQ ID NO. 274) | VVVGADGVG (SEQ ID NO. 369) | VVGADGVG (SEQ ID NO. 455) |
| | | | | KLVVVGADGVGK (SEQ ID NO. 58) | LVVVGADGVGK (SEQ ID NO. 171) | VVVGADGVGK (SEQ ID NO. 275) | VVGADGVGK (SEQ ID NO. 370) | VGADGVGK (SEQ ID NO. 456) |
| | | | | LVVVGADGVGKS (SEQ ID NO. 59) | VVVGADGVGKS (SEQ ID NO. 172) | VVGADGVGKS (SEQ ID NO. 276) | VGADGVGKS (SEQ ID NO. 371) | GADGVGKS (SEQ ID NO. 457) |
| | | | | VVVGADGVGKSA (SEQ ID NO. 60) | VVGADGVGKSA (SEQ ID NO. 173) | VGADGVGKSA (SEQ ID NO. 277) | GADGVGKSA (SEQ ID NO. 372) | ADGVGKSA (SEQ ID NO. 458) |
| | | | | VVGADGVGKSAL (SEQ ID NO. 61) | VGADGVGKSAL (SEQ ID NO. 174) | GADGVGKSAL (SEQ ID NO. 278) | ADGVGKSAL (SEQ ID NO. 373) | DGVGKSAL (SEQ ID NO. 459) |
| | | | | VGADGVGKSALT (SEQ ID NO. 62) | GADGVGKSALT (SEQ ID NO. 175) | ADGVGKSALT (SEQ ID NO. 279) | DGVGKSALT (SEQ ID NO. 374) | |
| | | | | GADGVGKSALTI (SEQ ID NO. 63) | ADGVGKSALTI (SEQ ID NO. 176) | DGVGKSALTI (SEQ ID NO. 280) | | |
| | | | | ADGVGKSALTIQ (SEQ ID NO. 64) | DGVGKSALTIQ (SEQ ID NO. 177) | | | |
| | | | | DGVGKSALTIQL (SEQ ID NO. 65) | | | | |
| 6 | Human Head and Neck Squamo | TP53 | Y220C | RNTFRHSVVVP<u>C</u>EPPEVGSDCTT (SEQ ID NO. 66) | NTFRHSVVVPCEP PEVGSDCT (SEQ ID NO. 178) | TFRHSVVVPCEPP EVGSDC (SEQ ID NO. 281) | FRHSVVVPCEPPE VGSD (SEQ ID NO. 375) | RHSVVVPCEPPEV GS (SEQ ID NO. 460) |
| | | | | RNTFRHSVVVPC (SEQ ID NO. 67) | NTFRHSVVVPC (SEQ ID NO. 179) | TFRHSVVVPC (SEQ ID NO. 282) | FRHSVVVPC (SEQ ID NO. 376) | RHSVVVPC (SEQ ID NO. 461) |

FIG. 3C

| | | | | | | | |
|---|---|---|---|---|---|---|---|
| | us Cell Carcinoma | | | NTFRHSVVVPCE (SEQ ID NO. 68) | TFRHSVVVPCE (SEQ ID NO. 180) | FRHSVVVPCE (SEQ ID NO. 283) | RHSVVVPCE (SEQ ID NO. 377) | HSVVVPCE (SEQ ID NO. 462) |
| | | | | TFRHSVVVPCEP (SEQ ID NO. 69) | FRHSVVVPCEP (SEQ ID NO. 181) | RHSVVVPCEP (SEQ ID NO. 284) | HSVVVPCEP (SEQ ID NO. 378) | SVVVPCEP (SEQ ID NO. 463) |
| | | | | FRHSVVVPCEPP (SEQ ID NO. 70) | RHSVVVPCEPP (SEQ ID NO. 182) | HSVVVPCEPP (SEQ ID NO. 285) | SVVVPCEPP (SEQ ID NO. 379) | VVVPCEPP (SEQ ID NO. 464) |
| | | | | RHSVVVPCEPPE (SEQ ID NO. 71) | HSVVVPCEPPE (SEQ ID NO. 183) | SVVVPCEPPE (SEQ ID NO. 286) | VVVPCEPPE (SEQ ID NO. 380) | VVPCEPPE (SEQ ID NO. 465) |
| | | | | HSVVVPCEPPEV (SEQ ID NO. 72) | SVVVPCEPPEV (SEQ ID NO. 184) | VVVPCEPPEV (SEQ ID NO. 287) | VVPCEPPEV (SEQ ID NO. 381) | VPCEPPEV (SEQ ID NO. 466) |
| | | | | SVVVPCEPPEVG (SEQ ID NO. 73) | VVVPCEPPEVG (SEQ ID NO. 185) | VVPCEPPEVG (SEQ ID NO. 288) | VPCEPPEVG (SEQ ID NO. 382) | PCEPPEVG (SEQ ID NO. 467) |
| | | | | VVVPCEPPEVGS (SEQ ID NO. 74) | VVPCEPPEVGS (SEQ ID NO. 186) | VPCEPPEVGS (SEQ ID NO. 289) | PCEPPEVGS (SEQ ID NO. 383) | CEPPEVGS (SEQ ID NO. 468) |
| | | | | VVPCEPPEVGSD (SEQ ID NO. 75) | VPCEPPEVGSD (SEQ ID NO. 187) | PCEPPEVGSD (SEQ ID NO. 290) | CEPPEVGSD (SEQ ID NO. 384) | |
| | | | | VPCEPPEVGSDC (SEQ ID NO. 76) | PCEPPEVGSDC (SEQ ID NO. 188) | CEPPEVGSDC (SEQ ID NO. 291) | | |
| | | | | PCEPPEVGSDCT (SEQ ID NO. 77) | CEPPEVGSDCT (SEQ ID NO. 189) | | | |
| | | | | CEPPEVGSDCTT (SEQ ID NO. 78) | | | | |
| 7 | Human Large Intestine Adenocarcinoma | TP53 | R248W | MCNSSCMGGMNWRPILTIITLED (SEQ ID NO. 79) | CNSSCMGGMNWRPILTIITLE (SEQ ID NO. 190) | NSSCMGGMNWRPILTIITL (SEQ ID NO. 292) | SSCMGGMNWRPILTIIT (SEQ ID NO. 385) | SCMGGMNWRPILTII (SEQ ID NO. 469) |
| | | | | MCNSSCMGGMNW (SEQ ID NO. 80) | CNSSCMGGMNW (SEQ ID NO. 191) | NSSCMGGMNW (SEQ ID NO. 293) | SSCMGGMNW (SEQ ID NO. 386) | SCMGGMNW (SEQ ID NO. 470) |
| | | | | CNSSCMGGMNWR (SEQ ID NO. 81) | NSSCMGGMNWR (SEQ ID NO. 192) | SSCMGGMNWR (SEQ ID NO. 294) | SCMGGMNWR (SEQ ID NO. 387) | CMGGMNWR (SEQ ID NO. 471) |
| | | | | NSSCMGGMNWRP (SEQ ID NO. 82) | SSCMGGMNWRP (SEQ ID NO. 193) | SCMGGMNWRP (SEQ ID NO. 295) | CMGGMNWRP (SEQ ID NO. 388) | MGGMNWRP (SEQ ID NO. 472) |
| | | | | SSCMGGMNWRPI (SEQ ID NO. 83) | SCMGGMNWRPI (SEQ ID NO. 194) | CMGGMNWRPI (SEQ ID NO. 296) | MGGMNWRPI (SEQ ID NO. 389) | GGMNWRPI (SEQ ID NO. 473) |
| | | | | SCMGGMNWRPIL (SEQ ID NO. 84) | CMGGMNWRPIL (SEQ ID NO. 195) | MGGMNWRPIL (SEQ ID NO. 297) | GGMNWRPIL (SEQ ID NO. 390) | GMNWRPIL (SEQ ID NO. 474) |
| | | | | CMGGMNWRPILT (SEQ ID NO. 85) | MGGMNWRPILT (SEQ ID NO. 196) | GGMNWRPILT (SEQ ID NO. 298) | GMNWRPILT (SEQ ID NO. 391) | MNWRPILT (SEQ ID NO. 475) |
| | | | | MGGMNWRPILTI (SEQ ID NO. 86) | GGMNWRPILTI (SEQ ID NO. 197) | GMNWRPILTI (SEQ ID NO. 299) | MNWRPILTI (SEQ ID NO. 392) | NWRPILTI (SEQ ID NO. 476) |
| | | | | GGMNWRPILTII (SEQ ID NO. 87) | GMNWRPILTII (SEQ ID NO. 198) | MNWRPILTII (SEQ ID NO. 300) | NWRPILTII (SEQ ID NO. 393) | WRPILTII (SEQ ID NO. 477) |
| | | | | GMNWRPILTIIT (SEQ ID NO. 88) | MNWRPILTIIT (SEQ ID NO. 199) | NWRPILTIIT (SEQ ID NO. 301) | WRPILTIIT (SEQ ID NO. 394) | |
| | | | | MNWRPILTIITL (SEQ ID NO. 89) | NWRPILTIITL (SEQ ID NO. 200) | WRPILTIITL (SEQ ID NO. 302) | | |

FIG. 3D

| | | | | | | | |
|---|---|---|---|---|---|---|---|
| | | | | NWRPILTIITLE (SEQ ID NO. 90) | WRPILTIITLE (SEQ ID NO. 201) | | |
| | | | | WRPILTIITLED (SEQ ID NO. 91) | | | |
| 8 | Human Lung Adenocarcinoma | TP53 | R213L | RVEYLDDRNTFLHSVVVPYEPPE (SEQ ID NO. 92) | VEYLDDRNTFLHSVVVPYEPP (SEQ ID NO. 202) | EYLDDRNTFLHSVVVPYEP (SEQ ID NO. 303) | YLDDRNTFLHSVVPYE (SEQ ID NO. 395) | LDDRNTFLHSVVVPY (SEQ ID NO. 478) |
| | | | | RVEYLDDRNTFL (SEQ ID NO. 93) | VEYLDDRNTFL (SEQ ID NO. 203) | EYLDDRNTFL (SEQ ID NO. 304) | YLDDRNTFL (SEQ ID NO. 396) | LDDRNTFL (SEQ ID NO. 479) |
| | | | | VEYLDDRNTFLH (SEQ ID NO. 94) | EYLDDRNTFLH (SEQ ID NO. 204) | YLDDRNTFLH (SEQ ID NO. 305) | LDDRNTFLH (SEQ ID NO. 397) | DDRNTFLH (SEQ ID NO. 480) |
| | | | | EYLDDRNTFLHS (SEQ ID NO. 95) | YLDDRNTFLHS (SEQ ID NO. 205) | LDDRNTFLHS (SEQ ID NO. 306) | DDRNTFLHS (SEQ ID NO. 398) | DRNTFLHS (SEQ ID NO. 481) |
| | | | | YLDDRNTFLHSV (SEQ ID NO. 96) | LDDRNTFLHSV (SEQ ID NO. 206) | DDRNTFLHSV (SEQ ID NO. 307) | DRNTFLHSV (SEQ ID NO. 399) | RNTFLHSV (SEQ ID NO. 482) |
| | | | | LDDRNTFLHSVV (SEQ ID NO. 97) | DDRNTFLHSVV (SEQ ID NO. 207) | DRNTFLHSVV (SEQ ID NO. 308) | RNTFLHSVV (SEQ ID NO. 400) | NTFLHSVV (SEQ ID NO. 483) |
| | | | | DDRNTFLHSVVV (SEQ ID NO. 98) | DRNTFLHSVVV (SEQ ID NO. 208) | RNTFLHSVVV (SEQ ID NO. 309) | NTFLHSVVV (SEQ ID NO. 401) | TFLHSVVV (SEQ ID NO. 484) |
| | | | | DRNTFLHSVVVP (SEQ ID NO. 99) | RNTFLHSVVVP (SEQ ID NO. 209) | NTFLHSVVVP (SEQ ID NO. 310) | TFLHSVVVP (SEQ ID NO. 402) | FLHSVVVP (SEQ ID NO. 485) |
| | | | | RNTFLHSVVVPY (SEQ ID NO. 100) | NTFLHSVVVPY (SEQ ID NO. 210) | TFLHSVVVPY (SEQ ID NO. 311) | FLHSVVVPY (SEQ ID NO. 403) | LHSVVVPY (SEQ ID NO. 486) |
| | | | | NTFLHSVVVPYE (SEQ ID NO. 101) | TFLHSVVVPYE (SEQ ID NO. 211) | FLHSVVVPYE (SEQ ID NO. 312) | LHSVVVPYE (SEQ ID NO. 404) | |
| | | | | TFLHSVVVPYEP (SEQ ID NO. 102) | FLHSVVVPYEP (SEQ ID NO. 212) | LHSVVVPYEP (SEQ ID NO. 313) | | |
| | | | | FLHSVVVPYEPP (SEQ ID NO. 103) | LHSVVVPYEPP (SEQ ID NO. 213) | | | |
| | | | | LHSVVVPYEPPE (SEQ ID NO. 104) | | | | |
| 9 | Human Glioma | IDH2 | R140Q | KKMWKSPNGTIQNILGGTVFREP (SEQ ID NO. 105) | KMWKSPNGTIQNILGGTVFRE (SEQ ID NO. 214) | MWKSPNGTIQNILGGTVFR (SEQ ID NO. 314) | WKSPNGTIQNILGGTVF (SEQ ID NO. 405) | KSPNGTIQNILGGTV (SEQ ID NO. 487) |
| | | | | KKMWKSPNGTIQ (SEQ ID NO. 106) | KMWKSPNGTIQ (SEQ ID NO. 215) | MWKSPNGTIQ (SEQ ID NO. 315) | WKSPNGTIQ (SEQ ID NO. 406) | KSPNGTIQ (SEQ ID NO. 488) |
| | | | | KMWKSPNGTIQN (SEQ ID NO. 107) | MWKSPNGTIQN (SEQ ID NO. 216) | WKSPNGTIQN (SEQ ID NO. 316) | KSPNGTIQN (SEQ ID NO. 407) | SPNGTIQN (SEQ ID NO. 489) |
| | | | | MWKSPNGTIQNI (SEQ ID NO. 108) | WKSPNGTIQNI (SEQ ID NO. 217) | KSPNGTIQNI (SEQ ID NO. 317) | SPNGTIQNI (SEQ ID NO. 408) | PNGTIQNI (SEQ ID NO. 490) |
| | | | | WKSPNGTIQNIL (SEQ ID NO. 109) | KSPNGTIQNIL (SEQ ID NO. 218) | SPNGTIQNIL (SEQ ID NO. 318) | PNGTIQNIL (SEQ ID NO. 409) | NGTIQNIL (SEQ ID NO. 491) |
| | | | | KSPNGTIQNILG (SEQ ID NO. 110) | SPNGTIQNILG (SEQ ID NO. 219) | PNGTIQNILG (SEQ ID NO. 319) | NGTIQNILG (SEQ ID NO. 410) | GTIQNILG (SEQ ID NO. 492) |
| | | | | SPNGTIQNILGG (SEQ ID NO. 111) | PNGTIQNILGG (SEQ ID NO. 220) | NGTIQNILGG (SEQ ID NO. 320) | GTIQNILGG (SEQ ID NO. 411) | TIQNILGG (SEQ ID NO. 493) |
| | | | | PNGTIQNILGGT (SEQ ID NO. 112) | NGTIQNILGGT (SEQ ID NO. 221) | GTIQNILGGT (SEQ ID NO. 321) | TIQNILGGT (SEQ ID NO. 412) | IQNILGGT (SEQ ID NO. 494) |

FIG. 3E

| | | | | NGTIQNILGGTV (SEQ ID NO. 113) | GTIQNILGGTV (SEQ ID NO. 222) | TIQNILGGTV (SEQ ID NO. 322) | IQNILGGTV (SEQ ID NO. 413) | QNILGGTV (SEQ ID NO. 495) |
|---|---|---|---|---|---|---|---|---|
| | | | | GTIQNILGGTVF (SEQ ID NO. 114) | TIQNILGGTVF (SEQ ID NO. 223) | IQNILGGTVF (SEQ ID NO. 323) | QNILGGTVF (SEQ ID NO. 414) | |
| | | | | TIQNILGGTVFR (SEQ ID NO. 115) | IQNILGGTVFR (SEQ ID NO. 224) | QNILGGTVFR (SEQ ID NO. 324) | | |
| | | | | IQNILGGTVFRE (SEQ ID NO. 116) | QNILGGTVFRE (SEQ ID NO. 225) | | | |
| | | | | QNILGGTVFREP (SEQ ID NO. 117) | | | | |
FIG. 3F
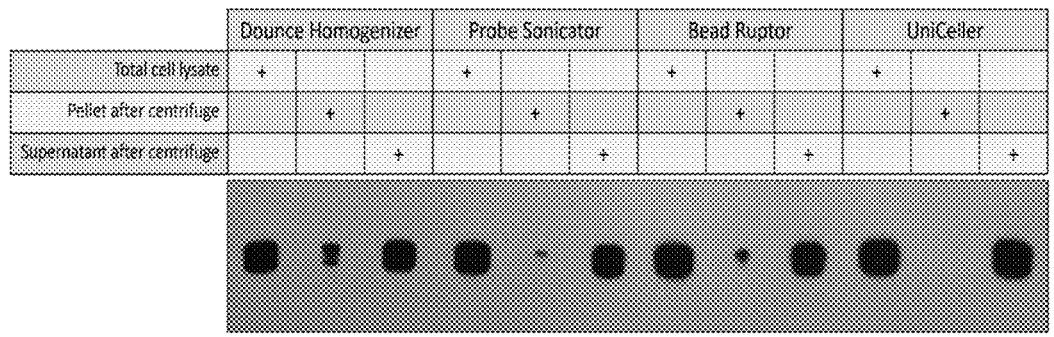
FIG. 4
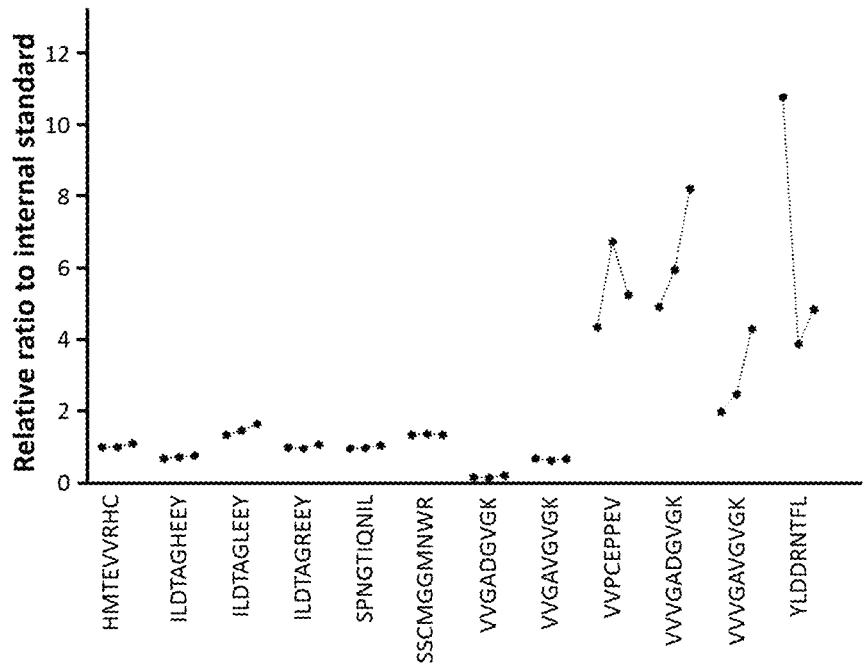
FIG. 5

SEQUENCE LISTING

```
<160> NUMBER OF SEQ ID NOS: 541

<210> SEQ ID NO 1
<211> LENGTH: 23
<212> TYPE: PRT
<213> ORGANISM: homo sapiens

<400> SEQUENCE: 1

Thr Cys Leu Leu Asp Ile Leu Asp Thr Ala Gly His Glu Glu Tyr Ser
1               5                   10                  15

Ala Met Arg Asp Gln Tyr Met
            20

<210> SEQ ID NO 2
<211> LENGTH: 12
<212> TYPE: PRT
<213> ORGANISM: homo sapiens

<400> SEQUENCE: 2

Thr Cys Leu Leu Asp Ile Leu Asp Thr Ala Gly His
1               5                   10

<210> SEQ ID NO 3
<211> LENGTH: 12
<212> TYPE: PRT
<213> ORGANISM: homo sapiens

<400> SEQUENCE: 3

Cys Leu Leu Asp Ile Leu Asp Thr Ala Gly His Glu
1               5                   10

<210> SEQ ID NO 4
<211> LENGTH: 12
<212> TYPE: PRT
<213> ORGANISM: homo sapiens

<400> SEQUENCE: 4

Leu Leu Asp Ile Leu Asp Thr Ala Gly His Glu Glu
1               5                   10

<210> SEQ ID NO 5
<211> LENGTH: 12
<212> TYPE: PRT
<213> ORGANISM: homo sapiens
```

```
<400> SEQUENCE: 5

Leu Asp Ile Leu Asp Thr Ala Gly His Glu Glu Tyr
1               5                   10

<210> SEQ ID NO 6
<211> LENGTH: 12
<212> TYPE: PRT
<213> ORGANISM: homo sapiens

<400> SEQUENCE: 6

Asp Ile Leu Asp Thr Ala Gly His Glu Glu Tyr Ser
1               5                   10

<210> SEQ ID NO 7
<211> LENGTH: 12
<212> TYPE: PRT
<213> ORGANISM: homo sapiens

<400> SEQUENCE: 7

Ile Leu Asp Thr Ala Gly His Glu Glu Tyr Ser Ala
1               5                   10

<210> SEQ ID NO 8
<211> LENGTH: 12
<212> TYPE: PRT
<213> ORGANISM: homo sapiens

<400> SEQUENCE: 8

Leu Asp Thr Ala Gly His Glu Glu Tyr Ser Ala Met
1               5                   10

<210> SEQ ID NO 9
<211> LENGTH: 12
<212> TYPE: PRT
<213> ORGANISM: homo sapiens

<400> SEQUENCE: 9

Asp Thr Ala Gly His Glu Glu Tyr Ser Ala Met Arg
1               5                   10

<210> SEQ ID NO 10
<211> LENGTH: 12
<212> TYPE: PRT
<213> ORGANISM: homo sapiens

<400> SEQUENCE: 10

Thr Ala Gly His Glu Glu Tyr Ser Ala Met Arg Asp
1               5                   10

<210> SEQ ID NO 11
<211> LENGTH: 12
<212> TYPE: PRT
<213> ORGANISM: homo sapiens

<400> SEQUENCE: 11

Ala Gly His Glu Glu Tyr Ser Ala Met Arg Asp Gln
1               5                   10

<210> SEQ ID NO 12
<211> LENGTH: 12
<212> TYPE: PRT
<213> ORGANISM: homo sapiens

<400> SEQUENCE: 12
```

```
Gly His Glu Glu Tyr Ser Ala Met Arg Asp Gln Tyr
1               5                   10
```

<210> SEQ ID NO 13
<211> LENGTH: 12
<212> TYPE: PRT
<213> ORGANISM: homo sapiens

<400> SEQUENCE: 13

```
His Glu Glu Tyr Ser Ala Met Arg Asp Gln Tyr Met
1               5                   10
```

<210> SEQ ID NO 14
<211> LENGTH: 23
<212> TYPE: PRT
<213> ORGANISM: homo sapiens

<400> SEQUENCE: 14

```
Thr Cys Leu Leu Asp Ile Leu Asp Thr Ala Gly Leu Glu Glu Tyr Ser
1               5                   10                  15

Ala Met Arg Asp Gln Tyr Met
            20
```

<210> SEQ ID NO 15
<211> LENGTH: 12
<212> TYPE: PRT
<213> ORGANISM: homo sapiens

<400> SEQUENCE: 15

```
Thr Cys Leu Leu Asp Ile Leu Asp Thr Ala Gly Leu
1               5                   10
```

<210> SEQ ID NO 16
<211> LENGTH: 12
<212> TYPE: PRT
<213> ORGANISM: homo sapiens

<400> SEQUENCE: 16

```
Cys Leu Leu Asp Ile Leu Asp Thr Ala Gly Leu Glu
1               5                   10
```

<210> SEQ ID NO 17
<211> LENGTH: 12
<212> TYPE: PRT
<213> ORGANISM: homo sapiens

<400> SEQUENCE: 17

```
Leu Leu Asp Ile Leu Asp Thr Ala Gly Leu Glu Glu
1               5                   10
```

<210> SEQ ID NO 18
<211> LENGTH: 12
<212> TYPE: PRT
<213> ORGANISM: homo sapiens

<400> SEQUENCE: 18

```
Leu Asp Ile Leu Asp Thr Ala Gly Leu Glu Glu Tyr
1               5                   10
```

<210> SEQ ID NO 19
<211> LENGTH: 12
<212> TYPE: PRT
<213> ORGANISM: homo sapiens

<400> SEQUENCE: 19

```
Asp Ile Leu Asp Thr Ala Gly Leu Glu Glu Tyr Ser
1               5                   10
```

<210> SEQ ID NO 20
<211> LENGTH: 12
<212> TYPE: PRT
<213> ORGANISM: homo sapiens

<400> SEQUENCE: 20

```
Ile Leu Asp Thr Ala Gly Leu Glu Glu Tyr Ser Ala
1               5                   10
```

<210> SEQ ID NO 21
<211> LENGTH: 12
<212> TYPE: PRT
<213> ORGANISM: homo sapiens

<400> SEQUENCE: 21

```
Leu Asp Thr Ala Gly Leu Glu Glu Tyr Ser Ala Met
1               5                   10
```

<210> SEQ ID NO 22
<211> LENGTH: 12
<212> TYPE: PRT
<213> ORGANISM: homo sapiens

<400> SEQUENCE: 22

```
Asp Thr Ala Gly Leu Glu Glu Tyr Ser Ala Met Arg
1               5                   10
```

<210> SEQ ID NO 23
<211> LENGTH: 12
<212> TYPE: PRT
<213> ORGANISM: homo sapiens

<400> SEQUENCE: 23

```
Thr Ala Gly Leu Glu Glu Tyr Ser Ala Met Arg Asp
1               5                   10
```

<210> SEQ ID NO 24
<211> LENGTH: 12
<212> TYPE: PRT
<213> ORGANISM: homo sapiens

<400> SEQUENCE: 24

```
Ala Gly Leu Glu Glu Tyr Ser Ala Met Arg Asp Gln
1               5                   10
```

<210> SEQ ID NO 25
<211> LENGTH: 12
<212> TYPE: PRT
<213> ORGANISM: homo sapiens

<400> SEQUENCE: 25

```
Gly Leu Glu Glu Tyr Ser Ala Met Arg Asp Gln Tyr
1               5                   10
```

<210> SEQ ID NO 26
<211> LENGTH: 12
<212> TYPE: PRT
<213> ORGANISM: homo sapiens

<400> SEQUENCE: 26

```
Leu Glu Glu Tyr Ser Ala Met Arg Asp Gln Tyr Met
```

-continued

```
<210> SEQ ID NO 27
<211> LENGTH: 23
<212> TYPE: PRT
<213> ORGANISM: homo sapiens

<400> SEQUENCE: 27

Thr Cys Leu Leu Asp Ile Leu Asp Thr Ala Gly Arg Glu Glu Tyr Ser
1               5                   10                  15

Ala Met Arg Asp Gln Tyr Met
            20

<210> SEQ ID NO 28
<211> LENGTH: 12
<212> TYPE: PRT
<213> ORGANISM: homo sapiens

<400> SEQUENCE: 28

Thr Cys Leu Leu Asp Ile Leu Asp Thr Ala Gly Arg
1               5                   10

<210> SEQ ID NO 29
<211> LENGTH: 12
<212> TYPE: PRT
<213> ORGANISM: homo sapiens

<400> SEQUENCE: 29

Cys Leu Leu Asp Ile Leu Asp Thr Ala Gly Arg Glu
1               5                   10

<210> SEQ ID NO 30
<211> LENGTH: 12
<212> TYPE: PRT
<213> ORGANISM: homo sapiens

<400> SEQUENCE: 30

Leu Leu Asp Ile Leu Asp Thr Ala Gly Arg Glu Glu
1               5                   10

<210> SEQ ID NO 31
<211> LENGTH: 12
<212> TYPE: PRT
<213> ORGANISM: homo sapiens

<400> SEQUENCE: 31

Leu Asp Ile Leu Asp Thr Ala Gly Arg Glu Glu Tyr
1               5                   10

<210> SEQ ID NO 32
<211> LENGTH: 12
<212> TYPE: PRT
<213> ORGANISM: homo sapiens

<400> SEQUENCE: 32

Asp Ile Leu Asp Thr Ala Gly Arg Glu Glu Tyr Ser
1               5                   10

<210> SEQ ID NO 33
<211> LENGTH: 12
<212> TYPE: PRT
<213> ORGANISM: homo sapiens

<400> SEQUENCE: 33
```

Ile Leu Asp Thr Ala Gly Arg Glu Glu Tyr Ser Ala
1               5                   10

<210> SEQ ID NO 34
<211> LENGTH: 12
<212> TYPE: PRT
<213> ORGANISM: homo sapiens

<400> SEQUENCE: 34

Leu Asp Thr Ala Gly Arg Glu Glu Tyr Ser Ala Met
1               5                   10

<210> SEQ ID NO 35
<211> LENGTH: 12
<212> TYPE: PRT
<213> ORGANISM: homo sapiens

<400> SEQUENCE: 35

Asp Thr Ala Gly Arg Glu Glu Tyr Ser Ala Met Arg
1               5                   10

<210> SEQ ID NO 36
<211> LENGTH: 12
<212> TYPE: PRT
<213> ORGANISM: homo sapiens

<400> SEQUENCE: 36

Thr Ala Gly Arg Glu Glu Tyr Ser Ala Met Arg Asp
1               5                   10

<210> SEQ ID NO 37
<211> LENGTH: 12
<212> TYPE: PRT
<213> ORGANISM: homo sapiens

<400> SEQUENCE: 37

Ala Gly Arg Glu Glu Tyr Ser Ala Met Arg Asp Gln
1               5                   10

<210> SEQ ID NO 38
<211> LENGTH: 12
<212> TYPE: PRT
<213> ORGANISM: homo sapiens

<400> SEQUENCE: 38

Gly Arg Glu Glu Tyr Ser Ala Met Arg Asp Gln Tyr
1               5                   10

<210> SEQ ID NO 39
<211> LENGTH: 12
<212> TYPE: PRT
<213> ORGANISM: homo sapiens

<400> SEQUENCE: 39

Arg Glu Glu Tyr Ser Ala Met Arg Asp Gln Tyr Met
1               5                   10

<210> SEQ ID NO 40
<211> LENGTH: 23
<212> TYPE: PRT
<213> ORGANISM: homo sapiens

<400> SEQUENCE: 40

Met Thr Glu Tyr Lys Leu Val Val Val Gly Ala Val Gly Val Gly Lys
1               5                   10                  15

Ser Ala Leu Thr Ile Gln Leu
            20

<210> SEQ ID NO 41
<211> LENGTH: 12
<212> TYPE: PRT
<213> ORGANISM: homo sapiens

<400> SEQUENCE: 41

Met Thr Glu Tyr Lys Leu Val Val Val Gly Ala Val
1               5                   10

<210> SEQ ID NO 42
<211> LENGTH: 12
<212> TYPE: PRT
<213> ORGANISM: homo sapiens

<400> SEQUENCE: 42

Thr Glu Tyr Lys Leu Val Val Val Gly Ala Val Gly
1               5                   10

<210> SEQ ID NO 43
<211> LENGTH: 12
<212> TYPE: PRT
<213> ORGANISM: homo sapiens

<400> SEQUENCE: 43

Glu Tyr Lys Leu Val Val Val Gly Ala Val Gly Val
1               5                   10

<210> SEQ ID NO 44
<211> LENGTH: 12
<212> TYPE: PRT
<213> ORGANISM: homo sapiens

<400> SEQUENCE: 44

Tyr Lys Leu Val Val Val Gly Ala Val Gly Val Gly
1               5                   10

<210> SEQ ID NO 45
<211> LENGTH: 12
<212> TYPE: PRT
<213> ORGANISM: homo sapiens

<400> SEQUENCE: 45

Lys Leu Val Val Val Gly Ala Val Gly Val Gly Lys
1               5                   10

<210> SEQ ID NO 46
<211> LENGTH: 12
<212> TYPE: PRT
<213> ORGANISM: homo sapiens

<400> SEQUENCE: 46

Leu Val Val Val Gly Ala Val Gly Val Gly Lys Ser
1               5                   10

<210> SEQ ID NO 47
<211> LENGTH: 12
<212> TYPE: PRT
<213> ORGANISM: homo sapiens

<400> SEQUENCE: 47

Val Val Val Gly Ala Val Gly Val Gly Lys Ser Ala

<210> SEQ ID NO 48
<211> LENGTH: 12
<212> TYPE: PRT
<213> ORGANISM: homo sapiens

<400> SEQUENCE: 48

Val Val Gly Ala Val Gly Val Gly Lys Ser Ala Leu
1               5                   10

<210> SEQ ID NO 49
<211> LENGTH: 12
<212> TYPE: PRT
<213> ORGANISM: homo sapiens

<400> SEQUENCE: 49

Val Gly Ala Val Gly Val Gly Lys Ser Ala Leu Thr
1               5                   10

<210> SEQ ID NO 50
<211> LENGTH: 12
<212> TYPE: PRT
<213> ORGANISM: homo sapiens

<400> SEQUENCE: 50

Gly Ala Val Gly Val Gly Lys Ser Ala Leu Thr Ile
1               5                   10

<210> SEQ ID NO 51
<211> LENGTH: 12
<212> TYPE: PRT
<213> ORGANISM: homo sapiens

<400> SEQUENCE: 51

Ala Val Gly Val Gly Lys Ser Ala Leu Thr Ile Gln
1               5                   10

<210> SEQ ID NO 52
<211> LENGTH: 12
<212> TYPE: PRT
<213> ORGANISM: homo sapiens

<400> SEQUENCE: 52

Val Gly Val Gly Lys Ser Ala Leu Thr Ile Gln Leu
1               5                   10

<210> SEQ ID NO 53
<211> LENGTH: 23
<212> TYPE: PRT
<213> ORGANISM: homo sapiens

<400> SEQUENCE: 53

Met Thr Glu Tyr Lys Leu Val Val Val Gly Ala Asp Gly Val Gly Lys
1               5                   10                  15

Ser Ala Leu Thr Ile Gln Leu
            20

<210> SEQ ID NO 54
<211> LENGTH: 12
<212> TYPE: PRT
<213> ORGANISM: homo sapiens

<400> SEQUENCE: 54

```
Met Thr Glu Tyr Lys Leu Val Val Val Gly Ala Asp
1               5                   10
```

<210> SEQ ID NO 55
<211> LENGTH: 12
<212> TYPE: PRT
<213> ORGANISM: homo sapiens

<400> SEQUENCE: 55

```
Thr Glu Tyr Lys Leu Val Val Val Gly Ala Asp Gly
1               5                   10
```

<210> SEQ ID NO 56
<211> LENGTH: 12
<212> TYPE: PRT
<213> ORGANISM: homo sapiens

<400> SEQUENCE: 56

```
Glu Tyr Lys Leu Val Val Val Gly Ala Asp Gly Val
1               5                   10
```

<210> SEQ ID NO 57
<211> LENGTH: 12
<212> TYPE: PRT
<213> ORGANISM: homo sapiens

<400> SEQUENCE: 57

```
Tyr Lys Leu Val Val Val Gly Ala Asp Gly Val Gly
1               5                   10
```

<210> SEQ ID NO 58
<211> LENGTH: 12
<212> TYPE: PRT
<213> ORGANISM: homo sapiens

<400> SEQUENCE: 58

```
Lys Leu Val Val Val Gly Ala Asp Gly Val Gly Lys
1               5                   10
```

<210> SEQ ID NO 59
<211> LENGTH: 12
<212> TYPE: PRT
<213> ORGANISM: homo sapiens

<400> SEQUENCE: 59

```
Leu Val Val Val Gly Ala Asp Gly Val Gly Lys Ser
1               5                   10
```

<210> SEQ ID NO 60
<211> LENGTH: 12
<212> TYPE: PRT
<213> ORGANISM: homo sapiens

<400> SEQUENCE: 60

```
Val Val Val Gly Ala Asp Gly Val Gly Lys Ser Ala
1               5                   10
```

<210> SEQ ID NO 61
<211> LENGTH: 12
<212> TYPE: PRT
<213> ORGANISM: homo sapiens

<400> SEQUENCE: 61

```
Val Val Gly Ala Asp Gly Val Gly Lys Ser Ala Leu
1               5                   10
```

<210> SEQ ID NO 62
<211> LENGTH: 12
<212> TYPE: PRT
<213> ORGANISM: homo sapiens

<400> SEQUENCE: 62

Val Gly Ala Asp Gly Val Gly Lys Ser Ala Leu Thr
1               5                   10

<210> SEQ ID NO 63
<211> LENGTH: 12
<212> TYPE: PRT
<213> ORGANISM: homo sapiens

<400> SEQUENCE: 63

Gly Ala Asp Gly Val Gly Lys Ser Ala Leu Thr Ile
1               5                   10

<210> SEQ ID NO 64
<211> LENGTH: 12
<212> TYPE: PRT
<213> ORGANISM: homo sapiens

<400> SEQUENCE: 64

Ala Asp Gly Val Gly Lys Ser Ala Leu Thr Ile Gln
1               5                   10

<210> SEQ ID NO 65
<211> LENGTH: 12
<212> TYPE: PRT
<213> ORGANISM: homo sapiens

<400> SEQUENCE: 65

Asp Gly Val Gly Lys Ser Ala Leu Thr Ile Gln Leu
1               5                   10

<210> SEQ ID NO 66
<211> LENGTH: 23
<212> TYPE: PRT
<213> ORGANISM: homo sapiens

<400> SEQUENCE: 66

Arg Asn Thr Phe Arg His Ser Val Val Val Pro Cys Glu Pro Pro Glu
1               5                   10                  15

Val Gly Ser Asp Cys Thr Thr
            20

<210> SEQ ID NO 67
<211> LENGTH: 12
<212> TYPE: PRT
<213> ORGANISM: homo sapiens

<400> SEQUENCE: 67

Arg Asn Thr Phe Arg His Ser Val Val Val Pro Cys
1               5                   10

<210> SEQ ID NO 68
<211> LENGTH: 12
<212> TYPE: PRT
<213> ORGANISM: homo sapiens

<400> SEQUENCE: 68

Asn Thr Phe Arg His Ser Val Val Val Pro Cys Glu

<210> SEQ ID NO 69
<211> LENGTH: 12
<212> TYPE: PRT
<213> ORGANISM: homo sapiens

<400> SEQUENCE: 69

Thr Phe Arg His Ser Val Val Val Pro Cys Glu Pro
1               5                   10

<210> SEQ ID NO 70
<211> LENGTH: 12
<212> TYPE: PRT
<213> ORGANISM: homo sapiens

<400> SEQUENCE: 70

Phe Arg His Ser Val Val Val Pro Cys Glu Pro Pro
1               5                   10

<210> SEQ ID NO 71
<211> LENGTH: 12
<212> TYPE: PRT
<213> ORGANISM: homo sapiens

<400> SEQUENCE: 71

Arg His Ser Val Val Val Pro Cys Glu Pro Pro Glu
1               5                   10

<210> SEQ ID NO 72
<211> LENGTH: 12
<212> TYPE: PRT
<213> ORGANISM: homo sapiens

<400> SEQUENCE: 72

His Ser Val Val Val Pro Cys Glu Pro Pro Glu Val
1               5                   10

<210> SEQ ID NO 73
<211> LENGTH: 12
<212> TYPE: PRT
<213> ORGANISM: homo sapiens

<400> SEQUENCE: 73

Ser Val Val Val Pro Cys Glu Pro Pro Glu Val Gly
1               5                   10

<210> SEQ ID NO 74
<211> LENGTH: 12
<212> TYPE: PRT
<213> ORGANISM: homo sapiens

<400> SEQUENCE: 74

Val Val Val Pro Cys Glu Pro Pro Glu Val Gly Ser
1               5                   10

<210> SEQ ID NO 75
<211> LENGTH: 12
<212> TYPE: PRT
<213> ORGANISM: homo sapiens

<400> SEQUENCE: 75

Val Val Pro Cys Glu Pro Pro Glu Val Gly Ser Asp
1               5                   10

<210> SEQ ID NO 76
<211> LENGTH: 12
<212> TYPE: PRT
<213> ORGANISM: homo sapiens

<400> SEQUENCE: 76

Val Pro Cys Glu Pro Pro Glu Val Gly Ser Asp Cys
1               5                   10

<210> SEQ ID NO 77
<211> LENGTH: 12
<212> TYPE: PRT
<213> ORGANISM: homo sapiens

<400> SEQUENCE: 77

Pro Cys Glu Pro Pro Glu Val Gly Ser Asp Cys Thr
1               5                   10

<210> SEQ ID NO 78
<211> LENGTH: 12
<212> TYPE: PRT
<213> ORGANISM: homo sapiens

<400> SEQUENCE: 78

Cys Glu Pro Pro Glu Val Gly Ser Asp Cys Thr Thr
1               5                   10

<210> SEQ ID NO 79
<211> LENGTH: 23
<212> TYPE: PRT
<213> ORGANISM: homo sapiens

<400> SEQUENCE: 79

Met Cys Asn Ser Ser Cys Met Gly Gly Met Asn Trp Arg Pro Ile Leu
1               5                   10                  15

Thr Ile Ile Thr Leu Glu Asp
            20

<210> SEQ ID NO 80
<211> LENGTH: 12
<212> TYPE: PRT
<213> ORGANISM: homo sapiens

<400> SEQUENCE: 80

Met Cys Asn Ser Ser Cys Met Gly Gly Met Asn Trp
1               5                   10

<210> SEQ ID NO 81
<211> LENGTH: 12
<212> TYPE: PRT
<213> ORGANISM: homo sapiens

<400> SEQUENCE: 81

Cys Asn Ser Ser Cys Met Gly Gly Met Asn Trp Arg
1               5                   10

<210> SEQ ID NO 82
<211> LENGTH: 12
<212> TYPE: PRT
<213> ORGANISM: homo sapiens

<400> SEQUENCE: 82

Asn Ser Ser Cys Met Gly Gly Met Asn Trp Arg Pro
1               5                   10

<210> SEQ ID NO 83
<211> LENGTH: 12
<212> TYPE: PRT
<213> ORGANISM: homo sapiens

<400> SEQUENCE: 83

Ser Ser Cys Met Gly Gly Met Asn Trp Arg Pro Ile
1               5                   10

<210> SEQ ID NO 84
<211> LENGTH: 12
<212> TYPE: PRT
<213> ORGANISM: homo sapiens

<400> SEQUENCE: 84

Ser Cys Met Gly Gly Met Asn Trp Arg Pro Ile Leu
1               5                   10

<210> SEQ ID NO 85
<211> LENGTH: 12
<212> TYPE: PRT
<213> ORGANISM: homo sapiens

<400> SEQUENCE: 85

Cys Met Gly Gly Met Asn Trp Arg Pro Ile Leu Thr
1               5                   10

<210> SEQ ID NO 86
<211> LENGTH: 12
<212> TYPE: PRT
<213> ORGANISM: homo sapiens

<400> SEQUENCE: 86

Met Gly Gly Met Asn Trp Arg Pro Ile Leu Thr Ile
1               5                   10

<210> SEQ ID NO 87
<211> LENGTH: 12
<212> TYPE: PRT
<213> ORGANISM: homo sapiens

<400> SEQUENCE: 87

Gly Gly Met Asn Trp Arg Pro Ile Leu Thr Ile Ile
1               5                   10

<210> SEQ ID NO 88
<211> LENGTH: 12
<212> TYPE: PRT
<213> ORGANISM: homo sapiens

<400> SEQUENCE: 88

Gly Met Asn Trp Arg Pro Ile Leu Thr Ile Ile Thr
1               5                   10

<210> SEQ ID NO 89
<211> LENGTH: 12
<212> TYPE: PRT
<213> ORGANISM: homo sapiens

<400> SEQUENCE: 89

Met Asn Trp Arg Pro Ile Leu Thr Ile Ile Thr Leu
1               5                   10

```
<210> SEQ ID NO 90
<211> LENGTH: 12
<212> TYPE: PRT
<213> ORGANISM: homo sapiens

<400> SEQUENCE: 90

Asn Trp Arg Pro Ile Leu Thr Ile Ile Thr Leu Glu
1               5                   10

<210> SEQ ID NO 91
<211> LENGTH: 12
<212> TYPE: PRT
<213> ORGANISM: homo sapiens

<400> SEQUENCE: 91

Trp Arg Pro Ile Leu Thr Ile Ile Thr Leu Glu Asp
1               5                   10

<210> SEQ ID NO 92
<211> LENGTH: 23
<212> TYPE: PRT
<213> ORGANISM: homo sapiens

<400> SEQUENCE: 92

Arg Val Glu Tyr Leu Asp Asp Arg Asn Thr Phe Leu His Ser Val Val
1               5                   10                  15

Val Pro Tyr Glu Pro Pro Glu
            20

<210> SEQ ID NO 93
<211> LENGTH: 12
<212> TYPE: PRT
<213> ORGANISM: homo sapiens

<400> SEQUENCE: 93

Arg Val Glu Tyr Leu Asp Asp Arg Asn Thr Phe Leu
1               5                   10

<210> SEQ ID NO 94
<211> LENGTH: 12
<212> TYPE: PRT
<213> ORGANISM: homo sapiens

<400> SEQUENCE: 94

Val Glu Tyr Leu Asp Asp Arg Asn Thr Phe Leu His
1               5                   10

<210> SEQ ID NO 95
<211> LENGTH: 12
<212> TYPE: PRT
<213> ORGANISM: homo sapiens

<400> SEQUENCE: 95

Glu Tyr Leu Asp Asp Arg Asn Thr Phe Leu His Ser
1               5                   10

<210> SEQ ID NO 96
<211> LENGTH: 12
<212> TYPE: PRT
<213> ORGANISM: homo sapiens

<400> SEQUENCE: 96

Tyr Leu Asp Asp Arg Asn Thr Phe Leu His Ser Val
1               5                   10
```

```
<210> SEQ ID NO 97
<211> LENGTH: 12
<212> TYPE: PRT
<213> ORGANISM: homo sapiens

<400> SEQUENCE: 97

Leu Asp Asp Arg Asn Thr Phe Leu His Ser Val Val
1               5                   10

<210> SEQ ID NO 98
<211> LENGTH: 12
<212> TYPE: PRT
<213> ORGANISM: homo sapiens

<400> SEQUENCE: 98

Asp Asp Arg Asn Thr Phe Leu His Ser Val Val Val
1               5                   10

<210> SEQ ID NO 99
<211> LENGTH: 12
<212> TYPE: PRT
<213> ORGANISM: homo sapiens

<400> SEQUENCE: 99

Asp Arg Asn Thr Phe Leu His Ser Val Val Val Pro
1               5                   10

<210> SEQ ID NO 100
<211> LENGTH: 12
<212> TYPE: PRT
<213> ORGANISM: homo sapiens

<400> SEQUENCE: 100

Arg Asn Thr Phe Leu His Ser Val Val Val Pro Tyr
1               5                   10

<210> SEQ ID NO 101
<211> LENGTH: 12
<212> TYPE: PRT
<213> ORGANISM: homo sapiens

<400> SEQUENCE: 101

Asn Thr Phe Leu His Ser Val Val Val Pro Tyr Glu
1               5                   10

<210> SEQ ID NO 102
<211> LENGTH: 12
<212> TYPE: PRT
<213> ORGANISM: homo sapiens

<400> SEQUENCE: 102

Thr Phe Leu His Ser Val Val Val Pro Tyr Glu Pro
1               5                   10

<210> SEQ ID NO 103
<211> LENGTH: 12
<212> TYPE: PRT
<213> ORGANISM: homo sapiens

<400> SEQUENCE: 103

Phe Leu His Ser Val Val Val Pro Tyr Glu Pro Pro
1               5                   10

<210> SEQ ID NO 104
```

```
<211> LENGTH: 12
<212> TYPE: PRT
<213> ORGANISM: homo sapiens

<400> SEQUENCE: 104

Leu His Ser Val Val Pro Tyr Glu Pro Pro Glu
1               5                   10

<210> SEQ ID NO 105
<211> LENGTH: 23
<212> TYPE: PRT
<213> ORGANISM: homo sapiens

<400> SEQUENCE: 105

Lys Lys Met Trp Lys Ser Pro Asn Gly Thr Ile Gln Asn Ile Leu Gly
1               5                   10                  15

Gly Thr Val Phe Arg Glu Pro
            20

<210> SEQ ID NO 106
<211> LENGTH: 12
<212> TYPE: PRT
<213> ORGANISM: homo sapiens

<400> SEQUENCE: 106

Lys Lys Met Trp Lys Ser Pro Asn Gly Thr Ile Gln
1               5                   10

<210> SEQ ID NO 107
<211> LENGTH: 12
<212> TYPE: PRT
<213> ORGANISM: homo sapiens

<400> SEQUENCE: 107

Lys Met Trp Lys Ser Pro Asn Gly Thr Ile Gln Asn
1               5                   10

<210> SEQ ID NO 108
<211> LENGTH: 12
<212> TYPE: PRT
<213> ORGANISM: homo sapiens

<400> SEQUENCE: 108

Met Trp Lys Ser Pro Asn Gly Thr Ile Gln Asn Ile
1               5                   10

<210> SEQ ID NO 109
<211> LENGTH: 12
<212> TYPE: PRT
<213> ORGANISM: homo sapiens

<400> SEQUENCE: 109

Trp Lys Ser Pro Asn Gly Thr Ile Gln Asn Ile Leu
1               5                   10

<210> SEQ ID NO 110
<211> LENGTH: 12
<212> TYPE: PRT
<213> ORGANISM: homo sapiens

<400> SEQUENCE: 110

Lys Ser Pro Asn Gly Thr Ile Gln Asn Ile Leu Gly
1               5                   10
```

```
<210> SEQ ID NO 111
<211> LENGTH: 12
<212> TYPE: PRT
<213> ORGANISM: homo sapiens

<400> SEQUENCE: 111

Ser Pro Asn Gly Thr Ile Gln Asn Ile Leu Gly Gly
1               5                   10

<210> SEQ ID NO 112
<211> LENGTH: 12
<212> TYPE: PRT
<213> ORGANISM: homo sapiens

<400> SEQUENCE: 112

Pro Asn Gly Thr Ile Gln Asn Ile Leu Gly Gly Thr
1               5                   10

<210> SEQ ID NO 113
<211> LENGTH: 12
<212> TYPE: PRT
<213> ORGANISM: homo sapiens

<400> SEQUENCE: 113

Asn Gly Thr Ile Gln Asn Ile Leu Gly Gly Thr Val
1               5                   10

<210> SEQ ID NO 114
<211> LENGTH: 12
<212> TYPE: PRT
<213> ORGANISM: homo sapiens

<400> SEQUENCE: 114

Gly Thr Ile Gln Asn Ile Leu Gly Gly Thr Val Phe
1               5                   10

<210> SEQ ID NO 115
<211> LENGTH: 12
<212> TYPE: PRT
<213> ORGANISM: homo sapiens

<400> SEQUENCE: 115

Thr Ile Gln Asn Ile Leu Gly Gly Thr Val Phe Arg
1               5                   10

<210> SEQ ID NO 116
<211> LENGTH: 12
<212> TYPE: PRT
<213> ORGANISM: homo sapiens

<400> SEQUENCE: 116

Ile Gln Asn Ile Leu Gly Gly Thr Val Phe Arg Glu
1               5                   10

<210> SEQ ID NO 117
<211> LENGTH: 12
<212> TYPE: PRT
<213> ORGANISM: homo sapiens

<400> SEQUENCE: 117

Gln Asn Ile Leu Gly Gly Thr Val Phe Arg Glu Pro
1               5                   10

<210> SEQ ID NO 118
<211> LENGTH: 21
```

<212> TYPE: PRT
<213> ORGANISM: homo sapiens

<400> SEQUENCE: 118

Cys Leu Leu Asp Ile Leu Asp Thr Ala Gly His Glu Glu Tyr Ser Ala
1               5                   10                  15
Met Arg Asp Gln Tyr
            20

<210> SEQ ID NO 119
<211> LENGTH: 11
<212> TYPE: PRT
<213> ORGANISM: homo sapiens

<400> SEQUENCE: 119

Cys Leu Leu Asp Ile Leu Asp Thr Ala Gly His
1               5                   10

<210> SEQ ID NO 120
<211> LENGTH: 11
<212> TYPE: PRT
<213> ORGANISM: homo sapiens

<400> SEQUENCE: 120

Leu Leu Asp Ile Leu Asp Thr Ala Gly His Glu
1               5                   10

<210> SEQ ID NO 121
<211> LENGTH: 11
<212> TYPE: PRT
<213> ORGANISM: homo sapiens

<400> SEQUENCE: 121

Leu Asp Ile Leu Asp Thr Ala Gly His Glu Glu
1               5                   10

<210> SEQ ID NO 122
<211> LENGTH: 11
<212> TYPE: PRT
<213> ORGANISM: homo sapiens

<400> SEQUENCE: 122

Asp Ile Leu Asp Thr Ala Gly His Glu Glu Tyr
1               5                   10

<210> SEQ ID NO 123
<211> LENGTH: 11
<212> TYPE: PRT
<213> ORGANISM: homo sapiens

<400> SEQUENCE: 123

Ile Leu Asp Thr Ala Gly His Glu Glu Tyr Ser
1               5                   10

<210> SEQ ID NO 124
<211> LENGTH: 11
<212> TYPE: PRT
<213> ORGANISM: homo sapiens

<400> SEQUENCE: 124

Leu Asp Thr Ala Gly His Glu Glu Tyr Ser Ala
1               5                   10

<210> SEQ ID NO 125

```
<211> LENGTH: 11
<212> TYPE: PRT
<213> ORGANISM: homo sapiens

<400> SEQUENCE: 125

Asp Thr Ala Gly His Glu Glu Tyr Ser Ala Met
1               5                   10

<210> SEQ ID NO 126
<211> LENGTH: 11
<212> TYPE: PRT
<213> ORGANISM: homo sapiens

<400> SEQUENCE: 126

Thr Ala Gly His Glu Glu Tyr Ser Ala Met Arg
1               5                   10

<210> SEQ ID NO 127
<211> LENGTH: 11
<212> TYPE: PRT
<213> ORGANISM: homo sapiens

<400> SEQUENCE: 127

Ala Gly His Glu Glu Tyr Ser Ala Met Arg Asp
1               5                   10

<210> SEQ ID NO 128
<211> LENGTH: 11
<212> TYPE: PRT
<213> ORGANISM: homo sapiens

<400> SEQUENCE: 128

Gly His Glu Glu Tyr Ser Ala Met Arg Asp Gln
1               5                   10

<210> SEQ ID NO 129
<211> LENGTH: 11
<212> TYPE: PRT
<213> ORGANISM: homo sapiens

<400> SEQUENCE: 129

His Glu Glu Tyr Ser Ala Met Arg Asp Gln Tyr
1               5                   10

<210> SEQ ID NO 130
<211> LENGTH: 21
<212> TYPE: PRT
<213> ORGANISM: homo sapiens

<400> SEQUENCE: 130

Cys Leu Leu Asp Ile Leu Asp Thr Ala Gly Leu Glu Glu Tyr Ser Ala
1               5                   10                  15

Met Arg Asp Gln Tyr
            20

<210> SEQ ID NO 131
<211> LENGTH: 11
<212> TYPE: PRT
<213> ORGANISM: homo sapiens

<400> SEQUENCE: 131

Cys Leu Leu Asp Ile Leu Asp Thr Ala Gly Leu
1               5                   10
```

-continued

```
<210> SEQ ID NO 132
<211> LENGTH: 11
<212> TYPE: PRT
<213> ORGANISM: homo sapiens

<400> SEQUENCE: 132

Leu Leu Asp Ile Leu Asp Thr Ala Gly Leu Glu
1               5                   10

<210> SEQ ID NO 133
<211> LENGTH: 11
<212> TYPE: PRT
<213> ORGANISM: homo sapiens

<400> SEQUENCE: 133

Leu Asp Ile Leu Asp Thr Ala Gly Leu Glu Glu
1               5                   10

<210> SEQ ID NO 134
<211> LENGTH: 11
<212> TYPE: PRT
<213> ORGANISM: homo sapiens

<400> SEQUENCE: 134

Asp Ile Leu Asp Thr Ala Gly Leu Glu Glu Tyr
1               5                   10

<210> SEQ ID NO 135
<211> LENGTH: 11
<212> TYPE: PRT
<213> ORGANISM: homo sapiens

<400> SEQUENCE: 135

Ile Leu Asp Thr Ala Gly Leu Glu Glu Tyr Ser
1               5                   10

<210> SEQ ID NO 136
<211> LENGTH: 11
<212> TYPE: PRT
<213> ORGANISM: homo sapiens

<400> SEQUENCE: 136

Leu Asp Thr Ala Gly Leu Glu Glu Tyr Ser Ala
1               5                   10

<210> SEQ ID NO 137
<211> LENGTH: 11
<212> TYPE: PRT
<213> ORGANISM: homo sapiens

<400> SEQUENCE: 137

Asp Thr Ala Gly Leu Glu Glu Tyr Ser Ala Met
1               5                   10

<210> SEQ ID NO 138
<211> LENGTH: 11
<212> TYPE: PRT
<213> ORGANISM: homo sapiens

<400> SEQUENCE: 138

Thr Ala Gly Leu Glu Glu Tyr Ser Ala Met Arg
1               5                   10

<210> SEQ ID NO 139
<211> LENGTH: 11
```

```
<212> TYPE: PRT
<213> ORGANISM: homo sapiens

<400> SEQUENCE: 139

Ala Gly Leu Glu Glu Tyr Ser Ala Met Arg Asp
1               5                   10

<210> SEQ ID NO 140
<211> LENGTH: 11
<212> TYPE: PRT
<213> ORGANISM: homo sapiens

<400> SEQUENCE: 140

Gly Leu Glu Glu Tyr Ser Ala Met Arg Asp Gln
1               5                   10

<210> SEQ ID NO 141
<211> LENGTH: 11
<212> TYPE: PRT
<213> ORGANISM: homo sapiens

<400> SEQUENCE: 141

Leu Glu Glu Tyr Ser Ala Met Arg Asp Gln Tyr
1               5                   10

<210> SEQ ID NO 142
<211> LENGTH: 21
<212> TYPE: PRT
<213> ORGANISM: homo sapiens

<400> SEQUENCE: 142

Cys Leu Leu Asp Ile Leu Asp Thr Ala Gly Arg Glu Glu Tyr Ser Ala
1               5                   10                  15

Met Arg Asp Gln Tyr
            20

<210> SEQ ID NO 143
<211> LENGTH: 11
<212> TYPE: PRT
<213> ORGANISM: homo sapiens

<400> SEQUENCE: 143

Cys Leu Leu Asp Ile Leu Asp Thr Ala Gly Arg
1               5                   10

<210> SEQ ID NO 144
<211> LENGTH: 11
<212> TYPE: PRT
<213> ORGANISM: homo sapiens

<400> SEQUENCE: 144

Leu Leu Asp Ile Leu Asp Thr Ala Gly Arg Glu
1               5                   10

<210> SEQ ID NO 145
<211> LENGTH: 11
<212> TYPE: PRT
<213> ORGANISM: homo sapiens

<400> SEQUENCE: 145

Leu Asp Ile Leu Asp Thr Ala Gly Arg Glu Glu
1               5                   10

<210> SEQ ID NO 146
```

```
<211> LENGTH: 11
<212> TYPE: PRT
<213> ORGANISM: homo sapiens

<400> SEQUENCE: 146

Asp Ile Leu Asp Thr Ala Gly Arg Glu Glu Tyr
1               5                   10

<210> SEQ ID NO 147
<211> LENGTH: 11
<212> TYPE: PRT
<213> ORGANISM: homo sapiens

<400> SEQUENCE: 147

Ile Leu Asp Thr Ala Gly Arg Glu Glu Tyr Ser
1               5                   10

<210> SEQ ID NO 148
<211> LENGTH: 11
<212> TYPE: PRT
<213> ORGANISM: homo sapiens

<400> SEQUENCE: 148

Leu Asp Thr Ala Gly Arg Glu Glu Tyr Ser Ala
1               5                   10

<210> SEQ ID NO 149
<211> LENGTH: 11
<212> TYPE: PRT
<213> ORGANISM: homo sapiens

<400> SEQUENCE: 149

Asp Thr Ala Gly Arg Glu Glu Tyr Ser Ala Met
1               5                   10

<210> SEQ ID NO 150
<211> LENGTH: 11
<212> TYPE: PRT
<213> ORGANISM: homo sapiens

<400> SEQUENCE: 150

Thr Ala Gly Arg Glu Glu Tyr Ser Ala Met Arg
1               5                   10

<210> SEQ ID NO 151
<211> LENGTH: 11
<212> TYPE: PRT
<213> ORGANISM: homo sapiens

<400> SEQUENCE: 151

Ala Gly Arg Glu Glu Tyr Ser Ala Met Arg Asp
1               5                   10

<210> SEQ ID NO 152
<211> LENGTH: 11
<212> TYPE: PRT
<213> ORGANISM: homo sapiens

<400> SEQUENCE: 152

Gly Arg Glu Glu Tyr Ser Ala Met Arg Asp Gln
1               5                   10

<210> SEQ ID NO 153
<211> LENGTH: 11
<212> TYPE: PRT
```

-continued

<213> ORGANISM: homo sapiens

<400> SEQUENCE: 153

Arg Glu Glu Tyr Ser Ala Met Arg Asp Gln Tyr
1               5                   10

<210> SEQ ID NO 154
<211> LENGTH: 21
<212> TYPE: PRT
<213> ORGANISM: homo sapiens

<400> SEQUENCE: 154

Thr Glu Tyr Lys Leu Val Val Val Gly Ala Val Gly Val Gly Lys Ser
1               5                   10                  15

Ala Leu Thr Ile Gln
            20

<210> SEQ ID NO 155
<211> LENGTH: 11
<212> TYPE: PRT
<213> ORGANISM: homo sapiens

<400> SEQUENCE: 155

Thr Glu Tyr Lys Leu Val Val Val Gly Ala Val
1               5                   10

<210> SEQ ID NO 156
<211> LENGTH: 11
<212> TYPE: PRT
<213> ORGANISM: homo sapiens

<400> SEQUENCE: 156

Glu Tyr Lys Leu Val Val Val Gly Ala Val Gly
1               5                   10

<210> SEQ ID NO 157
<211> LENGTH: 11
<212> TYPE: PRT
<213> ORGANISM: homo sapiens

<400> SEQUENCE: 157

Tyr Lys Leu Val Val Val Gly Ala Val Gly Val
1               5                   10

<210> SEQ ID NO 158
<211> LENGTH: 11
<212> TYPE: PRT
<213> ORGANISM: homo sapiens

<400> SEQUENCE: 158

Lys Leu Val Val Val Gly Ala Val Gly Val Gly
1               5                   10

<210> SEQ ID NO 159
<211> LENGTH: 11
<212> TYPE: PRT
<213> ORGANISM: homo sapiens

<400> SEQUENCE: 159

Leu Val Val Val Gly Ala Val Gly Val Gly Lys
1               5                   10

<210> SEQ ID NO 160
<211> LENGTH: 11

<212> TYPE: PRT
<213> ORGANISM: homo sapiens

<400> SEQUENCE: 160

Val Val Val Gly Ala Val Gly Val Gly Lys Ser
1               5                   10

<210> SEQ ID NO 161
<211> LENGTH: 11
<212> TYPE: PRT
<213> ORGANISM: homo sapiens

<400> SEQUENCE: 161

Val Val Gly Ala Val Gly Val Gly Lys Ser Ala
1               5                   10

<210> SEQ ID NO 162
<211> LENGTH: 11
<212> TYPE: PRT
<213> ORGANISM: homo sapiens

<400> SEQUENCE: 162

Val Gly Ala Val Gly Val Gly Lys Ser Ala Leu
1               5                   10

<210> SEQ ID NO 163
<211> LENGTH: 11
<212> TYPE: PRT
<213> ORGANISM: homo sapiens

<400> SEQUENCE: 163

Gly Ala Val Gly Val Gly Lys Ser Ala Leu Thr
1               5                   10

<210> SEQ ID NO 164
<211> LENGTH: 11
<212> TYPE: PRT
<213> ORGANISM: homo sapiens

<400> SEQUENCE: 164

Ala Val Gly Val Gly Lys Ser Ala Leu Thr Ile
1               5                   10

<210> SEQ ID NO 165
<211> LENGTH: 11
<212> TYPE: PRT
<213> ORGANISM: homo sapiens

<400> SEQUENCE: 165

Val Gly Val Gly Lys Ser Ala Leu Thr Ile Gln
1               5                   10

<210> SEQ ID NO 166
<211> LENGTH: 21
<212> TYPE: PRT
<213> ORGANISM: homo sapiens

<400> SEQUENCE: 166

Thr Glu Tyr Lys Leu Val Val Val Gly Ala Asp Gly Val Gly Lys Ser
1               5                   10                  15

Ala Leu Thr Ile Gln
            20

<210> SEQ ID NO 167

```
<211> LENGTH: 11
<212> TYPE: PRT
<213> ORGANISM: homo sapiens

<400> SEQUENCE: 167

Thr Glu Tyr Lys Leu Val Val Val Gly Ala Asp
1               5                   10

<210> SEQ ID NO 168
<211> LENGTH: 11
<212> TYPE: PRT
<213> ORGANISM: homo sapiens

<400> SEQUENCE: 168

Glu Tyr Lys Leu Val Val Val Gly Ala Asp Gly
1               5                   10

<210> SEQ ID NO 169
<211> LENGTH: 11
<212> TYPE: PRT
<213> ORGANISM: homo sapiens

<400> SEQUENCE: 169

Tyr Lys Leu Val Val Val Gly Ala Asp Gly Val
1               5                   10

<210> SEQ ID NO 170
<211> LENGTH: 11
<212> TYPE: PRT
<213> ORGANISM: homo sapiens

<400> SEQUENCE: 170

Lys Leu Val Val Val Gly Ala Asp Gly Val Gly
1               5                   10

<210> SEQ ID NO 171
<211> LENGTH: 11
<212> TYPE: PRT
<213> ORGANISM: homo sapiens

<400> SEQUENCE: 171

Leu Val Val Val Gly Ala Asp Gly Val Gly Lys
1               5                   10

<210> SEQ ID NO 172
<211> LENGTH: 11
<212> TYPE: PRT
<213> ORGANISM: homo sapiens

<400> SEQUENCE: 172

Val Val Val Gly Ala Asp Gly Val Gly Lys Ser
1               5                   10

<210> SEQ ID NO 173
<211> LENGTH: 11
<212> TYPE: PRT
<213> ORGANISM: homo sapiens

<400> SEQUENCE: 173

Val Val Gly Ala Asp Gly Val Gly Lys Ser Ala
1               5                   10

<210> SEQ ID NO 174
<211> LENGTH: 11
<212> TYPE: PRT
```

<213> ORGANISM: homo sapiens

<400> SEQUENCE: 174

Val Gly Ala Asp Gly Val Gly Lys Ser Ala Leu
1               5                   10

<210> SEQ ID NO 175
<211> LENGTH: 11
<212> TYPE: PRT
<213> ORGANISM: homo sapiens

<400> SEQUENCE: 175

Gly Ala Asp Gly Val Gly Lys Ser Ala Leu Thr
1               5                   10

<210> SEQ ID NO 176
<211> LENGTH: 11
<212> TYPE: PRT
<213> ORGANISM: homo sapiens

<400> SEQUENCE: 176

Ala Asp Gly Val Gly Lys Ser Ala Leu Thr Ile
1               5                   10

<210> SEQ ID NO 177
<211> LENGTH: 11
<212> TYPE: PRT
<213> ORGANISM: homo sapiens

<400> SEQUENCE: 177

Asp Gly Val Gly Lys Ser Ala Leu Thr Ile Gln
1               5                   10

<210> SEQ ID NO 178
<211> LENGTH: 21
<212> TYPE: PRT
<213> ORGANISM: homo sapiens

<400> SEQUENCE: 178

Asn Thr Phe Arg His Ser Val Val Val Pro Cys Glu Pro Pro Glu Val
1               5                   10                  15

Gly Ser Asp Cys Thr
            20

<210> SEQ ID NO 179
<211> LENGTH: 11
<212> TYPE: PRT
<213> ORGANISM: homo sapiens

<400> SEQUENCE: 179

Asn Thr Phe Arg His Ser Val Val Val Pro Cys
1               5                   10

<210> SEQ ID NO 180
<211> LENGTH: 11
<212> TYPE: PRT
<213> ORGANISM: homo sapiens

<400> SEQUENCE: 180

Thr Phe Arg His Ser Val Val Val Pro Cys Glu
1               5                   10

<210> SEQ ID NO 181
<211> LENGTH: 11

<212> TYPE: PRT
<213> ORGANISM: homo sapiens

<400> SEQUENCE: 181

Phe Arg His Ser Val Val Pro Cys Glu Pro
1               5                   10

<210> SEQ ID NO 182
<211> LENGTH: 11
<212> TYPE: PRT
<213> ORGANISM: homo sapiens

<400> SEQUENCE: 182

Arg His Ser Val Val Pro Cys Glu Pro Pro
1               5                   10

<210> SEQ ID NO 183
<211> LENGTH: 11
<212> TYPE: PRT
<213> ORGANISM: homo sapiens

<400> SEQUENCE: 183

His Ser Val Val Pro Cys Glu Pro Pro Glu
1               5                   10

<210> SEQ ID NO 184
<211> LENGTH: 11
<212> TYPE: PRT
<213> ORGANISM: homo sapiens

<400> SEQUENCE: 184

Ser Val Val Pro Cys Glu Pro Pro Glu Val
1               5                   10

<210> SEQ ID NO 185
<211> LENGTH: 11
<212> TYPE: PRT
<213> ORGANISM: homo sapiens

<400> SEQUENCE: 185

Val Val Val Pro Cys Glu Pro Pro Glu Val Gly
1               5                   10

<210> SEQ ID NO 186
<211> LENGTH: 11
<212> TYPE: PRT
<213> ORGANISM: homo sapiens

<400> SEQUENCE: 186

Val Val Pro Cys Glu Pro Pro Glu Val Gly Ser
1               5                   10

<210> SEQ ID NO 187
<211> LENGTH: 11
<212> TYPE: PRT
<213> ORGANISM: homo sapiens

<400> SEQUENCE: 187

Val Pro Cys Glu Pro Pro Glu Val Gly Ser Asp
1               5                   10

<210> SEQ ID NO 188
<211> LENGTH: 11
<212> TYPE: PRT
<213> ORGANISM: homo sapiens

```
<400> SEQUENCE: 188

Pro Cys Glu Pro Pro Glu Val Gly Ser Asp Cys
1               5                   10

<210> SEQ ID NO 189
<211> LENGTH: 11
<212> TYPE: PRT
<213> ORGANISM: homo sapiens

<400> SEQUENCE: 189

Cys Glu Pro Pro Glu Val Gly Ser Asp Cys Thr
1               5                   10

<210> SEQ ID NO 190
<211> LENGTH: 21
<212> TYPE: PRT
<213> ORGANISM: homo sapiens

<400> SEQUENCE: 190

Cys Asn Ser Ser Cys Met Gly Gly Met Asn Trp Arg Pro Ile Leu Thr
1               5                   10                  15

Ile Ile Thr Leu Glu
            20

<210> SEQ ID NO 191
<211> LENGTH: 11
<212> TYPE: PRT
<213> ORGANISM: homo sapiens

<400> SEQUENCE: 191

Cys Asn Ser Ser Cys Met Gly Gly Met Asn Trp
1               5                   10

<210> SEQ ID NO 192
<211> LENGTH: 11
<212> TYPE: PRT
<213> ORGANISM: homo sapiens

<400> SEQUENCE: 192

Asn Ser Ser Cys Met Gly Gly Met Asn Trp Arg
1               5                   10

<210> SEQ ID NO 193
<211> LENGTH: 11
<212> TYPE: PRT
<213> ORGANISM: homo sapiens

<400> SEQUENCE: 193

Ser Ser Cys Met Gly Gly Met Asn Trp Arg Pro
1               5                   10

<210> SEQ ID NO 194
<211> LENGTH: 11
<212> TYPE: PRT
<213> ORGANISM: homo sapiens

<400> SEQUENCE: 194

Ser Cys Met Gly Gly Met Asn Trp Arg Pro Ile
1               5                   10

<210> SEQ ID NO 195
<211> LENGTH: 11
<212> TYPE: PRT
```

<213> ORGANISM: homo sapiens

<400> SEQUENCE: 195

Cys Met Gly Gly Met Asn Trp Arg Pro Ile Leu
1               5                   10

<210> SEQ ID NO 196
<211> LENGTH: 11
<212> TYPE: PRT
<213> ORGANISM: homo sapiens

<400> SEQUENCE: 196

Met Gly Gly Met Asn Trp Arg Pro Ile Leu Thr
1               5                   10

<210> SEQ ID NO 197
<211> LENGTH: 11
<212> TYPE: PRT
<213> ORGANISM: homo sapiens

<400> SEQUENCE: 197

Gly Gly Met Asn Trp Arg Pro Ile Leu Thr Ile
1               5                   10

<210> SEQ ID NO 198
<211> LENGTH: 11
<212> TYPE: PRT
<213> ORGANISM: homo sapiens

<400> SEQUENCE: 198

Gly Met Asn Trp Arg Pro Ile Leu Thr Ile Ile
1               5                   10

<210> SEQ ID NO 199
<211> LENGTH: 11
<212> TYPE: PRT
<213> ORGANISM: homo sapiens

<400> SEQUENCE: 199

Met Asn Trp Arg Pro Ile Leu Thr Ile Ile Thr
1               5                   10

<210> SEQ ID NO 200
<211> LENGTH: 11
<212> TYPE: PRT
<213> ORGANISM: homo sapiens

<400> SEQUENCE: 200

Asn Trp Arg Pro Ile Leu Thr Ile Ile Thr Leu
1               5                   10

<210> SEQ ID NO 201
<211> LENGTH: 11
<212> TYPE: PRT
<213> ORGANISM: homo sapiens

<400> SEQUENCE: 201

Trp Arg Pro Ile Leu Thr Ile Ile Thr Leu Glu
1               5                   10

<210> SEQ ID NO 202
<211> LENGTH: 21
<212> TYPE: PRT
<213> ORGANISM: homo sapiens

```
<400> SEQUENCE: 202

Val Glu Tyr Leu Asp Asp Arg Asn Thr Phe Leu His Ser Val Val
1               5                   10                  15
Pro Tyr Glu Pro Pro
            20

<210> SEQ ID NO 203
<211> LENGTH: 11
<212> TYPE: PRT
<213> ORGANISM: homo sapiens

<400> SEQUENCE: 203

Val Glu Tyr Leu Asp Asp Arg Asn Thr Phe Leu
1               5                   10

<210> SEQ ID NO 204
<211> LENGTH: 11
<212> TYPE: PRT
<213> ORGANISM: homo sapiens

<400> SEQUENCE: 204

Glu Tyr Leu Asp Asp Arg Asn Thr Phe Leu His
1               5                   10

<210> SEQ ID NO 205
<211> LENGTH: 11
<212> TYPE: PRT
<213> ORGANISM: homo sapiens

<400> SEQUENCE: 205

Tyr Leu Asp Asp Arg Asn Thr Phe Leu His Ser
1               5                   10

<210> SEQ ID NO 206
<211> LENGTH: 11
<212> TYPE: PRT
<213> ORGANISM: homo sapiens

<400> SEQUENCE: 206

Leu Asp Asp Arg Asn Thr Phe Leu His Ser Val
1               5                   10

<210> SEQ ID NO 207
<211> LENGTH: 11
<212> TYPE: PRT
<213> ORGANISM: homo sapiens

<400> SEQUENCE: 207

Asp Asp Arg Asn Thr Phe Leu His Ser Val Val
1               5                   10

<210> SEQ ID NO 208
<211> LENGTH: 11
<212> TYPE: PRT
<213> ORGANISM: homo sapiens

<400> SEQUENCE: 208

Asp Arg Asn Thr Phe Leu His Ser Val Val Val
1               5                   10

<210> SEQ ID NO 209
<211> LENGTH: 11
<212> TYPE: PRT
```

<400> SEQUENCE: 209

Arg Asn Thr Phe Leu His Ser Val Val Val Pro
1               5                   10

<210> SEQ ID NO 210
<211> LENGTH: 11
<212> TYPE: PRT
<213> ORGANISM: homo sapiens

<400> SEQUENCE: 210

Asn Thr Phe Leu His Ser Val Val Val Pro Tyr
1               5                   10

<210> SEQ ID NO 211
<211> LENGTH: 11
<212> TYPE: PRT
<213> ORGANISM: homo sapiens

<400> SEQUENCE: 211

Thr Phe Leu His Ser Val Val Val Pro Tyr Glu
1               5                   10

<210> SEQ ID NO 212
<211> LENGTH: 11
<212> TYPE: PRT
<213> ORGANISM: homo sapiens

<400> SEQUENCE: 212

Phe Leu His Ser Val Val Val Pro Tyr Glu Pro
1               5                   10

<210> SEQ ID NO 213
<211> LENGTH: 11
<212> TYPE: PRT
<213> ORGANISM: homo sapiens

<400> SEQUENCE: 213

Leu His Ser Val Val Val Pro Tyr Glu Pro Pro
1               5                   10

<210> SEQ ID NO 214
<211> LENGTH: 21
<212> TYPE: PRT
<213> ORGANISM: homo sapiens

<400> SEQUENCE: 214

Lys Met Trp Lys Ser Pro Asn Gly Thr Ile Gln Asn Ile Leu Gly Gly
1               5                   10                  15

Thr Val Phe Arg Glu
            20

<210> SEQ ID NO 215
<211> LENGTH: 11
<212> TYPE: PRT
<213> ORGANISM: homo sapiens

<400> SEQUENCE: 215

Lys Met Trp Lys Ser Pro Asn Gly Thr Ile Gln
1               5                   10

<210> SEQ ID NO 216
<211> LENGTH: 11
<212> TYPE: PRT

<213> ORGANISM: homo sapiens

<400> SEQUENCE: 216

Met Trp Lys Ser Pro Asn Gly Thr Ile Gln Asn
1               5                   10

<210> SEQ ID NO 217
<211> LENGTH: 11
<212> TYPE: PRT
<213> ORGANISM: homo sapiens

<400> SEQUENCE: 217

Trp Lys Ser Pro Asn Gly Thr Ile Gln Asn Ile
1               5                   10

<210> SEQ ID NO 218
<211> LENGTH: 11
<212> TYPE: PRT
<213> ORGANISM: homo sapiens

<400> SEQUENCE: 218

Lys Ser Pro Asn Gly Thr Ile Gln Asn Ile Leu
1               5                   10

<210> SEQ ID NO 219
<211> LENGTH: 11
<212> TYPE: PRT
<213> ORGANISM: homo sapiens

<400> SEQUENCE: 219

Ser Pro Asn Gly Thr Ile Gln Asn Ile Leu Gly
1               5                   10

<210> SEQ ID NO 220
<211> LENGTH: 11
<212> TYPE: PRT
<213> ORGANISM: homo sapiens

<400> SEQUENCE: 220

Pro Asn Gly Thr Ile Gln Asn Ile Leu Gly Gly
1               5                   10

<210> SEQ ID NO 221
<211> LENGTH: 11
<212> TYPE: PRT
<213> ORGANISM: homo sapiens

<400> SEQUENCE: 221

Asn Gly Thr Ile Gln Asn Ile Leu Gly Gly Thr
1               5                   10

<210> SEQ ID NO 222
<211> LENGTH: 11
<212> TYPE: PRT
<213> ORGANISM: homo sapiens

<400> SEQUENCE: 222

Gly Thr Ile Gln Asn Ile Leu Gly Gly Thr Val
1               5                   10

<210> SEQ ID NO 223
<211> LENGTH: 11
<212> TYPE: PRT
<213> ORGANISM: homo sapiens

```
<400> SEQUENCE: 223

Thr Ile Gln Asn Ile Leu Gly Gly Thr Val Phe
1               5                   10

<210> SEQ ID NO 224
<211> LENGTH: 11
<212> TYPE: PRT
<213> ORGANISM: homo sapiens

<400> SEQUENCE: 224

Ile Gln Asn Ile Leu Gly Gly Thr Val Phe Arg
1               5                   10

<210> SEQ ID NO 225
<211> LENGTH: 11
<212> TYPE: PRT
<213> ORGANISM: homo sapiens

<400> SEQUENCE: 225

Gln Asn Ile Leu Gly Gly Thr Val Phe Arg Glu
1               5                   10

<210> SEQ ID NO 226
<211> LENGTH: 19
<212> TYPE: PRT
<213> ORGANISM: homo sapiens

<400> SEQUENCE: 226

Leu Leu Asp Ile Leu Asp Thr Ala Gly His Glu Glu Tyr Ser Ala Met
1               5                   10                  15

Arg Asp Gln

<210> SEQ ID NO 227
<211> LENGTH: 10
<212> TYPE: PRT
<213> ORGANISM: homo sapiens

<400> SEQUENCE: 227

Leu Leu Asp Ile Leu Asp Thr Ala Gly His
1               5                   10

<210> SEQ ID NO 228
<211> LENGTH: 10
<212> TYPE: PRT
<213> ORGANISM: homo sapiens

<400> SEQUENCE: 228

Leu Asp Ile Leu Asp Thr Ala Gly His Glu
1               5                   10

<210> SEQ ID NO 229
<211> LENGTH: 10
<212> TYPE: PRT
<213> ORGANISM: homo sapiens

<400> SEQUENCE: 229

Asp Ile Leu Asp Thr Ala Gly His Glu Glu
1               5                   10

<210> SEQ ID NO 230
<211> LENGTH: 10
<212> TYPE: PRT
<213> ORGANISM: homo sapiens
```

```
<400> SEQUENCE: 230

Ile Leu Asp Thr Ala Gly His Glu Glu Tyr
1               5                   10

<210> SEQ ID NO 231
<211> LENGTH: 10
<212> TYPE: PRT
<213> ORGANISM: homo sapiens

<400> SEQUENCE: 231

Leu Asp Thr Ala Gly His Glu Glu Tyr Ser
1               5                   10

<210> SEQ ID NO 232
<211> LENGTH: 10
<212> TYPE: PRT
<213> ORGANISM: homo sapiens

<400> SEQUENCE: 232

Asp Thr Ala Gly His Glu Glu Tyr Ser Ala
1               5                   10

<210> SEQ ID NO 233
<211> LENGTH: 10
<212> TYPE: PRT
<213> ORGANISM: homo sapiens

<400> SEQUENCE: 233

Thr Ala Gly His Glu Glu Tyr Ser Ala Met
1               5                   10

<210> SEQ ID NO 234
<211> LENGTH: 10
<212> TYPE: PRT
<213> ORGANISM: homo sapiens

<400> SEQUENCE: 234

Ala Gly His Glu Glu Tyr Ser Ala Met Arg
1               5                   10

<210> SEQ ID NO 235
<211> LENGTH: 10
<212> TYPE: PRT
<213> ORGANISM: homo sapiens

<400> SEQUENCE: 235

Gly His Glu Glu Tyr Ser Ala Met Arg Asp
1               5                   10

<210> SEQ ID NO 236
<211> LENGTH: 10
<212> TYPE: PRT
<213> ORGANISM: homo sapiens

<400> SEQUENCE: 236

His Glu Glu Tyr Ser Ala Met Arg Asp Gln
1               5                   10

<210> SEQ ID NO 237
<211> LENGTH: 19
<212> TYPE: PRT
<213> ORGANISM: homo sapiens

<400> SEQUENCE: 237
```

Leu Leu Asp Ile Leu Asp Thr Ala Gly Leu Glu Glu Tyr Ser Ala Met
1               5                   10                  15

Arg Asp Gln

<210> SEQ ID NO 238
<211> LENGTH: 10
<212> TYPE: PRT
<213> ORGANISM: homo sapiens

<400> SEQUENCE: 238

Leu Leu Asp Ile Leu Asp Thr Ala Gly Leu
1               5                   10

<210> SEQ ID NO 239
<211> LENGTH: 10
<212> TYPE: PRT
<213> ORGANISM: homo sapiens

<400> SEQUENCE: 239

Leu Asp Ile Leu Asp Thr Ala Gly Leu Glu
1               5                   10

<210> SEQ ID NO 240
<211> LENGTH: 10
<212> TYPE: PRT
<213> ORGANISM: homo sapiens

<400> SEQUENCE: 240

Asp Ile Leu Asp Thr Ala Gly Leu Glu Glu
1               5                   10

<210> SEQ ID NO 241
<211> LENGTH: 10
<212> TYPE: PRT
<213> ORGANISM: homo sapiens

<400> SEQUENCE: 241

Ile Leu Asp Thr Ala Gly Leu Glu Glu Tyr
1               5                   10

<210> SEQ ID NO 242
<211> LENGTH: 10
<212> TYPE: PRT
<213> ORGANISM: homo sapiens

<400> SEQUENCE: 242

Leu Asp Thr Ala Gly Leu Glu Glu Tyr Ser
1               5                   10

<210> SEQ ID NO 243
<211> LENGTH: 10
<212> TYPE: PRT
<213> ORGANISM: homo sapiens

<400> SEQUENCE: 243

Asp Thr Ala Gly Leu Glu Glu Tyr Ser Ala
1               5                   10

<210> SEQ ID NO 244
<211> LENGTH: 10
<212> TYPE: PRT
<213> ORGANISM: homo sapiens

<400> SEQUENCE: 244

```
Thr Ala Gly Leu Glu Glu Tyr Ser Ala Met
1               5                   10
```

<210> SEQ ID NO 245
<211> LENGTH: 10
<212> TYPE: PRT
<213> ORGANISM: homo sapiens

<400> SEQUENCE: 245

```
Ala Gly Leu Glu Glu Tyr Ser Ala Met Arg
1               5                   10
```

<210> SEQ ID NO 246
<211> LENGTH: 10
<212> TYPE: PRT
<213> ORGANISM: homo sapiens

<400> SEQUENCE: 246

```
Gly Leu Glu Glu Tyr Ser Ala Met Arg Asp
1               5                   10
```

<210> SEQ ID NO 247
<211> LENGTH: 10
<212> TYPE: PRT
<213> ORGANISM: homo sapiens

<400> SEQUENCE: 247

```
Leu Glu Glu Tyr Ser Ala Met Arg Asp Gln
1               5                   10
```

<210> SEQ ID NO 248
<211> LENGTH: 19
<212> TYPE: PRT
<213> ORGANISM: homo sapiens

<400> SEQUENCE: 248

```
Leu Leu Asp Ile Leu Asp Thr Ala Gly Arg Glu Glu Tyr Ser Ala Met
1               5                   10                  15

Arg Asp Gln
```

<210> SEQ ID NO 249
<211> LENGTH: 10
<212> TYPE: PRT
<213> ORGANISM: homo sapiens

<400> SEQUENCE: 249

```
Leu Leu Asp Ile Leu Asp Thr Ala Gly Arg
1               5                   10
```

<210> SEQ ID NO 250
<211> LENGTH: 10
<212> TYPE: PRT
<213> ORGANISM: homo sapiens

<400> SEQUENCE: 250

```
Leu Asp Ile Leu Asp Thr Ala Gly Arg Glu
1               5                   10
```

<210> SEQ ID NO 251
<211> LENGTH: 10
<212> TYPE: PRT
<213> ORGANISM: homo sapiens

<400> SEQUENCE: 251

Asp Ile Leu Asp Thr Ala Gly Arg Glu Glu
1               5                   10

<210> SEQ ID NO 252
<211> LENGTH: 10
<212> TYPE: PRT
<213> ORGANISM: homo sapiens

<400> SEQUENCE: 252

Ile Leu Asp Thr Ala Gly Arg Glu Glu Tyr
1               5                   10

<210> SEQ ID NO 253
<211> LENGTH: 10
<212> TYPE: PRT
<213> ORGANISM: homo sapiens

<400> SEQUENCE: 253

Leu Asp Thr Ala Gly Arg Glu Glu Tyr Ser
1               5                   10

<210> SEQ ID NO 254
<211> LENGTH: 10
<212> TYPE: PRT
<213> ORGANISM: homo sapiens

<400> SEQUENCE: 254

Asp Thr Ala Gly Arg Glu Glu Tyr Ser Ala
1               5                   10

<210> SEQ ID NO 255
<211> LENGTH: 10
<212> TYPE: PRT
<213> ORGANISM: homo sapiens

<400> SEQUENCE: 255

Thr Ala Gly Arg Glu Glu Tyr Ser Ala Met
1               5                   10

<210> SEQ ID NO 256
<211> LENGTH: 10
<212> TYPE: PRT
<213> ORGANISM: homo sapiens

<400> SEQUENCE: 256

Ala Gly Arg Glu Glu Tyr Ser Ala Met Arg
1               5                   10

<210> SEQ ID NO 257
<211> LENGTH: 10
<212> TYPE: PRT
<213> ORGANISM: homo sapiens

<400> SEQUENCE: 257

Gly Arg Glu Glu Tyr Ser Ala Met Arg Asp
1               5                   10

<210> SEQ ID NO 258
<211> LENGTH: 10
<212> TYPE: PRT
<213> ORGANISM: homo sapiens

<400> SEQUENCE: 258

Arg Glu Glu Tyr Ser Ala Met Arg Asp Gln
1               5                   10

<210> SEQ ID NO 259
<211> LENGTH: 19
<212> TYPE: PRT
<213> ORGANISM: homo sapiens

<400> SEQUENCE: 259

Glu Tyr Lys Leu Val Val Val Gly Ala Val Gly Val Gly Lys Ser Ala
1               5                   10                  15
Leu Thr Ile

<210> SEQ ID NO 260
<211> LENGTH: 10
<212> TYPE: PRT
<213> ORGANISM: homo sapiens

<400> SEQUENCE: 260

Glu Tyr Lys Leu Val Val Val Gly Ala Val
1               5                   10

<210> SEQ ID NO 261
<211> LENGTH: 10
<212> TYPE: PRT
<213> ORGANISM: homo sapiens

<400> SEQUENCE: 261

Tyr Lys Leu Val Val Val Gly Ala Val Gly
1               5                   10

<210> SEQ ID NO 262
<211> LENGTH: 10
<212> TYPE: PRT
<213> ORGANISM: homo sapiens

<400> SEQUENCE: 262

Lys Leu Val Val Val Gly Ala Val Gly Val
1               5                   10

<210> SEQ ID NO 263
<211> LENGTH: 10
<212> TYPE: PRT
<213> ORGANISM: homo sapiens

<400> SEQUENCE: 263

Leu Val Val Val Gly Ala Val Gly Val Gly
1               5                   10

<210> SEQ ID NO 264
<211> LENGTH: 10
<212> TYPE: PRT
<213> ORGANISM: homo sapiens

<400> SEQUENCE: 264

Val Val Val Gly Ala Val Gly Val Gly Lys
1               5                   10

<210> SEQ ID NO 265
<211> LENGTH: 10
<212> TYPE: PRT
<213> ORGANISM: homo sapiens

<400> SEQUENCE: 265

Val Val Gly Ala Val Gly Val Gly Lys Ser
1               5                   10

```
<210> SEQ ID NO 266
<211> LENGTH: 10
<212> TYPE: PRT
<213> ORGANISM: homo sapiens

<400> SEQUENCE: 266

Val Gly Ala Val Gly Val Gly Lys Ser Ala
1               5                   10

<210> SEQ ID NO 267
<211> LENGTH: 10
<212> TYPE: PRT
<213> ORGANISM: homo sapiens

<400> SEQUENCE: 267

Gly Ala Val Gly Val Gly Lys Ser Ala Leu
1               5                   10

<210> SEQ ID NO 268
<211> LENGTH: 10
<212> TYPE: PRT
<213> ORGANISM: homo sapiens

<400> SEQUENCE: 268

Ala Val Gly Val Gly Lys Ser Ala Leu Thr
1               5                   10

<210> SEQ ID NO 269
<211> LENGTH: 10
<212> TYPE: PRT
<213> ORGANISM: homo sapiens

<400> SEQUENCE: 269

Val Gly Val Gly Lys Ser Ala Leu Thr Ile
1               5                   10

<210> SEQ ID NO 270
<211> LENGTH: 19
<212> TYPE: PRT
<213> ORGANISM: homo sapiens

<400> SEQUENCE: 270

Glu Tyr Lys Leu Val Val Val Gly Ala Asp Gly Val Gly Lys Ser Ala
1               5                   10                  15

Leu Thr Ile

<210> SEQ ID NO 271
<211> LENGTH: 10
<212> TYPE: PRT
<213> ORGANISM: homo sapiens

<400> SEQUENCE: 271

Glu Tyr Lys Leu Val Val Val Gly Ala Asp
1               5                   10

<210> SEQ ID NO 272
<211> LENGTH: 10
<212> TYPE: PRT
<213> ORGANISM: homo sapiens

<400> SEQUENCE: 272

Tyr Lys Leu Val Val Val Gly Ala Asp Gly
1               5                   10
```

```
<210> SEQ ID NO 273
<211> LENGTH: 10
<212> TYPE: PRT
<213> ORGANISM: homo sapiens

<400> SEQUENCE: 273

Lys Leu Val Val Val Gly Ala Asp Gly Val
1               5                   10

<210> SEQ ID NO 274
<211> LENGTH: 10
<212> TYPE: PRT
<213> ORGANISM: homo sapiens

<400> SEQUENCE: 274

Leu Val Val Val Gly Ala Asp Gly Val Gly
1               5                   10

<210> SEQ ID NO 275
<211> LENGTH: 10
<212> TYPE: PRT
<213> ORGANISM: homo sapiens

<400> SEQUENCE: 275

Val Val Val Gly Ala Asp Gly Val Gly Lys
1               5                   10

<210> SEQ ID NO 276
<211> LENGTH: 10
<212> TYPE: PRT
<213> ORGANISM: homo sapiens

<400> SEQUENCE: 276

Val Val Gly Ala Asp Gly Val Gly Lys Ser
1               5                   10

<210> SEQ ID NO 277
<211> LENGTH: 10
<212> TYPE: PRT
<213> ORGANISM: homo sapiens

<400> SEQUENCE: 277

Val Gly Ala Asp Gly Val Gly Lys Ser Ala
1               5                   10

<210> SEQ ID NO 278
<211> LENGTH: 10
<212> TYPE: PRT
<213> ORGANISM: homo sapiens

<400> SEQUENCE: 278

Gly Ala Asp Gly Val Gly Lys Ser Ala Leu
1               5                   10

<210> SEQ ID NO 279
<211> LENGTH: 10
<212> TYPE: PRT
<213> ORGANISM: homo sapiens

<400> SEQUENCE: 279

Ala Asp Gly Val Gly Lys Ser Ala Leu Thr
1               5                   10
```

```
<210> SEQ ID NO 280
<211> LENGTH: 10
<212> TYPE: PRT
<213> ORGANISM: homo sapiens

<400> SEQUENCE: 280

Asp Gly Val Gly Lys Ser Ala Leu Thr Ile
1               5                   10

<210> SEQ ID NO 281
<211> LENGTH: 19
<212> TYPE: PRT
<213> ORGANISM: homo sapiens

<400> SEQUENCE: 281

Thr Phe Arg His Ser Val Val Val Pro Cys Glu Pro Pro Glu Val Gly
1               5                   10                  15

Ser Asp Cys

<210> SEQ ID NO 282
<211> LENGTH: 10
<212> TYPE: PRT
<213> ORGANISM: homo sapiens

<400> SEQUENCE: 282

Thr Phe Arg His Ser Val Val Val Pro Cys
1               5                   10

<210> SEQ ID NO 283
<211> LENGTH: 10
<212> TYPE: PRT
<213> ORGANISM: homo sapiens

<400> SEQUENCE: 283

Phe Arg His Ser Val Val Val Pro Cys Glu
1               5                   10

<210> SEQ ID NO 284
<211> LENGTH: 10
<212> TYPE: PRT
<213> ORGANISM: homo sapiens

<400> SEQUENCE: 284

Arg His Ser Val Val Val Pro Cys Glu Pro
1               5                   10

<210> SEQ ID NO 285
<211> LENGTH: 10
<212> TYPE: PRT
<213> ORGANISM: homo sapiens

<400> SEQUENCE: 285

His Ser Val Val Val Pro Cys Glu Pro Pro
1               5                   10

<210> SEQ ID NO 286
<211> LENGTH: 10
<212> TYPE: PRT
<213> ORGANISM: homo sapiens

<400> SEQUENCE: 286

Ser Val Val Val Pro Cys Glu Pro Pro Glu
1               5                   10
```

```
<210> SEQ ID NO 287
<211> LENGTH: 10
<212> TYPE: PRT
<213> ORGANISM: homo sapiens

<400> SEQUENCE: 287

Val Val Val Pro Cys Glu Pro Pro Glu Val
1               5                   10

<210> SEQ ID NO 288
<211> LENGTH: 10
<212> TYPE: PRT
<213> ORGANISM: homo sapiens

<400> SEQUENCE: 288

Val Val Pro Cys Glu Pro Pro Glu Val Gly
1               5                   10

<210> SEQ ID NO 289
<211> LENGTH: 10
<212> TYPE: PRT
<213> ORGANISM: homo sapiens

<400> SEQUENCE: 289

Val Pro Cys Glu Pro Pro Glu Val Gly Ser
1               5                   10

<210> SEQ ID NO 290
<211> LENGTH: 10
<212> TYPE: PRT
<213> ORGANISM: homo sapiens

<400> SEQUENCE: 290

Pro Cys Glu Pro Pro Glu Val Gly Ser Asp
1               5                   10

<210> SEQ ID NO 291
<211> LENGTH: 10
<212> TYPE: PRT
<213> ORGANISM: homo sapiens

<400> SEQUENCE: 291

Cys Glu Pro Pro Glu Val Gly Ser Asp Cys
1               5                   10

<210> SEQ ID NO 292
<211> LENGTH: 19
<212> TYPE: PRT
<213> ORGANISM: homo sapiens

<400> SEQUENCE: 292

Asn Ser Ser Cys Met Gly Gly Met Asn Trp Arg Pro Ile Leu Thr Ile
1               5                   10                  15

Ile Thr Leu

<210> SEQ ID NO 293
<211> LENGTH: 10
<212> TYPE: PRT
<213> ORGANISM: homo sapiens

<400> SEQUENCE: 293

Asn Ser Ser Cys Met Gly Gly Met Asn Trp
1               5                   10
```

<210> SEQ ID NO 294
<211> LENGTH: 10
<212> TYPE: PRT
<213> ORGANISM: homo sapiens

<400> SEQUENCE: 294

Ser Ser Cys Met Gly Gly Met Asn Trp Arg
1               5                   10

<210> SEQ ID NO 295
<211> LENGTH: 10
<212> TYPE: PRT
<213> ORGANISM: homo sapiens

<400> SEQUENCE: 295

Ser Cys Met Gly Gly Met Asn Trp Arg Pro
1               5                   10

<210> SEQ ID NO 296
<211> LENGTH: 10
<212> TYPE: PRT
<213> ORGANISM: homo sapiens

<400> SEQUENCE: 296

Cys Met Gly Gly Met Asn Trp Arg Pro Ile
1               5                   10

<210> SEQ ID NO 297
<211> LENGTH: 10
<212> TYPE: PRT
<213> ORGANISM: homo sapiens

<400> SEQUENCE: 297

Met Gly Gly Met Asn Trp Arg Pro Ile Leu
1               5                   10

<210> SEQ ID NO 298
<211> LENGTH: 10
<212> TYPE: PRT
<213> ORGANISM: homo sapiens

<400> SEQUENCE: 298

Gly Gly Met Asn Trp Arg Pro Ile Leu Thr
1               5                   10

<210> SEQ ID NO 299
<211> LENGTH: 10
<212> TYPE: PRT
<213> ORGANISM: homo sapiens

<400> SEQUENCE: 299

Gly Met Asn Trp Arg Pro Ile Leu Thr Ile
1               5                   10

<210> SEQ ID NO 300
<211> LENGTH: 10
<212> TYPE: PRT
<213> ORGANISM: homo sapiens

<400> SEQUENCE: 300

Met Asn Trp Arg Pro Ile Leu Thr Ile Ile
1               5                   10

<210> SEQ ID NO 301
<211> LENGTH: 10

```
<212> TYPE: PRT
<213> ORGANISM: homo sapiens

<400> SEQUENCE: 301

Asn Trp Arg Pro Ile Leu Thr Ile Ile Thr
1               5                   10

<210> SEQ ID NO 302
<211> LENGTH: 10
<212> TYPE: PRT
<213> ORGANISM: homo sapiens

<400> SEQUENCE: 302

Trp Arg Pro Ile Leu Thr Ile Ile Thr Leu
1               5                   10

<210> SEQ ID NO 303
<211> LENGTH: 19
<212> TYPE: PRT
<213> ORGANISM: homo sapiens

<400> SEQUENCE: 303

Glu Tyr Leu Asp Asp Arg Asn Thr Phe Leu His Ser Val Val Val Pro
1               5                   10                  15

Tyr Glu Pro

<210> SEQ ID NO 304
<211> LENGTH: 10
<212> TYPE: PRT
<213> ORGANISM: homo sapiens

<400> SEQUENCE: 304

Glu Tyr Leu Asp Asp Arg Asn Thr Phe Leu
1               5                   10

<210> SEQ ID NO 305
<211> LENGTH: 10
<212> TYPE: PRT
<213> ORGANISM: homo sapiens

<400> SEQUENCE: 305

Tyr Leu Asp Asp Arg Asn Thr Phe Leu His
1               5                   10

<210> SEQ ID NO 306
<211> LENGTH: 10
<212> TYPE: PRT
<213> ORGANISM: homo sapiens

<400> SEQUENCE: 306

Leu Asp Asp Arg Asn Thr Phe Leu His Ser
1               5                   10

<210> SEQ ID NO 307
<211> LENGTH: 10
<212> TYPE: PRT
<213> ORGANISM: homo sapiens

<400> SEQUENCE: 307

Asp Asp Arg Asn Thr Phe Leu His Ser Val
1               5                   10

<210> SEQ ID NO 308
<211> LENGTH: 10
```

-continued

```
<212> TYPE: PRT
<213> ORGANISM: homo sapiens

<400> SEQUENCE: 308

Asp Arg Asn Thr Phe Leu His Ser Val Val
1               5                   10

<210> SEQ ID NO 309
<211> LENGTH: 10
<212> TYPE: PRT
<213> ORGANISM: homo sapiens

<400> SEQUENCE: 309

Arg Asn Thr Phe Leu His Ser Val Val Val
1               5                   10

<210> SEQ ID NO 310
<211> LENGTH: 10
<212> TYPE: PRT
<213> ORGANISM: homo sapiens

<400> SEQUENCE: 310

Asn Thr Phe Leu His Ser Val Val Val Pro
1               5                   10

<210> SEQ ID NO 311
<211> LENGTH: 10
<212> TYPE: PRT
<213> ORGANISM: homo sapiens

<400> SEQUENCE: 311

Thr Phe Leu His Ser Val Val Val Pro Tyr
1               5                   10

<210> SEQ ID NO 312
<211> LENGTH: 10
<212> TYPE: PRT
<213> ORGANISM: homo sapiens

<400> SEQUENCE: 312

Phe Leu His Ser Val Val Val Pro Tyr Glu
1               5                   10

<210> SEQ ID NO 313
<211> LENGTH: 10
<212> TYPE: PRT
<213> ORGANISM: homo sapiens

<400> SEQUENCE: 313

Leu His Ser Val Val Val Pro Tyr Glu Pro
1               5                   10

<210> SEQ ID NO 314
<211> LENGTH: 19
<212> TYPE: PRT
<213> ORGANISM: homo sapiens

<400> SEQUENCE: 314

Met Trp Lys Ser Pro Asn Gly Thr Ile Gln Asn Ile Leu Gly Gly Thr
1               5                   10                  15

Val Phe Arg

<210> SEQ ID NO 315
<211> LENGTH: 10
```

<212> TYPE: PRT
<213> ORGANISM: homo sapiens

<400> SEQUENCE: 315

Met Trp Lys Ser Pro Asn Gly Thr Ile Gln
1               5                   10

<210> SEQ ID NO 316
<211> LENGTH: 10
<212> TYPE: PRT
<213> ORGANISM: homo sapiens

<400> SEQUENCE: 316

Trp Lys Ser Pro Asn Gly Thr Ile Gln Asn
1               5                   10

<210> SEQ ID NO 317
<211> LENGTH: 10
<212> TYPE: PRT
<213> ORGANISM: homo sapiens

<400> SEQUENCE: 317

Lys Ser Pro Asn Gly Thr Ile Gln Asn Ile
1               5                   10

<210> SEQ ID NO 318
<211> LENGTH: 10
<212> TYPE: PRT
<213> ORGANISM: homo sapiens

<400> SEQUENCE: 318

Ser Pro Asn Gly Thr Ile Gln Asn Ile Leu
1               5                   10

<210> SEQ ID NO 319
<211> LENGTH: 10
<212> TYPE: PRT
<213> ORGANISM: homo sapiens

<400> SEQUENCE: 319

Pro Asn Gly Thr Ile Gln Asn Ile Leu Gly
1               5                   10

<210> SEQ ID NO 320
<211> LENGTH: 10
<212> TYPE: PRT
<213> ORGANISM: homo sapiens

<400> SEQUENCE: 320

Asn Gly Thr Ile Gln Asn Ile Leu Gly Gly
1               5                   10

<210> SEQ ID NO 321
<211> LENGTH: 10
<212> TYPE: PRT
<213> ORGANISM: homo sapiens

<400> SEQUENCE: 321

Gly Thr Ile Gln Asn Ile Leu Gly Gly Thr
1               5                   10

<210> SEQ ID NO 322
<211> LENGTH: 10
<212> TYPE: PRT
<213> ORGANISM: homo sapiens

<400> SEQUENCE: 322

Thr Ile Gln Asn Ile Leu Gly Gly Thr Val
1               5                   10

<210> SEQ ID NO 323
<211> LENGTH: 10
<212> TYPE: PRT
<213> ORGANISM: homo sapiens

<400> SEQUENCE: 323

Ile Gln Asn Ile Leu Gly Gly Thr Val Phe
1               5                   10

<210> SEQ ID NO 324
<211> LENGTH: 10
<212> TYPE: PRT
<213> ORGANISM: homo sapiens

<400> SEQUENCE: 324

Gln Asn Ile Leu Gly Gly Thr Val Phe Arg
1               5                   10

<210> SEQ ID NO 325
<211> LENGTH: 17
<212> TYPE: PRT
<213> ORGANISM: homo sapiens

<400> SEQUENCE: 325

Leu Asp Ile Leu Asp Thr Ala Gly His Glu Glu Tyr Ser Ala Met Arg
1               5                   10                  15

Asp

<210> SEQ ID NO 326
<211> LENGTH: 9
<212> TYPE: PRT
<213> ORGANISM: homo sapiens

<400> SEQUENCE: 326

Leu Asp Ile Leu Asp Thr Ala Gly His
1               5

<210> SEQ ID NO 327
<211> LENGTH: 9
<212> TYPE: PRT
<213> ORGANISM: homo sapiens

<400> SEQUENCE: 327

Asp Ile Leu Asp Thr Ala Gly His Glu
1               5

<210> SEQ ID NO 328
<211> LENGTH: 9
<212> TYPE: PRT
<213> ORGANISM: homo sapiens

<400> SEQUENCE: 328

Ile Leu Asp Thr Ala Gly His Glu Glu
1               5

<210> SEQ ID NO 329
<211> LENGTH: 9
<212> TYPE: PRT
<213> ORGANISM: homo sapiens

<400> SEQUENCE: 329

Leu Asp Thr Ala Gly His Glu Glu Tyr
1               5

<210> SEQ ID NO 330
<211> LENGTH: 9
<212> TYPE: PRT
<213> ORGANISM: homo sapiens

<400> SEQUENCE: 330

Asp Thr Ala Gly His Glu Glu Tyr Ser
1               5

<210> SEQ ID NO 331
<211> LENGTH: 9
<212> TYPE: PRT
<213> ORGANISM: homo sapiens

<400> SEQUENCE: 331

Thr Ala Gly His Glu Glu Tyr Ser Ala
1               5

<210> SEQ ID NO 332
<211> LENGTH: 9
<212> TYPE: PRT
<213> ORGANISM: homo sapiens

<400> SEQUENCE: 332

Ala Gly His Glu Glu Tyr Ser Ala Met
1               5

<210> SEQ ID NO 333
<211> LENGTH: 9
<212> TYPE: PRT
<213> ORGANISM: homo sapiens

<400> SEQUENCE: 333

Gly His Glu Glu Tyr Ser Ala Met Arg
1               5

<210> SEQ ID NO 334
<211> LENGTH: 9
<212> TYPE: PRT
<213> ORGANISM: homo sapiens

<400> SEQUENCE: 334

His Glu Glu Tyr Ser Ala Met Arg Asp
1               5

<210> SEQ ID NO 335
<211> LENGTH: 17
<212> TYPE: PRT
<213> ORGANISM: homo sapiens

<400> SEQUENCE: 335

Leu Asp Ile Leu Asp Thr Ala Gly Leu Glu Glu Tyr Ser Ala Met Arg
1               5                   10                  15

Asp

<210> SEQ ID NO 336
<211> LENGTH: 9
<212> TYPE: PRT
<213> ORGANISM: homo sapiens

<400> SEQUENCE: 336

Leu Asp Ile Leu Asp Thr Ala Gly Leu
1               5

<210> SEQ ID NO 337
<211> LENGTH: 9
<212> TYPE: PRT
<213> ORGANISM: homo sapiens

<400> SEQUENCE: 337

Asp Ile Leu Asp Thr Ala Gly Leu Glu
1               5

<210> SEQ ID NO 338
<211> LENGTH: 9
<212> TYPE: PRT
<213> ORGANISM: homo sapiens

<400> SEQUENCE: 338

Ile Leu Asp Thr Ala Gly Leu Glu Glu
1               5

<210> SEQ ID NO 339
<211> LENGTH: 9
<212> TYPE: PRT
<213> ORGANISM: homo sapiens

<400> SEQUENCE: 339

Leu Asp Thr Ala Gly Leu Glu Glu Tyr
1               5

<210> SEQ ID NO 340
<211> LENGTH: 9
<212> TYPE: PRT
<213> ORGANISM: homo sapiens

<400> SEQUENCE: 340

Asp Thr Ala Gly Leu Glu Glu Tyr Ser
1               5

<210> SEQ ID NO 341
<211> LENGTH: 9
<212> TYPE: PRT
<213> ORGANISM: homo sapiens

<400> SEQUENCE: 341

Thr Ala Gly Leu Glu Glu Tyr Ser Ala
1               5

<210> SEQ ID NO 342
<211> LENGTH: 9
<212> TYPE: PRT
<213> ORGANISM: homo sapiens

<400> SEQUENCE: 342

Ala Gly Leu Glu Glu Tyr Ser Ala Met
1               5

<210> SEQ ID NO 343
<211> LENGTH: 9
<212> TYPE: PRT
<213> ORGANISM: homo sapiens

<400> SEQUENCE: 343

```
Gly Leu Glu Glu Tyr Ser Ala Met Arg
1               5

<210> SEQ ID NO 344
<211> LENGTH: 9
<212> TYPE: PRT
<213> ORGANISM: homo sapiens

<400> SEQUENCE: 344

Leu Glu Glu Tyr Ser Ala Met Arg Asp
1               5

<210> SEQ ID NO 345
<211> LENGTH: 17
<212> TYPE: PRT
<213> ORGANISM: homo sapiens

<400> SEQUENCE: 345

Leu Asp Ile Leu Asp Thr Ala Gly Arg Glu Glu Tyr Ser Ala Met Arg
1               5                   10                  15

Asp

<210> SEQ ID NO 346
<211> LENGTH: 9
<212> TYPE: PRT
<213> ORGANISM: homo sapiens

<400> SEQUENCE: 346

Leu Asp Ile Leu Asp Thr Ala Gly Arg
1               5

<210> SEQ ID NO 347
<211> LENGTH: 9
<212> TYPE: PRT
<213> ORGANISM: homo sapiens

<400> SEQUENCE: 347

Asp Ile Leu Asp Thr Ala Gly Arg Glu
1               5

<210> SEQ ID NO 348
<211> LENGTH: 9
<212> TYPE: PRT
<213> ORGANISM: homo sapiens

<400> SEQUENCE: 348

Ile Leu Asp Thr Ala Gly Arg Glu Glu
1               5

<210> SEQ ID NO 349
<211> LENGTH: 9
<212> TYPE: PRT
<213> ORGANISM: homo sapiens

<400> SEQUENCE: 349

Leu Asp Thr Ala Gly Arg Glu Glu Tyr
1               5

<210> SEQ ID NO 350
<211> LENGTH: 9
<212> TYPE: PRT
<213> ORGANISM: homo sapiens

<400> SEQUENCE: 350
```

Asp Thr Ala Gly Arg Glu Glu Tyr Ser
1               5

<210> SEQ ID NO 351
<211> LENGTH: 9
<212> TYPE: PRT
<213> ORGANISM: homo sapiens

<400> SEQUENCE: 351

Thr Ala Gly Arg Glu Glu Tyr Ser Ala
1               5

<210> SEQ ID NO 352
<211> LENGTH: 9
<212> TYPE: PRT
<213> ORGANISM: homo sapiens

<400> SEQUENCE: 352

Ala Gly Arg Glu Glu Tyr Ser Ala Met
1               5

<210> SEQ ID NO 353
<211> LENGTH: 9
<212> TYPE: PRT
<213> ORGANISM: homo sapiens

<400> SEQUENCE: 353

Gly Arg Glu Glu Tyr Ser Ala Met Arg
1               5

<210> SEQ ID NO 354
<211> LENGTH: 9
<212> TYPE: PRT
<213> ORGANISM: homo sapiens

<400> SEQUENCE: 354

Arg Glu Glu Tyr Ser Ala Met Arg Asp
1               5

<210> SEQ ID NO 355
<211> LENGTH: 17
<212> TYPE: PRT
<213> ORGANISM: homo sapiens

<400> SEQUENCE: 355

Tyr Lys Leu Val Val Val Gly Ala Val Gly Val Gly Lys Ser Ala Leu
1               5                   10                  15

Thr

<210> SEQ ID NO 356
<211> LENGTH: 9
<212> TYPE: PRT
<213> ORGANISM: homo sapiens

<400> SEQUENCE: 356

Tyr Lys Leu Val Val Val Gly Ala Val
1               5

<210> SEQ ID NO 357
<211> LENGTH: 9
<212> TYPE: PRT
<213> ORGANISM: homo sapiens

<400> SEQUENCE: 357

```
Lys Leu Val Val Gly Ala Val Gly
1               5

<210> SEQ ID NO 358
<211> LENGTH: 9
<212> TYPE: PRT
<213> ORGANISM: homo sapiens

<400> SEQUENCE: 358

Leu Val Val Val Gly Ala Val Gly Val
1               5

<210> SEQ ID NO 359
<211> LENGTH: 9
<212> TYPE: PRT
<213> ORGANISM: homo sapiens

<400> SEQUENCE: 359

Val Val Val Gly Ala Val Gly Val Gly
1               5

<210> SEQ ID NO 360
<211> LENGTH: 9
<212> TYPE: PRT
<213> ORGANISM: homo sapiens

<400> SEQUENCE: 360

Val Val Gly Ala Val Gly Val Gly Lys
1               5

<210> SEQ ID NO 361
<211> LENGTH: 9
<212> TYPE: PRT
<213> ORGANISM: homo sapiens

<400> SEQUENCE: 361

Val Gly Ala Val Gly Val Gly Lys Ser
1               5

<210> SEQ ID NO 362
<211> LENGTH: 9
<212> TYPE: PRT
<213> ORGANISM: homo sapiens

<400> SEQUENCE: 362

Gly Ala Val Gly Val Gly Lys Ser Ala
1               5

<210> SEQ ID NO 363
<211> LENGTH: 9
<212> TYPE: PRT
<213> ORGANISM: homo sapiens

<400> SEQUENCE: 363

Ala Val Gly Val Gly Lys Ser Ala Leu
1               5

<210> SEQ ID NO 364
<211> LENGTH: 9
<212> TYPE: PRT
<213> ORGANISM: homo sapiens

<400> SEQUENCE: 364

Val Gly Val Gly Lys Ser Ala Leu Thr
```

-continued

```
<210> SEQ ID NO 365
<211> LENGTH: 17
<212> TYPE: PRT
<213> ORGANISM: homo sapiens

<400> SEQUENCE: 365

Tyr Lys Leu Val Val Val Gly Ala Asp Gly Val Gly Lys Ser Ala Leu
1               5                   10                  15

Thr

<210> SEQ ID NO 366
<211> LENGTH: 9
<212> TYPE: PRT
<213> ORGANISM: homo sapiens

<400> SEQUENCE: 366

Tyr Lys Leu Val Val Val Gly Ala Asp
1               5

<210> SEQ ID NO 367
<211> LENGTH: 9
<212> TYPE: PRT
<213> ORGANISM: homo sapiens

<400> SEQUENCE: 367

Lys Leu Val Val Val Gly Ala Asp Gly
1               5

<210> SEQ ID NO 368
<211> LENGTH: 9
<212> TYPE: PRT
<213> ORGANISM: homo sapiens

<400> SEQUENCE: 368

Leu Val Val Val Gly Ala Asp Gly Val
1               5

<210> SEQ ID NO 369
<211> LENGTH: 9
<212> TYPE: PRT
<213> ORGANISM: homo sapiens

<400> SEQUENCE: 369

Val Val Val Gly Ala Asp Gly Val Gly
1               5

<210> SEQ ID NO 370
<211> LENGTH: 9
<212> TYPE: PRT
<213> ORGANISM: homo sapiens

<400> SEQUENCE: 370

Val Val Gly Ala Asp Gly Val Gly Lys
1               5

<210> SEQ ID NO 371
<211> LENGTH: 9
<212> TYPE: PRT
<213> ORGANISM: homo sapiens

<400> SEQUENCE: 371

Val Gly Ala Asp Gly Val Gly Lys Ser
```

```
1               5

<210> SEQ ID NO 372
<211> LENGTH: 9
<212> TYPE: PRT
<213> ORGANISM: homo sapiens

<400> SEQUENCE: 372

Gly Ala Asp Gly Val Gly Lys Ser Ala
1               5

<210> SEQ ID NO 373
<211> LENGTH: 9
<212> TYPE: PRT
<213> ORGANISM: homo sapiens

<400> SEQUENCE: 373

Ala Asp Gly Val Gly Lys Ser Ala Leu
1               5

<210> SEQ ID NO 374
<211> LENGTH: 9
<212> TYPE: PRT
<213> ORGANISM: homo sapiens

<400> SEQUENCE: 374

Asp Gly Val Gly Lys Ser Ala Leu Thr
1               5

<210> SEQ ID NO 375
<211> LENGTH: 17
<212> TYPE: PRT
<213> ORGANISM: homo sapiens

<400> SEQUENCE: 375

Phe Arg His Ser Val Val Val Pro Cys Glu Pro Pro Glu Val Gly Ser
1               5                   10                  15

Asp

<210> SEQ ID NO 376
<211> LENGTH: 9
<212> TYPE: PRT
<213> ORGANISM: homo sapiens

<400> SEQUENCE: 376

Phe Arg His Ser Val Val Val Pro Cys
1               5

<210> SEQ ID NO 377
<211> LENGTH: 9
<212> TYPE: PRT
<213> ORGANISM: homo sapiens

<400> SEQUENCE: 377

Arg His Ser Val Val Val Pro Cys Glu
1               5

<210> SEQ ID NO 378
<211> LENGTH: 9
<212> TYPE: PRT
<213> ORGANISM: homo sapiens

<400> SEQUENCE: 378

His Ser Val Val Val Pro Cys Glu Pro
```

```
1               5

<210> SEQ ID NO 379
<211> LENGTH: 9
<212> TYPE: PRT
<213> ORGANISM: homo sapiens

<400> SEQUENCE: 379

Ser Val Val Val Pro Cys Glu Pro Pro
1               5

<210> SEQ ID NO 380
<211> LENGTH: 9
<212> TYPE: PRT
<213> ORGANISM: homo sapiens

<400> SEQUENCE: 380

Val Val Val Pro Cys Glu Pro Pro Glu
1               5

<210> SEQ ID NO 381
<211> LENGTH: 9
<212> TYPE: PRT
<213> ORGANISM: homo sapiens

<400> SEQUENCE: 381

Val Val Pro Cys Glu Pro Pro Glu Val
1               5

<210> SEQ ID NO 382
<211> LENGTH: 9
<212> TYPE: PRT
<213> ORGANISM: homo sapiens

<400> SEQUENCE: 382

Val Pro Cys Glu Pro Pro Glu Val Gly
1               5

<210> SEQ ID NO 383
<211> LENGTH: 9
<212> TYPE: PRT
<213> ORGANISM: homo sapiens

<400> SEQUENCE: 383

Pro Cys Glu Pro Pro Glu Val Gly Ser
1               5

<210> SEQ ID NO 384
<211> LENGTH: 9
<212> TYPE: PRT
<213> ORGANISM: homo sapiens

<400> SEQUENCE: 384

Cys Glu Pro Pro Glu Val Gly Ser Asp
1               5

<210> SEQ ID NO 385
<211> LENGTH: 17
<212> TYPE: PRT
<213> ORGANISM: homo sapiens

<400> SEQUENCE: 385

Ser Ser Cys Met Gly Gly Met Asn Trp Arg Pro Ile Leu Thr Ile Ile
1               5                   10                  15
```

Thr

<210> SEQ ID NO 386
<211> LENGTH: 9
<212> TYPE: PRT
<213> ORGANISM: homo sapiens

<400> SEQUENCE: 386

Ser Ser Cys Met Gly Gly Met Asn Trp
1               5

<210> SEQ ID NO 387
<211> LENGTH: 9
<212> TYPE: PRT
<213> ORGANISM: homo sapiens

<400> SEQUENCE: 387

Ser Cys Met Gly Gly Met Asn Trp Arg
1               5

<210> SEQ ID NO 388
<211> LENGTH: 9
<212> TYPE: PRT
<213> ORGANISM: homo sapiens

<400> SEQUENCE: 388

Cys Met Gly Gly Met Asn Trp Arg Pro
1               5

<210> SEQ ID NO 389
<211> LENGTH: 9
<212> TYPE: PRT
<213> ORGANISM: homo sapiens

<400> SEQUENCE: 389

Met Gly Gly Met Asn Trp Arg Pro Ile
1               5

<210> SEQ ID NO 390
<211> LENGTH: 9
<212> TYPE: PRT
<213> ORGANISM: homo sapiens

<400> SEQUENCE: 390

Gly Gly Met Asn Trp Arg Pro Ile Leu
1               5

<210> SEQ ID NO 391
<211> LENGTH: 9
<212> TYPE: PRT
<213> ORGANISM: homo sapiens

<400> SEQUENCE: 391

Gly Met Asn Trp Arg Pro Ile Leu Thr
1               5

<210> SEQ ID NO 392
<211> LENGTH: 9
<212> TYPE: PRT
<213> ORGANISM: homo sapiens

<400> SEQUENCE: 392

Met Asn Trp Arg Pro Ile Leu Thr Ile
1               5

```
<210> SEQ ID NO 393
<211> LENGTH: 9
<212> TYPE: PRT
<213> ORGANISM: homo sapiens

<400> SEQUENCE: 393

Asn Trp Arg Pro Ile Leu Thr Ile Ile
1               5

<210> SEQ ID NO 394
<211> LENGTH: 9
<212> TYPE: PRT
<213> ORGANISM: homo sapiens

<400> SEQUENCE: 394

Trp Arg Pro Ile Leu Thr Ile Ile Thr
1               5

<210> SEQ ID NO 395
<211> LENGTH: 17
<212> TYPE: PRT
<213> ORGANISM: homo sapiens

<400> SEQUENCE: 395

Tyr Leu Asp Asp Arg Asn Thr Phe Leu His Ser Val Val Pro Tyr
1               5                   10                  15

Glu

<210> SEQ ID NO 396
<211> LENGTH: 9
<212> TYPE: PRT
<213> ORGANISM: homo sapiens

<400> SEQUENCE: 396

Tyr Leu Asp Asp Arg Asn Thr Phe Leu
1               5

<210> SEQ ID NO 397
<211> LENGTH: 9
<212> TYPE: PRT
<213> ORGANISM: homo sapiens

<400> SEQUENCE: 397

Leu Asp Asp Arg Asn Thr Phe Leu His
1               5

<210> SEQ ID NO 398
<211> LENGTH: 9
<212> TYPE: PRT
<213> ORGANISM: homo sapiens

<400> SEQUENCE: 398

Asp Asp Arg Asn Thr Phe Leu His Ser
1               5

<210> SEQ ID NO 399
<211> LENGTH: 9
<212> TYPE: PRT
<213> ORGANISM: homo sapiens

<400> SEQUENCE: 399

Asp Arg Asn Thr Phe Leu His Ser Val
1               5
```

```
<210> SEQ ID NO 400
<211> LENGTH: 9
<212> TYPE: PRT
<213> ORGANISM: homo sapiens

<400> SEQUENCE: 400

Arg Asn Thr Phe Leu His Ser Val Val
1               5

<210> SEQ ID NO 401
<211> LENGTH: 9
<212> TYPE: PRT
<213> ORGANISM: homo sapiens

<400> SEQUENCE: 401

Asn Thr Phe Leu His Ser Val Val Val
1               5

<210> SEQ ID NO 402
<211> LENGTH: 9
<212> TYPE: PRT
<213> ORGANISM: homo sapiens

<400> SEQUENCE: 402

Thr Phe Leu His Ser Val Val Val Pro
1               5

<210> SEQ ID NO 403
<211> LENGTH: 9
<212> TYPE: PRT
<213> ORGANISM: homo sapiens

<400> SEQUENCE: 403

Phe Leu His Ser Val Val Val Pro Tyr
1               5

<210> SEQ ID NO 404
<211> LENGTH: 9
<212> TYPE: PRT
<213> ORGANISM: homo sapiens

<400> SEQUENCE: 404

Leu His Ser Val Val Val Pro Tyr Glu
1               5

<210> SEQ ID NO 405
<211> LENGTH: 17
<212> TYPE: PRT
<213> ORGANISM: homo sapiens

<400> SEQUENCE: 405

Trp Lys Ser Pro Asn Gly Thr Ile Gln Asn Ile Leu Gly Gly Thr Val
1               5                   10                  15

Phe

<210> SEQ ID NO 406
<211> LENGTH: 9
<212> TYPE: PRT
<213> ORGANISM: homo sapiens

<400> SEQUENCE: 406

Trp Lys Ser Pro Asn Gly Thr Ile Gln
1               5
```

```
<210> SEQ ID NO 407
<211> LENGTH: 9
<212> TYPE: PRT
<213> ORGANISM: homo sapiens

<400> SEQUENCE: 407

Lys Ser Pro Asn Gly Thr Ile Gln Asn
1               5

<210> SEQ ID NO 408
<211> LENGTH: 9
<212> TYPE: PRT
<213> ORGANISM: homo sapiens

<400> SEQUENCE: 408

Ser Pro Asn Gly Thr Ile Gln Asn Ile
1               5

<210> SEQ ID NO 409
<211> LENGTH: 9
<212> TYPE: PRT
<213> ORGANISM: homo sapiens

<400> SEQUENCE: 409

Pro Asn Gly Thr Ile Gln Asn Ile Leu
1               5

<210> SEQ ID NO 410
<211> LENGTH: 9
<212> TYPE: PRT
<213> ORGANISM: homo sapiens

<400> SEQUENCE: 410

Asn Gly Thr Ile Gln Asn Ile Leu Gly
1               5

<210> SEQ ID NO 411
<211> LENGTH: 9
<212> TYPE: PRT
<213> ORGANISM: homo sapiens

<400> SEQUENCE: 411

Gly Thr Ile Gln Asn Ile Leu Gly Gly
1               5

<210> SEQ ID NO 412
<211> LENGTH: 9
<212> TYPE: PRT
<213> ORGANISM: homo sapiens

<400> SEQUENCE: 412

Thr Ile Gln Asn Ile Leu Gly Gly Thr
1               5

<210> SEQ ID NO 413
<211> LENGTH: 9
<212> TYPE: PRT
<213> ORGANISM: homo sapiens

<400> SEQUENCE: 413

Ile Gln Asn Ile Leu Gly Gly Thr Val
1               5

<210> SEQ ID NO 414
```

-continued

```
<211> LENGTH: 9
<212> TYPE: PRT
<213> ORGANISM: homo sapiens

<400> SEQUENCE: 414

Gln Asn Ile Leu Gly Gly Thr Val Phe
1               5

<210> SEQ ID NO 415
<211> LENGTH: 15
<212> TYPE: PRT
<213> ORGANISM: homo sapiens

<400> SEQUENCE: 415

Asp Ile Leu Asp Thr Ala Gly His Glu Glu Tyr Ser Ala Met Arg
1               5                   10                  15

<210> SEQ ID NO 416
<211> LENGTH: 8
<212> TYPE: PRT
<213> ORGANISM: homo sapiens

<400> SEQUENCE: 416

Asp Ile Leu Asp Thr Ala Gly His
1               5

<210> SEQ ID NO 417
<211> LENGTH: 8
<212> TYPE: PRT
<213> ORGANISM: homo sapiens

<400> SEQUENCE: 417

Ile Leu Asp Thr Ala Gly His Glu
1               5

<210> SEQ ID NO 418
<211> LENGTH: 8
<212> TYPE: PRT
<213> ORGANISM: homo sapiens

<400> SEQUENCE: 418

Leu Asp Thr Ala Gly His Glu Glu
1               5

<210> SEQ ID NO 419
<211> LENGTH: 8
<212> TYPE: PRT
<213> ORGANISM: homo sapiens

<400> SEQUENCE: 419

Asp Thr Ala Gly His Glu Glu Tyr
1               5

<210> SEQ ID NO 420
<211> LENGTH: 8
<212> TYPE: PRT
<213> ORGANISM: homo sapiens

<400> SEQUENCE: 420

Thr Ala Gly His Glu Glu Tyr Ser
1               5

<210> SEQ ID NO 421
<211> LENGTH: 8
<212> TYPE: PRT
```

<213> ORGANISM: homo sapiens

<400> SEQUENCE: 421

Ala Gly His Glu Glu Tyr Ser Ala
1               5

<210> SEQ ID NO 422
<211> LENGTH: 8
<212> TYPE: PRT
<213> ORGANISM: homo sapiens

<400> SEQUENCE: 422

Gly His Glu Glu Tyr Ser Ala Met
1               5

<210> SEQ ID NO 423
<211> LENGTH: 8
<212> TYPE: PRT
<213> ORGANISM: homo sapiens

<400> SEQUENCE: 423

His Glu Glu Tyr Ser Ala Met Arg
1               5

<210> SEQ ID NO 424
<211> LENGTH: 15
<212> TYPE: PRT
<213> ORGANISM: homo sapiens

<400> SEQUENCE: 424

Asp Ile Leu Asp Thr Ala Gly Leu Glu Glu Tyr Ser Ala Met Arg
1               5                   10                  15

<210> SEQ ID NO 425
<211> LENGTH: 8
<212> TYPE: PRT
<213> ORGANISM: homo sapiens

<400> SEQUENCE: 425

Asp Ile Leu Asp Thr Ala Gly Leu
1               5

<210> SEQ ID NO 426
<211> LENGTH: 8
<212> TYPE: PRT
<213> ORGANISM: homo sapiens

<400> SEQUENCE: 426

Ile Leu Asp Thr Ala Gly Leu Glu
1               5

<210> SEQ ID NO 427
<211> LENGTH: 8
<212> TYPE: PRT
<213> ORGANISM: homo sapiens

<400> SEQUENCE: 427

Leu Asp Thr Ala Gly Leu Glu Glu
1               5

<210> SEQ ID NO 428
<211> LENGTH: 8
<212> TYPE: PRT
<213> ORGANISM: homo sapiens

```
<400> SEQUENCE: 428

Asp Thr Ala Gly Leu Glu Glu Tyr
1               5

<210> SEQ ID NO 429
<211> LENGTH: 8
<212> TYPE: PRT
<213> ORGANISM: homo sapiens

<400> SEQUENCE: 429

Thr Ala Gly Leu Glu Glu Tyr Ser
1               5

<210> SEQ ID NO 430
<211> LENGTH: 8
<212> TYPE: PRT
<213> ORGANISM: homo sapiens

<400> SEQUENCE: 430

Ala Gly Leu Glu Glu Tyr Ser Ala
1               5

<210> SEQ ID NO 431
<211> LENGTH: 8
<212> TYPE: PRT
<213> ORGANISM: homo sapiens

<400> SEQUENCE: 431

Gly Leu Glu Glu Tyr Ser Ala Met
1               5

<210> SEQ ID NO 432
<211> LENGTH: 8
<212> TYPE: PRT
<213> ORGANISM: homo sapiens

<400> SEQUENCE: 432

Leu Glu Glu Tyr Ser Ala Met Arg
1               5

<210> SEQ ID NO 433
<211> LENGTH: 15
<212> TYPE: PRT
<213> ORGANISM: homo sapiens

<400> SEQUENCE: 433

Asp Ile Leu Asp Thr Ala Gly Arg Glu Glu Tyr Ser Ala Met Arg
1               5                   10                  15

<210> SEQ ID NO 434
<211> LENGTH: 8
<212> TYPE: PRT
<213> ORGANISM: homo sapiens

<400> SEQUENCE: 434

Asp Ile Leu Asp Thr Ala Gly Arg
1               5

<210> SEQ ID NO 435
<211> LENGTH: 8
<212> TYPE: PRT
<213> ORGANISM: homo sapiens

<400> SEQUENCE: 435
```

Ile Leu Asp Thr Ala Gly Arg Glu
1               5

<210> SEQ ID NO 436
<211> LENGTH: 8
<212> TYPE: PRT
<213> ORGANISM: homo sapiens

<400> SEQUENCE: 436

Leu Asp Thr Ala Gly Arg Glu Glu
1               5

<210> SEQ ID NO 437
<211> LENGTH: 8
<212> TYPE: PRT
<213> ORGANISM: homo sapiens

<400> SEQUENCE: 437

Asp Thr Ala Gly Arg Glu Glu Tyr
1               5

<210> SEQ ID NO 438
<211> LENGTH: 8
<212> TYPE: PRT
<213> ORGANISM: homo sapiens

<400> SEQUENCE: 438

Thr Ala Gly Arg Glu Glu Tyr Ser
1               5

<210> SEQ ID NO 439
<211> LENGTH: 8
<212> TYPE: PRT
<213> ORGANISM: homo sapiens

<400> SEQUENCE: 439

Ala Gly Arg Glu Glu Tyr Ser Ala
1               5

<210> SEQ ID NO 440
<211> LENGTH: 8
<212> TYPE: PRT
<213> ORGANISM: homo sapiens

<400> SEQUENCE: 440

Gly Arg Glu Glu Tyr Ser Ala Met
1               5

<210> SEQ ID NO 441
<211> LENGTH: 8
<212> TYPE: PRT
<213> ORGANISM: homo sapiens

<400> SEQUENCE: 441

Arg Glu Glu Tyr Ser Ala Met Arg
1               5

<210> SEQ ID NO 442
<211> LENGTH: 15
<212> TYPE: PRT
<213> ORGANISM: homo sapiens

<400> SEQUENCE: 442

Lys Leu Val Val Val Gly Ala Val Gly Val Gly Lys Ser Ala Leu
1               5                   10                  15

<210> SEQ ID NO 443
<211> LENGTH: 8
<212> TYPE: PRT
<213> ORGANISM: homo sapiens

<400> SEQUENCE: 443

Lys Leu Val Val Val Gly Ala Val
1               5

<210> SEQ ID NO 444
<211> LENGTH: 8
<212> TYPE: PRT
<213> ORGANISM: homo sapiens

<400> SEQUENCE: 444

Leu Val Val Val Gly Ala Val Gly
1               5

<210> SEQ ID NO 445
<211> LENGTH: 8
<212> TYPE: PRT
<213> ORGANISM: homo sapiens

<400> SEQUENCE: 445

Val Val Val Gly Ala Val Gly Val
1               5

<210> SEQ ID NO 446
<211> LENGTH: 8
<212> TYPE: PRT
<213> ORGANISM: homo sapiens

<400> SEQUENCE: 446

Val Val Gly Ala Val Gly Val Gly
1               5

<210> SEQ ID NO 447
<211> LENGTH: 8
<212> TYPE: PRT
<213> ORGANISM: homo sapiens

<400> SEQUENCE: 447

Val Gly Ala Val Gly Val Gly Lys
1               5

<210> SEQ ID NO 448
<211> LENGTH: 8
<212> TYPE: PRT
<213> ORGANISM: homo sapiens

<400> SEQUENCE: 448

Gly Ala Val Gly Val Gly Lys Ser
1               5

<210> SEQ ID NO 449
<211> LENGTH: 8
<212> TYPE: PRT
<213> ORGANISM: homo sapiens

<400> SEQUENCE: 449

Ala Val Gly Val Gly Lys Ser Ala
1               5

```
<210> SEQ ID NO 450
<211> LENGTH: 8
<212> TYPE: PRT
<213> ORGANISM: homo sapiens

<400> SEQUENCE: 450

Val Gly Val Gly Lys Ser Ala Leu
1               5

<210> SEQ ID NO 451
<211> LENGTH: 15
<212> TYPE: PRT
<213> ORGANISM: homo sapiens

<400> SEQUENCE: 451

Lys Leu Val Val Val Gly Ala Asp Gly Val Gly Lys Ser Ala Leu
1               5                   10                  15

<210> SEQ ID NO 452
<211> LENGTH: 8
<212> TYPE: PRT
<213> ORGANISM: homo sapiens

<400> SEQUENCE: 452

Lys Leu Val Val Val Gly Ala Asp
1               5

<210> SEQ ID NO 453
<211> LENGTH: 8
<212> TYPE: PRT
<213> ORGANISM: homo sapiens

<400> SEQUENCE: 453

Leu Val Val Val Gly Ala Asp Gly
1               5

<210> SEQ ID NO 454
<211> LENGTH: 8
<212> TYPE: PRT
<213> ORGANISM: homo sapiens

<400> SEQUENCE: 454

Val Val Val Gly Ala Asp Gly Val
1               5

<210> SEQ ID NO 455
<211> LENGTH: 8
<212> TYPE: PRT
<213> ORGANISM: homo sapiens

<400> SEQUENCE: 455

Val Val Gly Ala Asp Gly Val Gly
1               5

<210> SEQ ID NO 456
<211> LENGTH: 8
<212> TYPE: PRT
<213> ORGANISM: homo sapiens

<400> SEQUENCE: 456

Val Gly Ala Asp Gly Val Gly Lys
1               5

<210> SEQ ID NO 457
<211> LENGTH: 8
```

```
<212> TYPE: PRT
<213> ORGANISM: homo sapiens

<400> SEQUENCE: 457

Gly Ala Asp Gly Val Gly Lys Ser
1               5

<210> SEQ ID NO 458
<211> LENGTH: 8
<212> TYPE: PRT
<213> ORGANISM: homo sapiens

<400> SEQUENCE: 458

Ala Asp Gly Val Gly Lys Ser Ala
1               5

<210> SEQ ID NO 459
<211> LENGTH: 8
<212> TYPE: PRT
<213> ORGANISM: homo sapiens

<400> SEQUENCE: 459

Asp Gly Val Gly Lys Ser Ala Leu
1               5

<210> SEQ ID NO 460
<211> LENGTH: 15
<212> TYPE: PRT
<213> ORGANISM: homo sapiens

<400> SEQUENCE: 460

Arg His Ser Val Val Pro Cys Glu Pro Pro Glu Val Gly Ser
1               5                   10                  15

<210> SEQ ID NO 461
<211> LENGTH: 8
<212> TYPE: PRT
<213> ORGANISM: homo sapiens

<400> SEQUENCE: 461

Arg His Ser Val Val Val Pro Cys
1               5

<210> SEQ ID NO 462
<211> LENGTH: 8
<212> TYPE: PRT
<213> ORGANISM: homo sapiens

<400> SEQUENCE: 462

His Ser Val Val Val Pro Cys Glu
1               5

<210> SEQ ID NO 463
<211> LENGTH: 8
<212> TYPE: PRT
<213> ORGANISM: homo sapiens

<400> SEQUENCE: 463

Ser Val Val Val Pro Cys Glu Pro
1               5

<210> SEQ ID NO 464
<211> LENGTH: 8
<212> TYPE: PRT
<213> ORGANISM: homo sapiens
```

-continued

<400> SEQUENCE: 464

Val Val Val Pro Cys Glu Pro Pro
1               5

<210> SEQ ID NO 465
<211> LENGTH: 8
<212> TYPE: PRT
<213> ORGANISM: homo sapiens

<400> SEQUENCE: 465

Val Val Pro Cys Glu Pro Pro Glu
1               5

<210> SEQ ID NO 466
<211> LENGTH: 8
<212> TYPE: PRT
<213> ORGANISM: homo sapiens

<400> SEQUENCE: 466

Val Pro Cys Glu Pro Pro Glu Val
1               5

<210> SEQ ID NO 467
<211> LENGTH: 8
<212> TYPE: PRT
<213> ORGANISM: homo sapiens

<400> SEQUENCE: 467

Pro Cys Glu Pro Pro Glu Val Gly
1               5

<210> SEQ ID NO 468
<211> LENGTH: 8
<212> TYPE: PRT
<213> ORGANISM: homo sapiens

<400> SEQUENCE: 468

Cys Glu Pro Pro Glu Val Gly Ser
1               5

<210> SEQ ID NO 469
<211> LENGTH: 15
<212> TYPE: PRT
<213> ORGANISM: homo sapiens

<400> SEQUENCE: 469

Ser Cys Met Gly Gly Met Asn Trp Arg Pro Ile Leu Thr Ile Ile
1               5                   10                  15

<210> SEQ ID NO 470
<211> LENGTH: 8
<212> TYPE: PRT
<213> ORGANISM: homo sapiens

<400> SEQUENCE: 470

Ser Cys Met Gly Gly Met Asn Trp
1               5

<210> SEQ ID NO 471
<211> LENGTH: 8
<212> TYPE: PRT
<213> ORGANISM: homo sapiens

<400> SEQUENCE: 471

Cys Met Gly Gly Met Asn Trp Arg
1               5

<210> SEQ ID NO 472
<211> LENGTH: 8
<212> TYPE: PRT
<213> ORGANISM: homo sapiens

<400> SEQUENCE: 472

Met Gly Gly Met Asn Trp Arg Pro
1               5

<210> SEQ ID NO 473
<211> LENGTH: 8
<212> TYPE: PRT
<213> ORGANISM: homo sapiens

<400> SEQUENCE: 473

Gly Gly Met Asn Trp Arg Pro Ile
1               5

<210> SEQ ID NO 474
<211> LENGTH: 8
<212> TYPE: PRT
<213> ORGANISM: homo sapiens

<400> SEQUENCE: 474

Gly Met Asn Trp Arg Pro Ile Leu
1               5

<210> SEQ ID NO 475
<211> LENGTH: 8
<212> TYPE: PRT
<213> ORGANISM: homo sapiens

<400> SEQUENCE: 475

Met Asn Trp Arg Pro Ile Leu Thr
1               5

<210> SEQ ID NO 476
<211> LENGTH: 8
<212> TYPE: PRT
<213> ORGANISM: homo sapiens

<400> SEQUENCE: 476

Asn Trp Arg Pro Ile Leu Thr Ile
1               5

<210> SEQ ID NO 477
<211> LENGTH: 8
<212> TYPE: PRT
<213> ORGANISM: homo sapiens

<400> SEQUENCE: 477

Trp Arg Pro Ile Leu Thr Ile Ile
1               5

<210> SEQ ID NO 478
<211> LENGTH: 15
<212> TYPE: PRT
<213> ORGANISM: homo sapiens

<400> SEQUENCE: 478

Leu Asp Asp Arg Asn Thr Phe Leu His Ser Val Val Val Pro Tyr

<210> SEQ ID NO 479
<211> LENGTH: 8
<212> TYPE: PRT
<213> ORGANISM: homo sapiens

<400> SEQUENCE: 479

Leu Asp Asp Arg Asn Thr Phe Leu
1               5

<210> SEQ ID NO 480
<211> LENGTH: 8
<212> TYPE: PRT
<213> ORGANISM: homo sapiens

<400> SEQUENCE: 480

Asp Asp Arg Asn Thr Phe Leu His
1               5

<210> SEQ ID NO 481
<211> LENGTH: 8
<212> TYPE: PRT
<213> ORGANISM: homo sapiens

<400> SEQUENCE: 481

Asp Arg Asn Thr Phe Leu His Ser
1               5

<210> SEQ ID NO 482
<211> LENGTH: 8
<212> TYPE: PRT
<213> ORGANISM: homo sapiens

<400> SEQUENCE: 482

Arg Asn Thr Phe Leu His Ser Val
1               5

<210> SEQ ID NO 483
<211> LENGTH: 8
<212> TYPE: PRT
<213> ORGANISM: homo sapiens

<400> SEQUENCE: 483

Asn Thr Phe Leu His Ser Val Val
1               5

<210> SEQ ID NO 484
<211> LENGTH: 8
<212> TYPE: PRT
<213> ORGANISM: homo sapiens

<400> SEQUENCE: 484

Thr Phe Leu His Ser Val Val Val
1               5

<210> SEQ ID NO 485
<211> LENGTH: 8
<212> TYPE: PRT
<213> ORGANISM: homo sapiens

<400> SEQUENCE: 485

Phe Leu His Ser Val Val Val Pro
1               5

<210> SEQ ID NO 486
<211> LENGTH: 8
<212> TYPE: PRT
<213> ORGANISM: homo sapiens

<400> SEQUENCE: 486

Leu His Ser Val Val Val Pro Tyr
1               5

<210> SEQ ID NO 487
<211> LENGTH: 15
<212> TYPE: PRT
<213> ORGANISM: homo sapiens

<400> SEQUENCE: 487

Lys Ser Pro Asn Gly Thr Ile Gln Asn Ile Leu Gly Gly Thr Val
1               5                   10                  15

<210> SEQ ID NO 488
<211> LENGTH: 8
<212> TYPE: PRT
<213> ORGANISM: homo sapiens

<400> SEQUENCE: 488

Lys Ser Pro Asn Gly Thr Ile Gln
1               5

<210> SEQ ID NO 489
<211> LENGTH: 8
<212> TYPE: PRT
<213> ORGANISM: homo sapiens

<400> SEQUENCE: 489

Ser Pro Asn Gly Thr Ile Gln Asn
1               5

<210> SEQ ID NO 490
<211> LENGTH: 8
<212> TYPE: PRT
<213> ORGANISM: homo sapiens

<400> SEQUENCE: 490

Pro Asn Gly Thr Ile Gln Asn Ile
1               5

<210> SEQ ID NO 491
<211> LENGTH: 8
<212> TYPE: PRT
<213> ORGANISM: homo sapiens

<400> SEQUENCE: 491

Asn Gly Thr Ile Gln Asn Ile Leu
1               5

<210> SEQ ID NO 492
<211> LENGTH: 8
<212> TYPE: PRT
<213> ORGANISM: homo sapiens

<400> SEQUENCE: 492

Gly Thr Ile Gln Asn Ile Leu Gly
1               5

<210> SEQ ID NO 493

```
<211> LENGTH: 8
<212> TYPE: PRT
<213> ORGANISM: homo sapiens

<400> SEQUENCE: 493

Thr Ile Gln Asn Ile Leu Gly Gly
1               5

<210> SEQ ID NO 494
<211> LENGTH: 8
<212> TYPE: PRT
<213> ORGANISM: homo sapiens

<400> SEQUENCE: 494

Ile Gln Asn Ile Leu Gly Gly Thr
1               5

<210> SEQ ID NO 495
<211> LENGTH: 8
<212> TYPE: PRT
<213> ORGANISM: homo sapiens

<400> SEQUENCE: 495

Gln Asn Ile Leu Gly Gly Thr Val
1               5

<210> SEQ ID NO 496
<211> LENGTH: 10
<212> TYPE: PRT
<213> ORGANISM: homo sapiens

<400> SEQUENCE: 496

Ile Leu Asp Thr Ala Gly His Glu Glu Tyr
1               5                   10

<210> SEQ ID NO 497
<211> LENGTH: 10
<212> TYPE: PRT
<213> ORGANISM: homo sapiens

<400> SEQUENCE: 497

Ile Leu Asp Thr Ala Gly Leu Glu Glu Tyr
1               5                   10

<210> SEQ ID NO 498
<211> LENGTH: 10
<212> TYPE: PRT
<213> ORGANISM: homo sapiens

<400> SEQUENCE: 498

Ile Leu Asp Thr Ala Gly Arg Glu Glu Tyr
1               5                   10

<210> SEQ ID NO 499
<211> LENGTH: 10
<212> TYPE: PRT
<213> ORGANISM: homo sapiens

<400> SEQUENCE: 499

Ser Pro Asn Gly Thr Ile Gln Asn Ile Leu
1               5                   10

<210> SEQ ID NO 500
<211> LENGTH: 9
<212> TYPE: PRT
```

```
<213> ORGANISM: homo sapiens

<400> SEQUENCE: 500

Val Val Pro Cys Glu Pro Pro Glu Val
1               5

<210> SEQ ID NO 501
<211> LENGTH: 10
<212> TYPE: PRT
<213> ORGANISM: homo sapiens

<400> SEQUENCE: 501

Ser Ser Cys Met Gly Gly Met Asn Trp Arg
1               5                   10

<210> SEQ ID NO 502
<211> LENGTH: 9
<212> TYPE: PRT
<213> ORGANISM: homo sapiens

<400> SEQUENCE: 502

Tyr Leu Asp Asp Arg Asn Thr Phe Leu
1               5

<210> SEQ ID NO 503
<211> LENGTH: 9
<212> TYPE: PRT
<213> ORGANISM: homo sapiens

<400> SEQUENCE: 503

Val Val Gly Ala Val Gly Val Gly Lys
1               5

<210> SEQ ID NO 504
<211> LENGTH: 10
<212> TYPE: PRT
<213> ORGANISM: homo sapiens

<400> SEQUENCE: 504

Val Val Val Gly Ala Val Gly Val Gly Lys
1               5                   10

<210> SEQ ID NO 505
<211> LENGTH: 9
<212> TYPE: PRT
<213> ORGANISM: homo sapiens

<400> SEQUENCE: 505

Val Val Gly Ala Asp Gly Val Gly Lys
1               5

<210> SEQ ID NO 506
<211> LENGTH: 10
<212> TYPE: PRT
<213> ORGANISM: homo sapiens

<400> SEQUENCE: 506

Val Val Val Gly Ala Asp Gly Val Gly Lys
1               5                   10

<210> SEQ ID NO 507
<211> LENGTH: 10
<212> TYPE: PRT
<213> ORGANISM: Artificial Sequence
<220> FEATURE:
```

<223> OTHER INFORMATION: synthetic

<400> SEQUENCE: 507

Ile Leu Asp Thr Ala Gly His Asp Glu Tyr
1               5                   10

<210> SEQ ID NO 508
<211> LENGTH: 10
<212> TYPE: PRT
<213> ORGANISM: Artificial Sequence
<220> FEATURE:
<223> OTHER INFORMATION: synthetic

<400> SEQUENCE: 508

Ile Leu Asp Thr Ala Gly Leu Asp Glu Tyr
1               5                   10

<210> SEQ ID NO 509
<211> LENGTH: 10
<212> TYPE: PRT
<213> ORGANISM: Artificial Sequence
<220> FEATURE:
<223> OTHER INFORMATION: synthetic

<400> SEQUENCE: 509

Ile Leu Asp Thr Ala Gly Arg Glu Asp Tyr
1               5                   10

<210> SEQ ID NO 510
<211> LENGTH: 10
<212> TYPE: PRT
<213> ORGANISM: Artificial Sequence
<220> FEATURE:
<223> OTHER INFORMATION: synthetic

<400> SEQUENCE: 510

Ser Pro Asn Ala Thr Ile Gln Asn Ile Leu
1               5                   10

<210> SEQ ID NO 511
<211> LENGTH: 9
<212> TYPE: PRT
<213> ORGANISM: Artificial Sequence
<220> FEATURE:
<223> OTHER INFORMATION: synthetic

<400> SEQUENCE: 511

Val Val Pro Cys Glu Pro Pro Asp Val
1               5

<210> SEQ ID NO 512
<211> LENGTH: 10
<212> TYPE: PRT
<213> ORGANISM: Artificial Sequence
<220> FEATURE:
<223> OTHER INFORMATION: synthetic

<400> SEQUENCE: 512

Ser Ser Cys Met Ala Gly Met Asn Trp Arg
1               5                   10

<210> SEQ ID NO 513
<211> LENGTH: 9
<212> TYPE: PRT
<213> ORGANISM: Artificial Sequence
<220> FEATURE:
<223> OTHER INFORMATION: synthetic

<400> SEQUENCE: 513

Tyr Leu Glu Asp Arg Asn Thr Phe Leu
1               5

<210> SEQ ID NO 514
<211> LENGTH: 9
<212> TYPE: PRT
<213> ORGANISM: Artificial Sequence
<220> FEATURE:
<223> OTHER INFORMATION: synthetic

<400> SEQUENCE: 514

Val Val Gly Ala Val Gly Leu Gly Lys
1               5

<210> SEQ ID NO 515
<211> LENGTH: 10
<212> TYPE: PRT
<213> ORGANISM: Artificial Sequence
<220> FEATURE:
<223> OTHER INFORMATION: synthetic

<400> SEQUENCE: 515

Val Val Val Gly Ala Val Gly Leu Gly Lys
1               5                   10

<210> SEQ ID NO 516
<211> LENGTH: 9
<212> TYPE: PRT
<213> ORGANISM: Artificial Sequence
<220> FEATURE:
<223> OTHER INFORMATION: synthetic

<400> SEQUENCE: 516

Val Val Gly Ala Asp Gly Leu Gly Lys
1               5

<210> SEQ ID NO 517
<211> LENGTH: 10
<212> TYPE: PRT
<213> ORGANISM: Artificial Sequence
<220> FEATURE:
<223> OTHER INFORMATION: synthetic

<400> SEQUENCE: 517

Val Val Val Gly Ala Asp Gly Leu Gly Lys
1               5                   10

<210> SEQ ID NO 518
<211> LENGTH: 10
<212> TYPE: PRT
<213> ORGANISM: Artificial Sequence
<220> FEATURE:
<223> OTHER INFORMATION: synthetic

<400> SEQUENCE: 518

Ile Val Asp Thr Ala Gly His Glu Glu Tyr
1               5                   10

<210> SEQ ID NO 519
<211> LENGTH: 10
<212> TYPE: PRT
<213> ORGANISM: Artificial Sequence
<220> FEATURE:
<223> OTHER INFORMATION: synthetic

```
<400> SEQUENCE: 519

Ile Val Asp Thr Ala Gly Leu Glu Glu Tyr
1               5                   10

<210> SEQ ID NO 520
<211> LENGTH: 10
<212> TYPE: PRT
<213> ORGANISM: Artificial Sequence
<220> FEATURE:
<223> OTHER INFORMATION: synthetic

<400> SEQUENCE: 520

Ile Val Asp Thr Ala Gly Arg Glu Glu Tyr
1               5                   10

<210> SEQ ID NO 521
<211> LENGTH: 10
<212> TYPE: PRT
<213> ORGANISM: Artificial Sequence
<220> FEATURE:
<223> OTHER INFORMATION: synthetic

<400> SEQUENCE: 521

Ser Pro Asn Gly Thr Ile Gln Asn Ile Val
1               5                   10

<210> SEQ ID NO 522
<211> LENGTH: 9
<212> TYPE: PRT
<213> ORGANISM: Artificial Sequence
<220> FEATURE:
<223> OTHER INFORMATION: synthetic

<400> SEQUENCE: 522

Val Val Pro Cys Glu Pro Pro Glu Leu
1               5

<210> SEQ ID NO 523
<211> LENGTH: 10
<212> TYPE: PRT
<213> ORGANISM: Artificial Sequence
<220> FEATURE:
<223> OTHER INFORMATION: synthetic

<400> SEQUENCE: 523

Ser Thr Cys Met Gly Gly Met Asn Trp Arg
1               5                   10

<210> SEQ ID NO 524
<211> LENGTH: 9
<212> TYPE: PRT
<213> ORGANISM: Artificial Sequence
<220> FEATURE:
<223> OTHER INFORMATION: synthetic

<400> SEQUENCE: 524

Tyr Leu Asp Asp Arg Asn Thr Phe Val
1               5

<210> SEQ ID NO 525
<211> LENGTH: 9
<212> TYPE: PRT
<213> ORGANISM: Artificial Sequence
<220> FEATURE:
<223> OTHER INFORMATION: synthetic

<400> SEQUENCE: 525
```

```
Val Val Gly Ala Val Ala Val Gly Lys
1               5

<210> SEQ ID NO 526
<211> LENGTH: 10
<212> TYPE: PRT
<213> ORGANISM: Artificial Sequence
<220> FEATURE:
<223> OTHER INFORMATION: synthetic

<400> SEQUENCE: 526

Val Val Val Gly Ala Val Ala Val Gly Lys
1               5                   10

<210> SEQ ID NO 527
<211> LENGTH: 9
<212> TYPE: PRT
<213> ORGANISM: Artificial Sequence
<220> FEATURE:
<223> OTHER INFORMATION: synthetic

<400> SEQUENCE: 527

Val Val Gly Ala Asp Ala Val Gly Lys
1               5

<210> SEQ ID NO 528
<211> LENGTH: 10
<212> TYPE: PRT
<213> ORGANISM: Artificial Sequence
<220> FEATURE:
<223> OTHER INFORMATION: synthetic

<400> SEQUENCE: 528

Val Val Val Gly Ala Asp Ala Val Gly Lys
1               5                   10

<210> SEQ ID NO 529
<211> LENGTH: 10
<212> TYPE: PRT
<213> ORGANISM: Artificial Sequence
<220> FEATURE:
<223> OTHER INFORMATION: synthetic

<400> SEQUENCE: 529

Ile Leu Asp Ser Ala Gly His Glu Glu Tyr
1               5                   10

<210> SEQ ID NO 530
<211> LENGTH: 10
<212> TYPE: PRT
<213> ORGANISM: Artificial Sequence
<220> FEATURE:
<223> OTHER INFORMATION: synthetic

<400> SEQUENCE: 530

Ile Leu Asp Ser Ala Gly Leu Glu Glu Tyr
1               5                   10

<210> SEQ ID NO 531
<211> LENGTH: 10
<212> TYPE: PRT
<213> ORGANISM: Artificial Sequence
<220> FEATURE:
<223> OTHER INFORMATION: synthetic

<400> SEQUENCE: 531
```

```
Ile Leu Asp Ser Ala Gly Arg Glu Glu Tyr
1               5                   10

<210> SEQ ID NO 532
<211> LENGTH: 10
<212> TYPE: PRT
<213> ORGANISM: Artificial Sequence
<220> FEATURE:
<223> OTHER INFORMATION: synthetic

<400> SEQUENCE: 532

Ser Pro Asn Gly Thr Val Gln Asn Ile Leu
1               5                   10

<210> SEQ ID NO 533
<211> LENGTH: 9
<212> TYPE: PRT
<213> ORGANISM: Artificial Sequence
<220> FEATURE:
<223> OTHER INFORMATION: synthetic

<400> SEQUENCE: 533

Val Ile Pro Cys Glu Pro Pro Glu Val
1               5

<210> SEQ ID NO 534
<211> LENGTH: 10
<212> TYPE: PRT
<213> ORGANISM: Artificial Sequence
<220> FEATURE:
<223> OTHER INFORMATION: synthetic

<400> SEQUENCE: 534

Ser Ser Cys Met Gly Gly Met Gln Trp Arg
1               5                   10

<210> SEQ ID NO 535
<211> LENGTH: 9
<212> TYPE: PRT
<213> ORGANISM: Artificial Sequence
<220> FEATURE:
<223> OTHER INFORMATION: synthetic

<400> SEQUENCE: 535

Tyr Leu Asp Asp Arg Asn Ser Phe Leu
1               5

<210> SEQ ID NO 536
<211> LENGTH: 9
<212> TYPE: PRT
<213> ORGANISM: Artificial Sequence
<220> FEATURE:
<223> OTHER INFORMATION: synthetic

<400> SEQUENCE: 536

Val Val Gly Gly Val Gly Val Gly Lys
1               5

<210> SEQ ID NO 537
<211> LENGTH: 10
<212> TYPE: PRT
<213> ORGANISM: Artificial Sequence
<220> FEATURE:
<223> OTHER INFORMATION: synthetic

<400> SEQUENCE: 537

Val Val Val Gly Gly Val Gly Val Gly Lys
```

```
<210> SEQ ID NO 538
<211> LENGTH: 9
<212> TYPE: PRT
<213> ORGANISM: Artificial Sequence
<220> FEATURE:
<223> OTHER INFORMATION: synthetic

<400> SEQUENCE: 538

Val Val Gly Gly Asp Gly Val Gly Lys
1               5

<210> SEQ ID NO 539
<211> LENGTH: 10
<212> TYPE: PRT
<213> ORGANISM: Artificial Sequence
<220> FEATURE:
<223> OTHER INFORMATION: synthetic

<400> SEQUENCE: 539

Val Val Val Gly Gly Asp Gly Val Gly Lys
1               5                   10

<210> SEQ ID NO 540
<211> LENGTH: 10
<212> TYPE: PRT
<213> ORGANISM: Artificial Sequence
<220> FEATURE:
<223> OTHER INFORMATION: synthetic

<400> SEQUENCE: 540

Ile Val Asp Thr Ala Gly His Asp Glu Tyr
1               5                   10

<210> SEQ ID NO 541
<211> LENGTH: 10
<212> TYPE: PRT
<213> ORGANISM: Artificial Sequence
<220> FEATURE:
<223> OTHER INFORMATION: synthetic

<400> SEQUENCE: 541

Glu Tyr Ile Leu Gly Glu Asp Thr Ala His
1               5                   10
```

METHOD AND SYSTEM FOR NEOANTIGEN ANALYSIS

CROSS-REFERENCE TO RELATED APPLICATION

The present application claims benefit of U.S. Provisional Application No. 63/038,816, filed on Jun. 13, 2020, the disclosure of which is hereby incorporated by reference in its entirety.

REFERENCE TO SEQUENCE LISTING SUBMITTED ELECTRONICALLY

The content of the electronically submitted sequence listing, file name SeqListing-Neoantigen.txt, size 91,739 bytes, and date of creation Jun. 13, 2021, filed herewith, is incorporated herein by reference in its entirety.

TECHNICAL FIELD OF THE INVENTION

This present disclosure relates generally to the area of proteomics analysis, and specifically to proteomics analysis by means of liquid chromatography and mass spectrometry (LC-MS), and in more particular to a LC-MS-based method and system for analyzing small peptides, such as neoantigens.

BACKGROUND

Proteins encoded by genes carrying cancer-related mutations can be processed and mutation-bearing peptides can be presented on the cell surface in the context of human leukocyte antigen (HLA) molecules. Such peptides are called neoantigens. Neoantigens are truly personalized and cancer-specific, making them ideal anti-cancer therapeutic targets (Schumacher & Schreiber, 2015). Neoantigen can be recognized by T cells via their T cell receptor, which is the foundation for cancer immunotherapies (Lauss et al., 2017; Ott et al., 2017; Riaz et al., 2016; Sahin et al., 2017; Schumacher & Schreiber, 2015). To identify potential drug targets, numerous techniques have been reported recently to reveal the repertoire of neoantigens, including deep profiling of whole immunopeptidome and targeted detection approaches, as well as indirect assays on T cell reactivity (Bassani-Sternberg et al., 2016; Danilova et al., 2018; Wang et al., 2019). We have previously reported a technology termed "MANA-SRM" as a basic research platform for neoantigen detection from approximately 200 million tissue culture tumor cells, which was over 10-fold more sensitive than previously published techniques available for this purpose where over 2-3 billion cells are often required (Bassani-Sternberg et al., 2016; Wang et al., 2019). MANA-SRM is an ideal tool for tissue culture-based neoantigen assays and has enabled the development of the first off-the-shelf cancer vaccine targeting the most frequent mutation hotspot in human tumor suppressor gene TP53 and oncogene K-Ras (Douglass et al., 2021; Hsiue et al., 2021). However, the sensitivity and robustness of MANA-SRM is still not feasible for routine clinical applications given the limited amount of tumor tissue available from biopsy or surgical resection. A more sensitive, rapid and reproducible platform for neoantigen analysis from clinical samples is desperately needed before a neoantigen-based personalized cancer treatment can be established.

In recent years, mass spectrometry platforms have undergone a series of groundbreaking improvements (Bekker-Jensen et al., 2020; Meier et al., 2018; Zubarev & Makarov, 2013). Meanwhile, proteomic analysis is changing from a multi-hour assay to a short 21-minute run with little compromise on coverage (Bache et al., 2018). These improvements are dramatically revolutionizing mass spectrometry-based proteomics and making it more suitable for clinical applications.

SUMMARY OF THE INVENTION

This present disclosure provides further improvements in mass spectrometry, which covers several fields including the sample preparation, the hardware configuration and automation, and the mass spectrometry analysis, etc. More specifically, this present disclosure provides an integrated method and system (termed "Valid-NEO pipeline" hereinafter) for the detection and quantification of neoantigens from clinical samples without extensive manual sample processing.

In a first aspect, a method for a characterization of a target peptide through a detection approach is provided. The method comprises the following steps:

(1) introducing at least one guard molecule to mix with the target peptide, wherein each of the at least one guard molecule is configured to have similar characteristics as the target peptide, and yet is further configured to be distinguishable from the target peptide by the detection approach; and (2) applying the detection approach for the characterization of the target peptide.

Herein, the detection approach can comprise mass spectrometry analysis, and as such, each of the at least one guard molecule is configured to have an M/z value that is distinguishable from the target peptide by the mass spectrometry analysis.

Besides mass spectrometry analysis, the detection approach covered herein may involve other approaches as well. Examples may include: the use of target peptide sequence specific antibodies, a fluorescent detection method when guard peptide or compound and target peptide are designed to exhibit different fluorescent signals, the use of polymerase chain reaction (PCR)-based detection methods when the target peptides are associated with PCR-amplifiable signals, the use of nucleic acid sequence-based detection methods when the target peptide are associated with particular sequencing information, etc. Virtually any detection method that can distinguishingly detect the target peptide and the at least one guard compound can be applicable in the method, and is considered to be in the scope of this disclosure.

As used herein, as well as throughout other part of the disclosure, the term "characterization" of a target peptide may include either or both of detection (i.e. identification, qualification, or alike) and quantification of the target peptide.

As used herein, the term "guard molecule" refers to a molecule that coexists with the target peptide in one or more steps in the sample preparation and processing pipeline, which serves primarily to protect the target peptide from a loss in the analysis.

Specifically, if the detection approach involves mass spectrometry analysis, a guard molecule can be configured to have similar characteristics (e.g. similar hydrophobicity and charge status) as the target peptide, and to have a characteristic that can be differentiated from the target peptide by the downstream analytical instrument, such as a different M/z value that is distinguishable from the target peptide when analyzed by the mass spectrometer.

In another detection approach, such as using peptide-sequence specific antibody for the detection of a target peptide, where the sequence specific antibody can be used to selectively detect the target peptide and does not interact with the guard compound.

Regardless of the detection approach that is used, the co-presence of the guard molecule with the target peptide can ensure that the guard molecule behave similarly as the target peptides in sample preparation, thereby working as a blocker to prevent nonspecific binding of the target peptide to any surface or any substance that the target peptides may interact during the sample preparation and processing procedures.

As used herein, the term "similar characteristics" or "similarity" is substantially defined by the separation and fractionation mechanism adopted in a sample preparation and processing procedure, which can typically refer to a situation where two molecules, such as a first molecule (e.g. the target molecule) and a second molecule (e.g. a guard molecule), have substantially same hydrophobicity and charge status at a same pH environment. For example, in certain scenario where a sample preparation pipeline includes only reverse phase columns, a guard molecule that can be used in the method disclosed herein may share the similar hydrophobicity as the target molecule. In another scenario where a size exclusion column is used to separate the analytes, a guard molecule that can be used in the method disclosed herein may have a substantially similar molecular weight as the target molecule to therefore be able to co-exist with the target molecule in the sample preparation and processing procedures. In yet another scenario, both of the above types of columns may be used, thus for the selection of the guard molecule(s), a heavy isotope labeled peptide with the same sequence or peptides with just one amino acid different as target peptides as their guard peptides is the most feasible way to protect the target peptides from loss.

As used herein, the term "M/z value" is commonly known to people of ordinary skills in the field of mass spectrometry-based peptide analysis, which typically refers to a mass-to-charge ratio of a certain molecule. As is well understood, current mass spectrometry technology can readily separate two molecules that differ by approximately 1/30000 of a proton (i.e. one dalton) of their molecule weights. For example, a spectrometer can separate a first molecule with a molecular weight of 100.0001 from a second molecule with a molecular weight of 100.0002. As such, substitution of an amino acid residue with another amino acid residue having a different molecular weight or a different charge, or heavy isotope labelling of one or more amino acid residues can usually cause at least 1 dalton difference and can cause a target peptide and a guard peptide to be easily separated from one another.

According to certain embodiments of the method, the at least one guard molecule comprises a guard peptide. Herein, several possible embodiments exist.

In a first embodiment, the guard peptide may have a same amino acid residue sequence as the target peptide, and at least one amino acid residue in the guard peptide is heavy isotope labeled.

As used herein, the term "heavy isotope" that is labelled on a certain amino acid residue refers to the fact that in the guard peptide, there is at least one amino acid residue that is a heavy isotoe labeled amino acid residue, such as a Lysine residue with $C^{13}$ and/or $N^{15}$ labelings (i.e. the standard $C^{12}$ element from the amino acid is replaced by a heavy isotope element of $C^{13}$, and $N^{14}$ element can be replaced by a heavy isotpe element of $N^{15}$).

In a second embodiment, only one amino acid residue in the guard peptide may differ from the target peptide. Herein the differing amino acid residue in the guard peptide may, compared with the corresponding amino acid residue in the target peptide, have a same characteristics (i.e. hydrophobicity, charge status at the same pH, etc.) but have a different molecular weight. For example, regarding one target peptide: KRAS_Q61H neoantigen sequence ILDTAGHEEY (SEQ ID NO. 496, see Table 1), several possible guard peptides can be used, which may include the following non-limiting examples:

1) ILDTAGHDEY (SEQ ID NO. 507), obtained by substituting amino acid residue E at position 8 of the target peptide with D;

2) IVDTAGHEEY (SEQ ID NO. 518), obtained by substituting amino acid residue L at position 2 of the target peptide with V; and 3) ILDSAGHEEY (SEQ ID NO. 529), obtained by substituting amino acid residue T at position 4 of the target peptide with S.

By means of these above amino acid residue substitutions (i.e. E/D, L/V, and S/T), each of these guard peptides can behave similarly to that of the target peptides in the sample preparation procedure, but can still be easily differentiated by mass spectrometry.

In a third embodiment, at least two amino acid residues in the guard peptide may differ from the target peptide. For example, for the above target peptide: KRAS_Q61H neoantigen sequence ILDTAGHEEY (SEQ ID NO. 496), one possible guard peptide can be IVDTAGHDEY (SEQ ID NO. 540), which is obtained by substituting amino acid residue L at position 2 with V, and amino acid residue E at position 8 with D.

In a fourth embodiment, the guard peptide may have a scrambled sequence compared with the target peptide. For example, a possible guard peptide for the above exemplary target sequence ILDTAGHEEY (SEQ ID NO. 496) can be EYILGEDTAH (SEQ ID NO. 541), where they both have the same compositions of amino acid residues but have different sequences therefore will be readily differentiated by an feasible analytical method, such as using a sequence specific antibody or by a mass spectrometer.

In yet other embodiments, the at least one guard molecule may comprise a non-peptide compound. Any compounds that behave similarly (i.e. same hydrophobicity, same charge status at same pH, etc.) as the target peptide in sample preparation can work as a blocker to prevent nonspecific binding of the target peptides to the surfaces target peptides may interact, and also the guard compounds can be differentiated by analytical procedures, such as by sequence-specific antibody or a mass spectrometer by having a different mass and/or M/z.

According to certain embodiments of the method, the target peptide is a neoantigen peptide, and examples of the neoantigen peptide can include, without limitation, KRAS_Q61H, KRAS_Q61L, KRAS_Q61R, IDH2_R140Q, TP53_Y220C, TP53_R248W, TP53_R213L, KRAS_G12V_9mer, KRAS_G12V_10mer, KRAS_G12D_9mer, or KRAS_G12D_10mer. These examples will be covered in the Embodiment 1 of the disclosure as set forth below. It is noted that besides characterization of a neoantigen peptide, the method can also be applied to characterize other peptides that are not neoantigens. There is no limitation herein.

According to some embodiments of the method where the target peptide is a neoantigen peptide, the neoantigen peptide is from a tissue sample obtained from a subject, and the method further comprises a tissue sample preparation step prior to step (1) of introducing at least one guard molecule to mix with the target peptide. The tissue preparation step may comprise the following sub-steps:

(a) providing the tissue sample, wherein the tissue sample is a frozen tissue sample;

(b) grinding the frozen tissue sample, under an impact of at least 8,000 psi, to thereby obtain a frozen single-cell tissue powder; and (c) treating the frozen single-cell tissue powder before obtaining a treated tissue sample.

Herein, the subject can be a human, but can also be another mammal species, such as a monkey, an ape, a dog, a mouse, a rat, etc., yet can also be a non-mammal species. The tissue sample may be a surgical resection tumor sample, or may be a biopsy sample.

Herein, in sub-step (a) of the tissue sample preparation step, the tissue sample can be a frozen tissue sample, which preferably can be a tissue sample snap-frozen in liquid nitrogen. The tissue sample can be freshly obtained from a subject by biopsy or by surgical dissection, and can be an FFPE (Formalin Fixed Paraffin Embedded) tissue sample that is processed by liquid nitrogen before the sub-step (b) of grinding. Other forms the tissue sample are also possible and shall be deemed to be covered by the disclosure herein.

According to certain embodiments, the impact for grinding the frozen tissue sample in sub-step (b) can be approximately 10,000 psi. In other embodiments, the impact force can be approximately 12,000 psi, 15,000 psi, etc.

According to certain embodiments, the sub-step (c) of treating the frozen single-cell tissue powder before obtaining a treated tissue sample comprises: lysis, sonication, and centrifugation, and the treated tissue sample can be from a supernatant after the centrifugation.

In sub-step (c) of the tissue sample preparation step, the frozen single-cell tissue powder can be treated by tissue lysis to lyse the cells within the ground tissue sample, followed by sonication for fragmenting the genomic DNAs within the cells. After centrifuge, the supernatant becomes the treated tissue sample which contains the neoantigen peptide to be characterized. More details for the tissue sample preparation step can be found in Embodiment 1 of the disclosure.

According to certain embodiments, after the sub-step (c) of treating the frozen single-cell tissue powder before obtaining a treated tissue sample, the method can further comprise:

performing an analysis over genomic DNA obtained from a pellet after the centrifugation.

According to some embodiments, after the tissue sample preparation step and prior to step (1) of introducing at least one guard molecule to mix with the target peptide, the method further comprises an human leukocyte antigen (HLA) molecule enrichment step, comprising:

passing the treated tissue sample through an HLA enrichment column, wherein the HLA enrichment column comprises a matrix with anti-HLA antibodies immobilized thereon.

According to some embodiments, after the HLA molecules enrichment step, the method further comprises an elution step, comprising:

applying an elution buffer having a low pH to the HLA enrichment column to thereby obtain an eluate containing the neoantigen peptide.

Herein, the elution buffer comprises the at least one guard molecule.

According to some embodiments, after the elution step and prior to step (2) of applying the mass spectrometry analysis for the characterization of the target peptide, the method further comprises an clean-up step, comprising:

(a) passing the eluate through a trap column for at least one time to thereby trap the neoantigen peptide therewithin, wherein the trap column comprises a matrix capable of binding with the neoantigen peptide but having a lower or no binding affinity to impurities; and (b) eluting the trap column to thereby obtain a cleaned eluate.

According to some embodiments, after the clean-up step and prior to step (2) of applying the mass spectrometry analysis for the characterization of the target peptide, the method further comprises a purification step, comprising:

passing the cleaned eluate through a size exclusion column (SEC column, or SEC), for collecting a neoantigen peptide-containing fraction.

Herein optionally, before passing the cleaned eluate, the cleaned eluate can be spiked with a peptide ladder, such as NEO-SEC ladder described below, which is purported to define the boundaries for collecting the neoantigens. Specifically, signature chromatography peaks can be monitored to indicate the starting point (e.g. a peak representing 2000 Da in the example of NEO-SEC ladder) and the ending point (e.g. a peak representing 800 Da in the example of NEO-SEC ladder) for the collection.

Regarding the tissue preparation step, the HLA molecules enrichment step, the elution step, the clean-up step, the purification step, and the mass spectrometry analysis step of the method as set forth above, more details can be found in Embodiment 1 of the disclosure.

According to certain embodiments of the method, at least two consecutive steps of the HLA molecules enrichment step, the elution step, the clean-up step and the purification step can be operably connected, thereby substantially realizing an automatic processing with little or no human intervention.

According to certain embodiments, substantially all steps of the HLA molecules enrichment step, the elution step, the clean-up step and the purification step are operably connected, and are subs antically automatic.

According to preferred embodiments, the mass spectrometry analysis step whereby the neoantigen peptide-containing sample runs through a mass spectrometer, i.e. step (2) as mentioned above, may be further operably connected with the upstream purification step for automation. In other words, the whole sample processing procedure, including the HLA molecule enrichment step, the elution step, the clean-up step, the purification step, and the mass spectrometry analysis step, can realize an automation with little or no human intervention.

It is noted that each of these steps may not be limited to the steps disclosed herein, and can be realized by an alternative means that is known to people of ordinary skills in the art, yet by applying these steps as disclosed herein, an automation of the sample preparation, HLA molecules enrichment, elution, clean-up, purification, and mass spectrometry analysis can be realized. The integrated system and method, termed "Valid-NEO" pipeline, substantially requires little or no manual intervention, and thereby high sensitivity, reproducibility, and transplantability can be ensured across different diagnostic centers and hospitals.

In a second aspect, a system capable of implementing the method as set forth above is further provided. The system comprises the following components:

(1) a tissue sample grinding device, configured to apply an impact of at least 8,000 psi to the frozen tissue sample to thereby obtain the frozen single-cell tissue powder in the tissue sample preparation step;

(2) an HLA enrichment column, comprising matrix with anti-HLA antibodies immobilized thereon and configured to allow the treated tissue sample obtained in the tissue sample preparation step to pass therethrough so as to enrich the HLA molecules in the HLA molecules enrichment step;

(3) a trap column, comprising a matrix capable of binding with the neoantigen peptide but having a lower or no binding affinity to impurities and configured to trap the neoantigen peptide therewithin in the clean-up step;

(4) a size exclusion column (SEC), configured to purify the neoantigen peptide in the purification step; and (5) a mass spectrometer, configured to implement the mass spectrometry analysis step.

In Embodiment 1 of the disclosure, one embodiment of the tissue sample grinding device, termed "UniCeller", is described in more detail.

According to certain embodiments of the system, at least two neighbors of the HLA enrichment column, the trap column, the size exclusion column (SEC), and the mass spectrometer are sequentially and operably connected with one another to thereby allow an automation.

Yet according to certain embodiments, all of the HLA enrichment column, the trap column, the size exclusion column (SEC), and the mass spectrometer are sequentially and operably connected with one another to thereby allow an automation.

BRIEF DESCRIPTION OF THE DRAWINGS

FIGS. 3A-3F together show a table summarizing the cancer types of the patients, the selected genetic mutation features of their tumors, and the possible neoantigen sequences flanking the highest prevalence mutation site on a cancer driver gene;

FIG. 4 shows a comparison result of the protein extraction efficiencies between UniCeller and three other traditional approaches;

FIG. 5 shows reproducibility evaluation results of the Valid-NEO pipeline analysis.

DETAILED DESCRIPTION

In order to further describe the neoantigen analysis method and system as provided above, one specific embodiment (i.e. Embodiment 1) is provided below.

Embodiment 1

Figure 1:
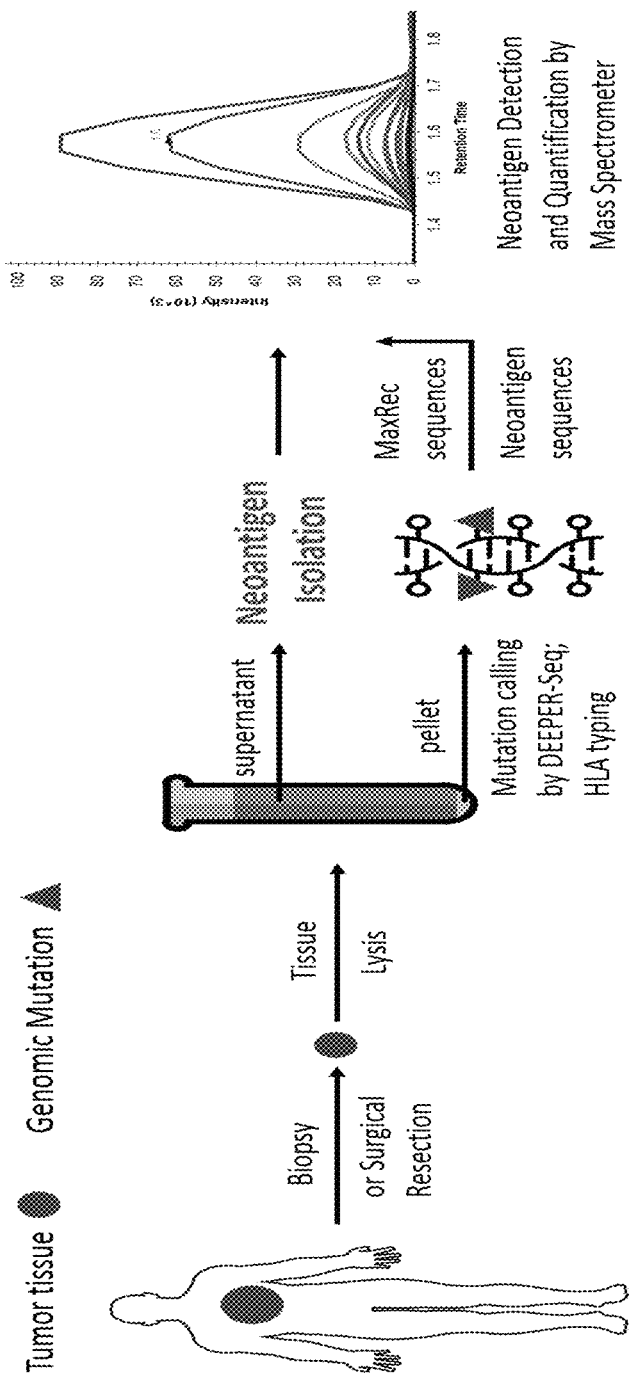
FIG. 1 illustrates a general process for the Valid-NEO pipeline according to certain embodiments of the disclosure.

FIG. 1 illustrates a general process for the Valid-NEO pipeline to analyze a neoantigen peptide. Specifically, tumor tissue specimen from a subject is first harvested through biopsy or surgical resection, which is then processed, through tissue lysis, sonication and centrifuge, to obtain HLA molecules (in supernatant) and genomic DNA (in pellet). Patient specific mutations were revealed through genomic sequencing of the tumor DNA from the pellet by DEEPER-Seq pipeline (Wang et al., 2017). Mutation callings are made and potential sequences for neoantigens and neoantigen peptides (called "MaxRec sequences") were established. Neoantigens are then isolated and purified from tissue lysate supernatant through a multi-step procedure which is illustrated in FIGS. 2A and 2B and described below, then neoantigens are directly detected and quantified through mass spectrometry.

Figure 2A:
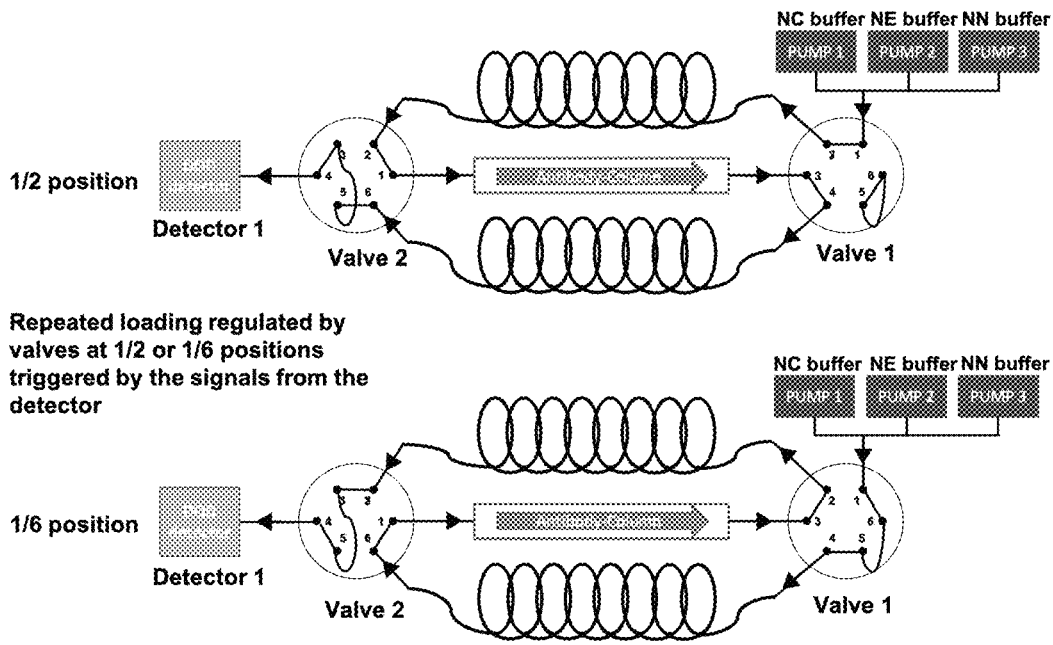
FIG. 2A and FIG. 2B together illustrate a scheme of neoantigen isolation and purification in the Valid-NEO pipeline according to certain embodiments of the disclosure.
Figure 2A:
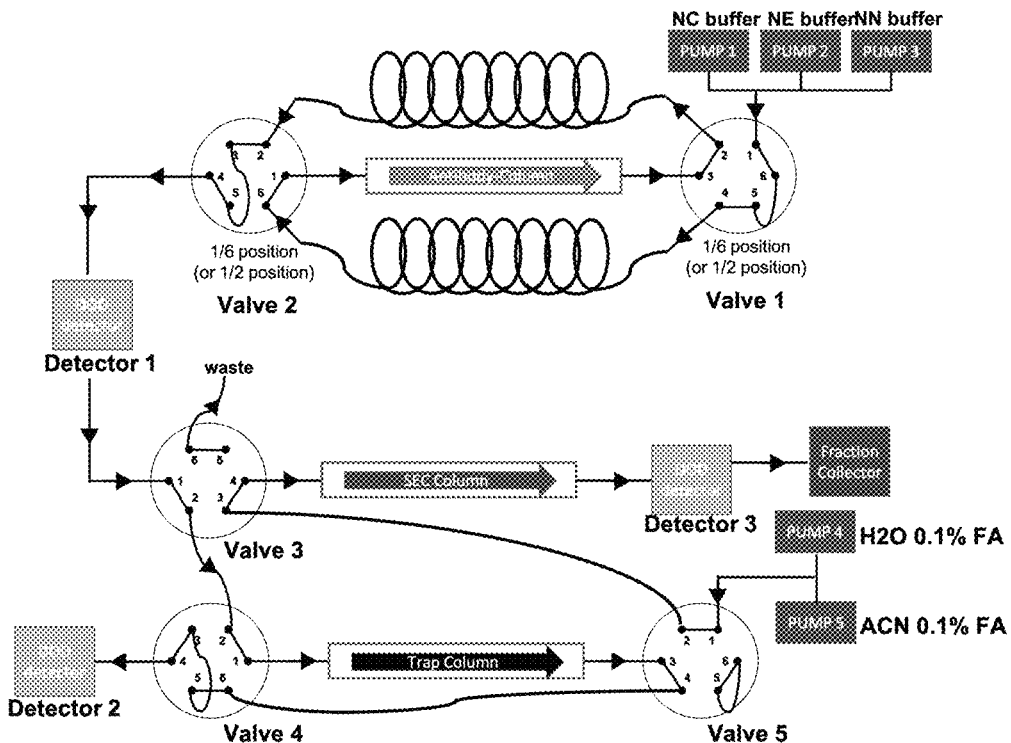
Figure 2B:
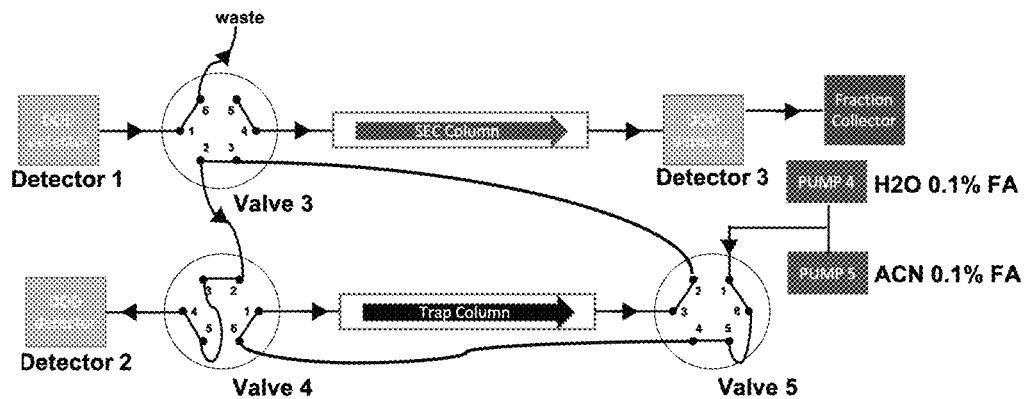
Figure 2B:
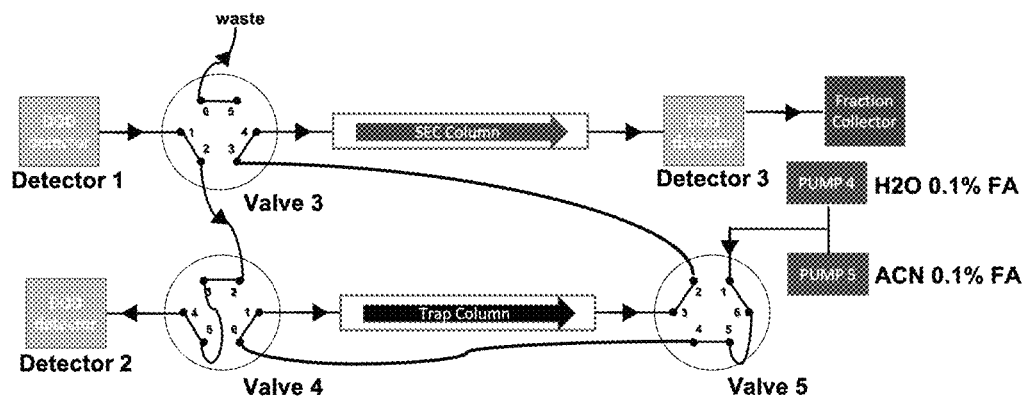
Figure 2B:
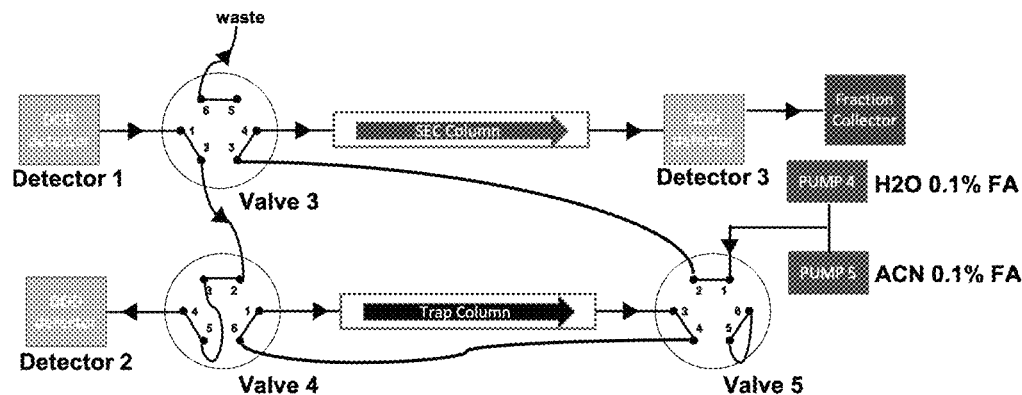

FIGS. 2A and 2B illustrate a scheme of the multi-step process of neoantigen isolation and purification in the Valid-NEO pipeline according to certain embodiments of the disclosure. As illustrated in the two figures, there are mainly 5 steps in Valid-NEO system to obtain neoantigens, Step 1) HLA enrichment by antibody column with repeated loading; Step 2) Elution of HLA molecules and separation of neoantigens followed by trap column loading; Step 3) Neoantigen clean up and removal of HLA molecules; Step 4) Neoantigen elution and loading of SEC column; Step 5) Purification of neoantigens through SEC column.

In this embodiment of the multi-step process for neoantigen isolation and purification in the Valid-NEO pipeline, it is noted that a series of valves (see "Valves 1-5" in the figure), a series of pumps (see PUMPS 1-5), a series of DAD detectors (see "Detectors 1-3), and a Fraction Collector, are also included in the system. The schematic configuration and connection for each component in the system is also illustrated in FIGS. 2A and 2B.

As illustrated, each valve comprises a total of 6 ports (#1-6), each operably and controllably connected to an inlet or an outlet of other devices, such as the "Antibody Column" (i.e. HLA enrichment column), the "Trap Column", the "SEC Column", the pumps, DAD detectors, and the Fraction Collector. Each pump is configured to provide a driving force that drives the fluid to flow in the pipeline in a predetermined direction (as shown by the arrows in the figure), and each port is configured to open or close in a controlled manner based on the control signals that it receives. Each of the DAD detectors is configured to detect certain parameter of the fluid that it receives. A processor (not shown) is communicatively connected to each of the above components, and is configured, based on the detection signals transmitted from the DAD detectors, to control the coordinated working of each of the above components in a programed manner. For example, the processor may control the opening/closing status of each port of the valves, and may control the start or stop and flow rate of the each pump. As such, the coordinated working of each component of the system can realize an automatic sample processing, allowing the treated tissue sample (i.e. HLA/neoantigen-containing sample, or the "supernatant" in FIG. 1) to flow through the enrichment column, the trap column, and the SEC column in an automatic and controlled manner before running into the mass spectrometer for characterization.

Materials and Methods

Tumor Samples

Tumor samples from a total of 10 patients were obtained from BioIVT. This study was approved by the Institutional Review Boards for Human Research at Complete Omics Inc. and BioIVT, and complied with Health Insurance Portability and Accountability Act. Cancer types of the patients and selected genetic mutation features of their tumors are listed in the table shown in FIGS. 3A-3F. In the table, the amino acid residues in bold and underlined font represent the mutations of interest in a neoantigen peptide sequence.

Construction of Valid-NEO

Valid-NEO is an integrated system composed of five steps essential for neoantigen detection, including 1) Enrichment of HLA molecules, 2) Elution of neoantigens from antibody column, 3) Cleaning of neoantigens, 4) Elution of neoantigens from trap column, 5) Purification of neoantigens through SEC column. This integrated system is composed of a tandem series of HPLC systems, one mass spectrometer, and a set of optimized buffers including the MaxRec system.

HLA Molecule Extraction from Tissue Sample

Human tumor fresh frozen tissues were obtained from BioIVT (BioIVT, NY). 50 mg frozen tissue were wrapped in aluminum foil such that the tissue chunk was covered by at least four layers of aluminum foil. The wrapped tissue chunk was snap-frozen in liquid nitrogen. UniCeller (Complete Omics Inc, MD), an in-house built device designed to apply strong impact onto frozen tissue packs, was used to produce single-cell level powder from the tissue chunk, and this procedure can be repeated 5 times until the tissue chunk is completely ground into frozen single-cell powder. 1 mL NL buffer (Complete Omics Inc, MD) was added to the tissue powder and the tissue suspension was transferred into a protein lo-bind tube followed by five rounds of sonications through Bioruptor 300 (energy level 4.5, duty step 30 seconds, and delay step 59 seconds). The tissue lysate was incubated on ice for 1 hour, during which the suspension was pipetted up and down 20 times every 10 minutes, and one additional cycle of sonication was performed every 10 minutes. The tissue lysate was centrifuged at 4° C. for 30 minutes, and the clear supernatant was transferred to a new protein lo-bind tube. The supernatant containing HLA molecules was diluted with 4 volumes of NC buffer (Complete Omics Inc., MD), after which it was ready for HLA molecule isolation.

Online Enrichment of HLA Molecules Through Antibody-Column

Anti-HLA antibodies (clone W6/32) were immobilized on Protein A agarose beads (ThermoFisher Scientific, MA) through DMP (dimethyl pimelimidate)-based crosslinking reaction. 50 mL beads were then packed into an HLA enrichment column and flushed with 1 L NC buffer (Complete Omics Inc, MD). HLA-neoantigen suspension was filtered through a 0.22 μm filter, diluted with 4 volumes of the NC buffer and injected directly onto the HLA enrichment column. The flow-through was collected into a sample loop and re-injected onto the column. The injection was repeated for 4 more times, for a total of 5 passes of the suspension through the antibody column. During the repeated loadings, HLA molecules were depleted from the mobile phase and captured by the column, while the HLA-suspension was gradually diluted by NC buffer pushed into the system by the pump. The repeated loading ensured an efficient binding of the HLA molecules to the column and the sequential dilution of the sample with the mobile phase facilitates an improved cleaning efficiency and reduced nonspecific binding. The antibody column was then flushed with NC buffer at 1 mL/min for 20 minutes to remove unbound proteins and impurities (including salts and detergents).

Online Elution of Neoantigen Peptides and Antibody Column Regeneration

Elution of the neoantigen peptides was performed with an increasing gradient (from 0 to 100% over a period of 5 minutes) of NE buffer (Complete Omics Inc, MD) through the column, followed by a constant flush with 100% NE buffer at 1 mL/min for 2 minutes. The antibody column was then neutralized by running an increasing gradient (from 0 to 100% over a period of 5 minutes) of NN buffer (Complete Omics Inc, MD), and followed by a 1 hour flushing with NC buffer at 1 mL/min. The eluted HLA molecules and neoantigen peptides were then subjected to further purifications.

Online Isolation and Purification of Neoantigen Peptides

HLA eluate containing neoantigen peptides was injected to pass through a trap column for a total of 5 times, followed by washing with 10 mL 0.1% formic acid. The cleaned peptides were eluted from the trap column through three cycles of acetonitrile gradients using mobile phase solvent A: 0.1% formic acid in water and mobile phase solvent B: 0.1% formic acid in acetonitrile. The gradient started from 0% solvent B and increased to 60% solvent B over 30 seconds, and then decreased to 0% solvent B over 30 seconds, and this 1-min gradient step was repeated three times at the follow rate of 1 mL/min followed by a high-speed flush at 2 mL/min with 100% solvent B for 1 minute. The follow through was collected 30 seconds after the initial gradient change took place and the collection was stopped 1 minute after the flushing step ended. A total of 4.5 mL of neoantigen peptide suspension was collected with an estimated 30% acetonitrile and 0.1% formic acid. The collected neoantigen suspension was directly loaded onto an SEC column packed with 1.7 μm particles with 125 Å pore size (Waters, MA). Before the analysis, NEO-SEC ladder (Complete Omics, MD) was spiked into the system to define the boundaries for collecting the neoantigens. Signature chromatography peaks were monitored to indicate the starting point (a peak representing 2000 Da) and the ending point (a peak representing 800 Da) for the collection. Flow-through containing the isolated neoantigen peptides was collected and subject to lyophilization before mass spectrometry analysis.

Mass Spectrometry Method Development

Heavy isotope labeled neoantigen peptides flanking gene mutations in patient cancer genomes were synthesized. Optimization of the detection parameters was performed with a two-step approach. Step 1) All possible ions (first to last) of each peptide were detected with a theoretical collision energy as well as two additional collision energies at 5 eV below and above the theoretical value (three collision energy values in total for each transition). The highest abundance transitions were selected for the next round of optimization. Step 2) High abundance transitions selected from previous step (>20 transitions for each charge status of the peptide target) were subject to a further optimization where for each transition 9 collision energy values were tested including the theoretical collision energy value as well as 4 steps of values below and above the theoretical value with a step-size of 2 eV. After two rounds of optimizations, detection parameters were manually curated to avoid false positive signals from co-detected impurities in the Valid-NEO matrix prepared from a reference human tumor sample, and an average of 8 to 10 transitions were selected as signature transitions for each target. Before and after each batch of analysis, Agilent 6495C Triple Quadrupole mass spectrometer was tuned using manufacturer's tuning mixture followed by MyProt-SRM Tuning Booster (Complete Omics, MD). Before each assay, to ensure the stable and consistent performance of the mass spectrometer throughout the entire study, MyProt-SRM Performance Standard (Complete Omics, MD), a mixture of standard peptides across a wide range of masses (M/z 100-1400) and a broad range of hydrophobicities, were analyzed. A system performance score was documented before every run.

Pre-Conditioning the System to Ensure Highest Sensitivity

In order to achieve the highest sensitivity for the assay, a strategy is developed to ensure a minimal sample loss by pre-conditioning and co-processing in the system with peptides that are "similar" to the ones being detected. The peptides used to ensure the maximal recovery of the assay are called MaxRec peptides. A MaxRec prediction algorithm was created to generate MaxRec peptide sequences based on the sequences, hydrophobicity and detectability (signal strengths detected in mass spectrometer) of the target peptides desired to be detected from the pipeline. MaxRec peptide sequences used in this study were shown in Table 1, where the amino acid residues in bold and underlined font represent the mutations of interest (i.e. target mutations), and the amino acid residues in italics font represent the altered residues used in the MaxRec peptides. All MaxRec peptides were synthesized at a high purity (>99.9%). A buffer system containing MaxRec peptides at the concentration of 100 femtomole/μL was injected into the Valid-NEO pipeline before each assay. MaxRec peptides passed through the pipeline at much higher concentrations than what would presumably be observed from the target peptides in clinical samples. Before clinical sample injection, the Valid-NEO pipeline was flushed with NC buffer for 30 minutes to deplete excessive unbound MaxRec peptides.

TABLE 1

MaxRec peptides used in this study

| ID | Neo-antigen peptide sequence | MaxRec peptides | | |
|---|---|---|---|---|
| KRAS_Q61H | ILDTAGHEEY (SEQ ID NO. 496) | ILDTAGH_D_EY (SEQ ID NO. 507) | I_V_DTAGHEEY (SEQ ID NO. 518) | ILD_S_AGHEEY (SEQ ID NO. 529) |
| KRAS_Q61L | ILDTAGLEEY (SEQ ID NO. 497) | ILDTAGL_D_EY (SEQ ID NO. 508) | I_V_DTAGLEEY (SEQ ID NO. 519) | ILD_S_AGLEEY (SEQ ID NO. 530) |
| KRAS_Q61R | ILDTAGREEY (SEQ ID NO. 498) | ILDTAGRE_D_Y (SEQ ID NO. 509) | I_V_DTAGREEY (SEQ ID NO. 520) | ILD_S_AGREEY (SEQ ID NO. 531) |
| IDH2_R140Q | SPNGTIQNIL (SEQ ID NO. 499) | SPN_A_TIQNIL (SEQ ID NO. 510) | SPNGTIQNI_V_ (SEQ ID NO. 521) | SPNGT_V_QNIL (SEQ ID NO. 532) |
| TP53_Y220C | VVPCEPPEV (SEQ ID NO. 500) | VVPCEPP_D_V (SEQ ID NO. 511) | VVPCEPPE_L_ (SEQ ID NO. 522) | V_I_PCEPPEV (SEQ ID NO. 533) |
| TP53_R248W | SSCMGGMNWR (SEQ ID NO. 501) | SSCM_A_GMNWR (SEQ ID NO. 512) | S_T_CMGGMNWR (SEQ ID NO. 523) | SSCMGGM_Q_WR (SEQ ID NO. 534) |
| TP53_R213L | YLDDRNTFL (SEQ ID NO. 502) | YL_E_DRNTFL (SEQ ID NO. 513) | YLDDRNTF_V_ (SEQ ID NO. 524) | YLDDRN_S_FL (SEQ ID NO. 535) |
| KRAS_G12V_9mer | VVGAVGVGK (SEQ ID NO. 503) | VVGAVG_L_GK (SEQ ID NO. 514) | VVGAV_A_VGK (SEQ ID NO. 525) | VVG_G_VGVGK (SEQ ID NO. 536) |
| KRAS_G12V_10mer | VVVGAVGVGK (SEQ ID NO. 504) | VVVGAVG_L_GK (SEQ ID NO. 515) | VVVGAV_A_VGK (SEQ ID NO. 526) | VVVG_G_VGVGK (SEQ ID NO. 537) |
| KRAS_G12D_9mer | VVGADGVGK (SEQ ID NO. 505) | VVGADG_L_GK (SEQ ID NO. 516) | VVGAD_A_VGK (SEQ ID NO. 527) | VVG_G_DGVGK (SEQ ID NO. 538) |
| KRAS_G12D_10mer | VVVGADGVGK (SEQ ID NO. 506) | VVVGADG_L_GK (SEQ ID NO. 517) | VVVGAD_A_VGK (SEQ ID NO. 528) | VVVG_G_DGVGK (SEQ ID NO. 539) |

Data Deposition

The data reported in this article have been deposited via ProteomeXchange in
PeptideAtlas SRM Experiment Library (PASSEL) (identifier PASS01588).

Results

To maximize the recovery of HLA molecules from tumor tissue samples, it is critical to homogenize the frozen tissue into single-cell powder rapidly without thawing the sample. For this purpose, an equipment, called the "UniCeller", was developed, which is capable of applying a strong impact (~10,000 psi) to frozen tissue chunks. Tissue powder was produced through UniCeller and was then quickly dissolved in Neoantigen Lysis (NL) buffer (Materials and Methods), followed by repeated pipetting and programmed sonication (Materials and Methods). Through this procedure, it was shown that nearly 100% of the HLA molecules from the tissue sample was able to be extracted, which represents a greater recovery efficiency than when using traditional approaches including Dounce Homogenizer, Probe Sonicator and Bead Ruptor (see FIG. 4, which shows a comparison results of the recovery efficiencies between UniCeller and three other traditional approaches Specifically for the experiment, the same amount (50 mg) of tumor tissue was processed through different approaches, including using Dounce Homogenizer, Probe Sonicator, Bead Ruptor, and UniCeller, for extracting HLA complexes. W6/32 antibody was used for the blot). The higher yield observed when using the UniCeller suggests that HLA molecule, as a protein complex predominantly located on the cell surface, may be vulnerable to temperature change and harsh mechanical force in liquid suspension during extraction. In addition, few to none HLA molecules were left in the pellet from the UniCeller group, indicating that a higher extraction efficiency can be achieved when a strong mechanical impact is applied to rapidly generate single-cell level dry tissue powder, followed immediately by a moderate but repeated HLA extraction in lysis buffer.

The pellet obtained from the UniCeller tissue lysate was processed to extract genomic DNA (see FIG. 1). Single-stranded exomic regions of a selected panel of cancer driver genes were captured with proprietary dual RNA probes and sequenced through DEEPER-Seq pipeline (Wang et al., 2017). A mutation calling was made only when the point mutation is observed as a complementary pair of residues on both DNA strands came from the same DNA duplex molecule as previously described (Wang et al., 2017). Nine tumor samples bearing hotspot mutations in highly frequently mutated cancer driver genes K-Ras and TP53, as well as the slightly lower frequently mutated driver gene IDH2 were selected for a further evaluation of potential neoantigen presentations.

Antibody-column based affinity chromatography is more efficient and cost-effective than conventional immunoprecipitation and was thus adopted in Valid-NEO pipeline for enriching HLA molecules (Moser & Hage, 2010). To achieve a high enrichment efficiency, an antibody-conjugated column was packed with a 20-fold excess of antibodies (50 mg antibody) relative to the amount needed to enrich HLA molecules from a typical sample (50-100 mg wet tissue with ≥50% tumor mass), in addition repeated sample loadings were performed to ensure the binding between antibodies and HLA molecules in Neoantigen Capture (NC) buffer (see FIGS. 2A and 2B, Materials and Methods). Through elution from the column and incubation in acidic Neoantigen Elution (NE) buffer (Materials and Methods), HLA complexes were eluted, and neoantigen peptides were dissociated from HLA molecules (see FIGS. 2A and 2B). The HLA enrichment column was then regenerated by Neoantigen Neutralization (NN) buffer. The column can be used for at least 30 enrichment and elution procedure with no significant loss in performance observed for the neoantigens analyzed in this study (see FIG. 5, which shows reproducibility evaluation results of the Valid-NEO pipeline analysis. Specifically for the experiment, 10 tumor samples were processed through the same NeoTrue Valid-NEO pipeline to evaluate their endogenous neoantigen presentations. For each neoantigen, three replicates NeoTrue Valid-NEO assays were performed. There were 9 NeoTrue Valid-NEO assays for different neoantigens between replicate 1 and 2, as well as between replicate 2 and 3 for the detection of each neoantigen).

Figure 6:
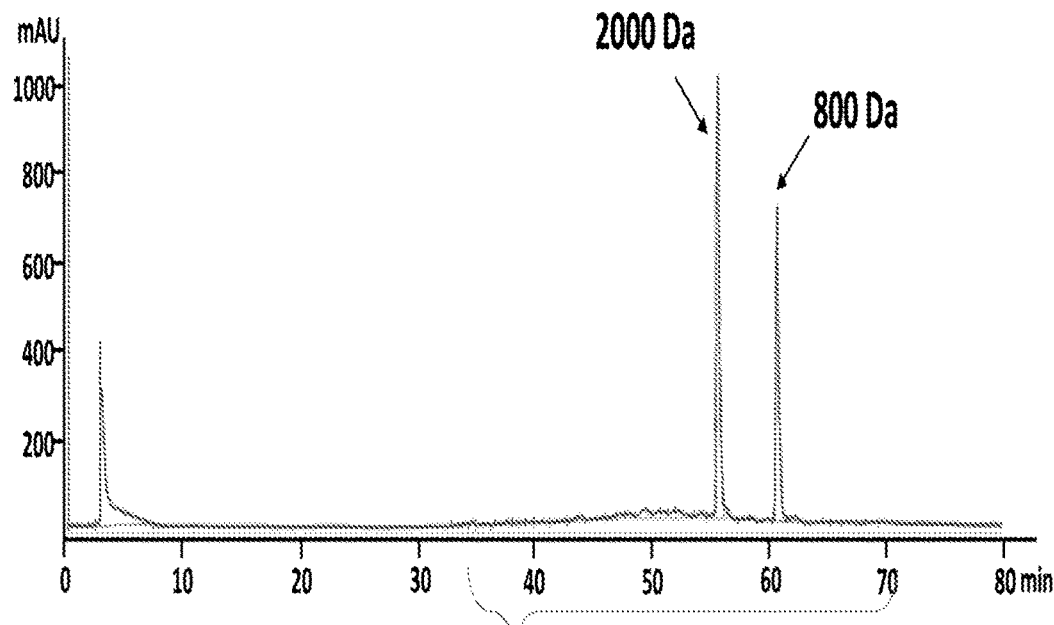
FIG. 6 shows HPLC chromotograms for neoantigen purification through an SEC column.
Figure 6:
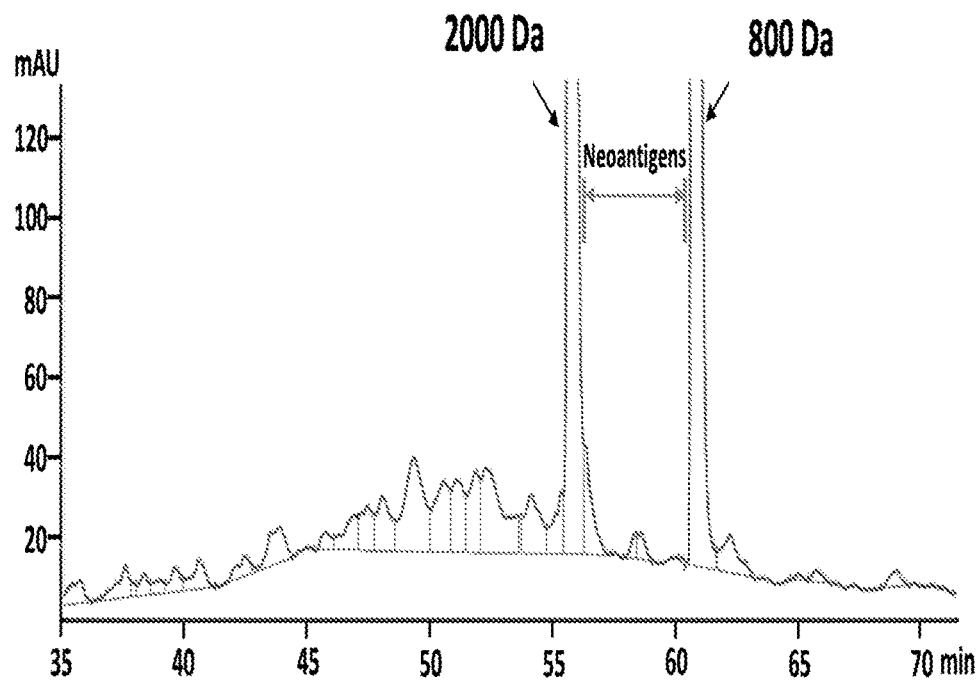

HLA molecules and other large proteins were separated from neoantigen peptides by a trap column packed with C18 small pore spherical silica particles (diameter 100 Å). Neoantigens (molecular weight around 1.5 kDa) are significantly smaller than HLA molecules (molecular weight around 41 kDa), and will enter the pores therefore be efficiently retained by the C18 matrix that are predominately located inside the pores. The majority of HLA molecules and other large proteins are not efficiently retained by the column. Neoantigens bound to the trap column were then cleaned with 0.1% formic acid to remove HLA molecules and other impurities (see FIGS. 2A and 2B). Neoantigens were then eluted into a suspension composed of 30% acetonitrile 0.1% formic acid. The suspension was spiked with NEO-SEC ladder (Complete Omics Inc, MD), containing two sets of peptides with signature molecular weights at 2,000 and 800 Da (Materials and Methods), and subjected to fractionation through a size exclusion column (short as SEC or SEC column hereinafter) (see FIGS. 2A and 2B). During elution, absorbance at the wavelength of 280 nm was constantly measured by a diode array detector (i.e. DAD). Neoantigen fraction started to be collected after a signature peak at 2,000 Da was observed, and the collection stopped before an 800 Da signature peak was observed (see FIG. 6, which shows HPLC chromatograms for neoantigen purification through an SEC column. Specifically, neoantigen samples were loaded to SEC column together with NEO-SEC ladders. Two signature peaks were observed at 2000 Da and 800 Da, which marked the boundaries for neoantigen-containing fractions). The flow-through between the two signature peaks was collected and lyophilized. The neoantigen sample was then subjected to Valid-NEO mass spectrometry analysis with pre-optimized conditions (Materials and Methods).

To further improve the recovery ratio and the sensitivity of the pipeline, a neoantigen recovery system, called "Maximum Recovery (MaxRec) System", was developed. A key element in MaxRec is a set of peptides with slightly different sequences (varying by only 1 or 2 amino acids) from the target peptides, and they are resuspended in the MaxRec system at a much higher abundance than the endogenous neoantigens. MaxRec peptides are designed to mimic the physical characteristics of the target peptides, so as to saturate the nonspecific binding opportunities in the system, thereby minimizing the loss of the target peptides due to such nonspecific interactions. Though sharing similar physical characteristics as target peptides, MaxRec peptides are chemically different, and can be easily distinguished from neoantigen targets based on the high resolution of modern mass spectrometers (see FIGS. 2A and 2B). The Triple Quadrupole Mass Spectrometer in Valid-NEO system is set up to be completely blind to MaxRec peptides and the presence of MaxRec system will not reduce the sensitivity of the platform, which is a feature of such type of instrument. The Valid-NEO neoantigen isolation system was pre-conditioned and spiked in the samples with the MaxRec peptides (see Table 1 above). Through MaxRec system, a significantly improved performance was able to be achieved in the detection of all neoantigen peptides in this study with an average increase in sensitivity by 27 folds (ranging from 2 to 67 folds) (the results are shown in Table 2 below).

patient's individual genetic background of the disease (Bonadonna & Valagussa, 1983; Chan et al., 2012; Savage et al., 2009; Yagoda & Petrylak, 1993). While cytotoxic chemotherapies are still the first line treatment for many cancers, further molecular characterization of cancers has facilitated the development of small molecules or antibody-based agents that can treat a sub-population of the patients who are sharing the same genetic basis of their diseases (Sawyers, 2004; Scaltriti & Baselga, 2006; Sharkey & Goldenberg, 2006). With the development of next-generation sequencing (NGS), it is evident that each individual's cancer has its own genetic profile with varying degrees of

TABLE 2

Neoantigen quantification through different approaches

| | Valid-NEO | Valid-NEO (w/MaxRec) | | |
| --- | --- | --- | --- | --- |
| Neoantigen | MANA-SRM Detected Ratio to Standards | (w/o MaxRec) Detected Ratio to Standards | Detected Ratio to Standards | detected abundance (unit: atto mole) | copy number per tumor cell (assuming 50 M cells) |
| KRAS_Q61H | non-detectable ± N/A | 0.022 ± 0.006 | 1.045 ± 0.058 | 522.5 | 6.3 |
| KRAS_Q61L | 0.027 ± 0.002 | 0.053 ± 0.004 | 0.729 ± 0.037 | 364.5 | 4.4 |
| KRAS_Q61R | non-detectable ± N/A | 0.04 ± 0.004 | 1.495 ± 0.156 | 747.5 | 9.0 |
| IDH2_R140Q | non-detectable ± N/A | 0.015 ± 0.003 | 1.019 ± 0.057 | 509.5 | 6.1 |
| TP53_R175H | 0.042 ± 0.004 | 0.266 ± 0.011 | 1.006 ± 0.045 | 503 | 6.1 |
| TP53_Y220C | non-detectable ± N/A | 0.054 ± 0.002 | 1.354 ± 0.014 | 677 | 8.2 |
| TP53_R248W | 0.011 ± 0.00006 | 0.086 ± 0.034 | 0.173 ± 0.031 | 86.5 | 1.0 |
| TP53_R213L | non-detectable ± N/A | 0.373 ± 0.057 | 0.662 ± 0.03 | 331 | 4.0 |
| KRAS_G12V_9 mer | non-detectable ± N/A | 0.146 ± 0.022 | 5.458 ± 1.206 | 2729 | 32.9 |
| KRAS_G12V_10 mer | non-detectable ± N/A | 0.141 ± 0.024 | 6.381 ± 1.693 | 3190.5 | 38.4 |
| KRAS_G12D_9 mer | 0.0719 ± 0.012 | 0.145 ± 0.067 | 2.933 ± 1.227 | 1466.5 | 17.7 |
| KRAS_G12D_10 mer | 0.113 ± 0.012 | 0.244 ± 0.104 | 6.518 ± 3.748 | 3259 | 39.3 |

It has been shown that almost all MHC class I associated neoantigens have a length between 8 to 12 amino acids (Sarkizova et al., 2020). For each sample, all potential neoantigen sequences flanking the highest prevalence mutation site on a cancer driver gene (a maximum of 50 possible neoantigen peptides for each missense mutation site) can be directly assayed for in a massively parallel manner without any prediction thus preventing uncertainties (see the table shown in FIGS. 3A-3F). Using Valid-NEO pipeline, nine fresh frozen tumor samples was analyzed to detect and quantify each patient's personalized neoantigens and compared their relative performance between MANA-SRM and the current integrated Valid-NEO pipeline (see Table 2). The patients with KRAS mutations at Q61 site have on average 6.6 copies of the neoantigen presented on each tumor cell surface, and the neoantigens flanking G12 site has an average of 32.1 copies presented per tumor cell. The presentation of TP53 neoantigens are low, ranging from 1 to 8 copies per cell, similar to IDH2 mutations with 6.1 copies of neoantigens presented per cell. Each assay was performed for three times, and the reproducibility of the pipeline was thoroughly evaluated (see Table 2, FIG. 5).

Discussion

Traditionally, cytotoxic chemotherapies have been the mainstay therapeutic agent for cancers, regardless of a given overlaps in cancer driver gene mutations among patients (Bagnyukova et al., 2010; Cancer Genome Atlas Research et al., 2013; Chin et al., 2011; Vogelstein et al., 2013). In recent years, highly personalized cancer therapeutic approaches have achieved success through targeting a patient's specific neoantigens, offering hope with regards to the generalizability of such highly personalized treatments (Ott et al., 2017; Sahin et al., 2017). To reveal the neoantigen sequences needed for such personalized cancer therapeutics, algorithm-based or artificial intelligence (AI)-based predictions are often the choice when direct observation is impossible, but such predictions have been proven to be unreliable for clinical applications (Jurtz et al., 2017; Wang et al., 2019). Neoantigens can also be determined through co-culturing tumor cells with autologous T cells, followed by tetramer staining or peptide-pulsing assays, however these functional assays are technically difficult and time consuming, therefore cannot be readily adopted in clinical settings (Danilova et al., 2018; Lu et al., 2014). In Valid-NEO, no prediction is needed, and no cell culture is performed. Additionally, while the neoantigens evaluated in this study are all presented in the context of class I major histocompatibility complexes (MHC I), a similar concept can be readily applied to class II MHC as previously described (Wang et al., 2019).

Valid-NEO is the only pipeline developed so far to directly validate neoantigens from clinical samples in a sensitive, rapid and reproducible manner, and it helps pave the way for truly personalized cancer therapeutics.

REFERENCES

1. Bache, N., Geyer, P. E., Bekker-Jensen, D. B., Hoerning, O., Falkenby, L., Treit, P. V., Doll, S., Paron, I., Muller, J. B., Meier, F., Olsen, J. V., Vorm, O., & Mann, M. (2018, November). A Novel LC System Embeds Analytes in Pre-formed Gradients for Rapid, Ultra-robust Proteomics. *Mol Cell Proteomics*, 17(11), 2284-2296.
2. Bagnyukova, T. V., Serebriiskii, I. G., Zhou, Y., Hopper-Borge, E. A., Golemis, E. A., & Astsaturov, I. (2010, Nov. 1). Chemotherapy and signaling: How can targeted therapies supercharge cytotoxic agents? *Cancer Biol Ther*, 10(9), 839-853.
3. Bassani-Sternberg, M., Braunlein, E., Klar, R., Engleitner, T., Sinitcyn, P., Audehm, S., Straub, M., Weber, J., Slotta-Huspenina, J., Specht, K., Martignoni, M. E., Werner, A., Hein, R., D, H. B., Peschel, C., Rad, R., Cox, J., Mann, M., & Krackhardt, A. M. (2016, Nov. 21). Direct identification of clinically relevant neoepitopes presented on native human melanoma tissue by mass spectrometry. *Nat Commun*, 7, 13404.
4. Bekker-Jensen, D. B., Martinez-Val, A., Steigerwald, S., Ruther, P., Fort, K. L., Arrey, T. N., Harder, A., Makarov, A., & Olsen, J. V. (2020, April). A Compact Quadrupole-Orbitrap Mass Spectrometer with FAIMS Interface Improves Proteome Coverage in Short LC Gradients. *Mol Cell Proteomics*, 19(4), 716-729.
5. Bonadonna, G., & Valagussa, P. (1983, March). Chemotherapy of breast cancer: current views and results. *Int J Radiat Oncol Biol Phys*, 9(3), 279-297.
6. Cancer Genome Atlas Research, N., Weinstein, J. N., Collisson, E. A., Mills, G. B., Shaw, K. R., Ozenberger, B. A., Ellrott, K., Shmulevich, I., Sander, C., & Stuart, J. M. (2013, October). The Cancer Genome Atlas Pan-Cancer analysis project. *Nat Genet*, 45(10), 1113-1120.
7. Chan, D. L., Morris, D. L., Rao, A., & Chua, T. C. (2012). Intraperitoneal chemotherapy in ovarian cancer: a review of tolerance and efficacy. *Cancer Manag Res*, 4, 413-422.
8. Chin, L., Andersen, J. N., & Futreal, P. A. (2011, March). Cancer genomics: from discovery science to personalized medicine. *Nat Med*, 17(3), 297-303.
9. Danilova, L., Anagnostou, V., Caushi, J. X., Sidhom, J. W., Guo, H., Chan, H. Y., Suri, P., Tam, A., Zhang, J., Asmar, M. E., Marrone, K. A., Naidoo, J., Brahmer, J. R., Forde, P. M., Baras, A. S., Cope, L., Velculescu, V. E., Pardoll, D. M., Housseau, F., & Smith, K. N. (2018, August). The Mutation-Associated Neoantigen Functional Expansion of Specific T Cells (MANAFEST) Assay: A Sensitive Platform for Monitoring Antitumor Immunity. *Cancer Immunol Res*, 6(8), 888-899.
10. Douglass, J., Hsiue, E. H., Mog, B. J., Hwang, M. S., DiNapoli, S. R., Pearlman, A. H., Miller, M. S., Wright, K. M., Azurmendi, P. A., Wang, Q., Paul, S., Schaefer, A., Skora, A. D., Molin, M. D., Konig, M. F., Liu, Q., Watson, E., Li, Y., Murphy, M. B., Pardoll, D. M., Bettegowda, C., Papadopoulos, N., Gabelli, S. B., Kinzler, K. W., Vogelstein, B., & Zhou, S. (2021, Mar. 1). Bispecific antibodies targeting mutant RAS neoantigens. *Sci Immunol*, 6(57).
11. Hsiue, E. H., Wright, K. M., Douglass, J., Hwang, M. S., Mog, B. J., Pearlman, A. H., Paul, S., DiNapoli, S. R., Konig, M. F., Wang, Q., Schaefer, A., Miller, M. S., Skora, A. D., Azurmendi, P. A., Murphy, M. B., Liu, Q., Watson, E., Li, Y., Pardoll, D. M., Bettegowda, C., Papadopoulos, N., Kinzler, K. W., Vogelstein, B., Gabelli, S. B., & Zhou, S. (2021, Mar. 1). Targeting a neoantigen derived from a common TP53 mutation. *Science*.
12. Jurtz, V., Paul, S., Andreatta, M., Marcatili, P., Peters, B., & Nielsen, M. (2017, Nov. 1). NetMHCpan-4.0: Improved Peptide-MHC Class I Interaction Predictions Integrating Eluted Ligand and Peptide Binding Affinity Data. *J Immunol*, 199(9), 3360-3368.
13. Lauss, M., Donia, M., Harbst, K., Andersen, R., Mitra, S., Rosengren, F., Salim, M., Vallon-Christersson, J., Torngren, T., Kvist, A., Ringner, M., Svane, I. M., & Jonsson, G. (2017, Nov. 23). Mutational and putative neoantigen load predict clinical benefit of adoptive T cell therapy in melanoma. *Nat Commun*, 8(1), 1738.
14. Lu, Y. C., Yao, X., Crystal, J. S., Li, Y. F., El-Gamil, M., Gross, C., Davis, L., Dudley, M. E., Yang, J. C., Samuels, Y., Rosenberg, S. A., & Robbins, P. F. (2014, Jul. 1). Efficient identification of mutated cancer antigens recognized by T cells associated with durable tumor regressions. *Clin Cancer Res*, 20(13), 3401-3410.
15. Meier, F., Brunner, A. D., Koch, S., Koch, H., Lubeck, M., Krause, M., Goedecke, N., Decker, J., Kosinski, T., Park, M. A., Bache, N., Hoerning, O., Cox, J., Rather, O., & Mann, M. (2018, December). Online Parallel Accumulation-Serial Fragmentation (PASEF) with a Novel Trapped Ion Mobility Mass Spectrometer. *Mol Cell Proteomics*, 17(12), 2534-2545.
16. Moser, A. C., & Hage, D. S. (2010, April). Immunoaffinity chromatography: an introduction to applications and recent developments. *Bioanalysis*, 2(4), 769-790.
17. Ott, P. A., Hu, Z., Keskin, D. B., Shukla, S. A., Sun, J., Bozym, D. J., Zhang, W., Luoma, A., Giobbie-Hurder, A., Peter, L., Chen, C., Olive, O., Carter, T. A., Li, S., Lieb, D. J., Eisenhaure, T., Gjini, E., Stevens, J., Lane, W. J., Javeri, I., Nellaiappan, K., Salazar, A. M., Daley, H., Seaman, M., Buchbinder, E. I., Yoon, C. H., Harden, M., Lennon, N., Gabriel, S., Rodig, S. J., Barouch, D. H., Aster, J. C., Getz, G., Wucherpfennig, K., Neuberg, D., Ritz, J., Lander, E. S., Fritsch, E. F., Hacohen, N., & Wu, C. J. (2017, Jul. 13). An immunogenic personal neoantigen vaccine for patients with melanoma. *Nature*, 547 (7662), 217-221.
18. Riaz, N., Morris, L., Havel, J. J., Makarov, V., Desrichard, A., & Chan, T. A. (2016, August). The role of neoantigens in response to immune checkpoint blockade. *Int Immunol*, 28(8), 411-419.
19. Sahin, U., Derhovanessian, E., Miller, M., Kloke, B. P., Simon, P., Lower, M., Bukur, V., Tadmor, A. D., Luxemburger, U., Schrors, B., Omokoko, T., Vormehr, M., Albrecht, C., Paruzynski, A., Kuhn, A. N., Buck, J., Heesch, S., Schreeb, K. H., Muller, F., Ortseifer, I., Vogler, I., Godehardt, E., Attig, S., Rae, R., Breitkreuz, A., Tolliver, C., Suchan, M., Martic, G., Hohberger, A., Sorn, P., Diekmann, J., Ciesla, J., Waksmann, O., Bruck, A. K., Witt, M., Zillgen, M., Rothermel, A., Kasemann, B., Langer, D., Bolte, S., Diken, M., Kreiter, S., Nemecek, R., Gebhardt, C., Grabbe, S., Holler, C., Utikal, J., Huber, C., Loquai, C., & Tureci, O. (2017, Jul. 13). Personalized RNA mutanome vaccines mobilize poly-specific therapeutic immunity against cancer. *Nature*, 547(7662), 222-226.
20. Sarkizova, S., Klaeger, S., Le, P. M., Li, L. W., Oliveira, G., Keshishian, H., Hartigan, C. R., Zhang, W., Braun, D. A., Ligon, K. L., Bachireddy, P., Zervantonakis, I. K., Rosenbluth, J. M., Ouspenskaia, T., Law, T., Justesen, S., Stevens, J., Lane, W. J., Eisenhaure, T., Lan Zhang, G., Clauser, K. R., Hacohen, N., Carr, S. A., Wu, C. J., & Keskin, D. B. (2020, February). A large peptidome dataset improves HLA class I epitope prediction across most of the human population. *Nat Biotechnol,* 38(2), 199-209.
21. Savage, P., Stebbing, J., Bower, M., & Crook, T. (2009, January). Why does cytotoxic chemotherapy cure only some cancers? *Nat Clin Pract Oncol,* 6(1), 43-52.
22. Sawyers, C. (2004, Nov. 18). Targeted cancer therapy. *Nature,* 432(7015), 294-297.
23. Scaltriti, M., & Baselga, J. (2006, Sep. 15). The epidermal growth factor receptor pathway: a model for targeted therapy. *Clin Cancer Res,* 12(18), 5268-5272.
24. Schumacher, T. N., & Schreiber, R. D. (2015, Apr. 3). Neoantigens in cancer immunotherapy. *Science,* 348 (6230), 69-74.
25. Sharkey, R. M., & Goldenberg, D. M. (2006, July-August). Targeted therapy of cancer: new prospects for antibodies and immunoconjugates. *CA Cancer J Clin,* 56(4), 226-243.
26. Vogelstein, B., Papadopoulos, N., Velculescu, V. E., Zhou, S., Diaz, L. A., Jr., & Kinzler, K. W. (2013, Mar. 29). Cancer genome landscapes. *Science,* 339(6127), 1546-1558.
27. Wang, Q., Douglass, J., Hwang, M. S., Hsiue, E. H., Mog, B. J., Zhang, M., Papadopoulos, N., Kinzler, K. W., Zhou, S., & Vogelstein, B. (2019, November). Direct Detection and Quantification of Neoantigens. *Cancer Immunol Res,* 7(11), 1748-1754.
28. Wang, Q., Wang, X., Tang, P. S., O'Leary G, M., & Zhang, M. (2017, Jun. 13). Targeted sequencing of both DNA strands barcoded and captured individually by RNA probes to identify genome-wide ultra-rare mutations. *Sci Rep,* 7(1), 3356.
29. Yagoda, A., & Petrylak, D. (1993, Feb. 1). Cytotoxic chemotherapy for advanced hormone-resistant prostate cancer. *Cancer,* 71(3 Suppl), 1098-1109.
30. Zubarev, R. A., & Makarov, A. (2013, Jun. 4). Orbitrap mass spectrometry. *Anal Chem,* 85(11), 5288-5296.

The invention claimed is:

1. A method for characterization of a target peptide the method comprising:
   (1) mixing at least one guard peptide with the target peptide, wherein the at least one guard peptide has a different amino acid composition and sequence from the target peptide
   (2) subjecting the at least one guard peptide and the target peptide to liquid chromatography, wherein the at least one guard peptide blocks nonspecific binding of the target peptide to any surface or any substance; and
   (3) detecting the target peptide by mass spectrometry analysis, wherein each of the at least one guard peptide is configured to have an m/z value that is distinguishable from the target peptide by the mass spectrometry analysis,
   and wherein the target peptide comprises one of the following neoantigen peptides: KRAS Q61H, KRASQ61L, KRAS Q61R, IDH2 R140Q, TP53 Y220C, TP53 R248W, TP53 R213L, KRAS G12V 9mer, KRAS G12V 10mer, KRAS G12D 9mer, or KRAS G12D 10mer.

2. The method of claim 1, wherein: at least one amino acid residue in the guard peptide is a heavy isotope-labeled amino acid.

3. The method of claim 1, wherein only one amino acid residue in the guard peptide differs from the target peptide.

4. The method of claim 1, wherein at least two amino acid residues in the guard peptide differ from the target peptide.

5. The method of claim 1, wherein the guard peptide has a scrambled sequence compared with the target peptide.

6. The method of claim 1, wherein the neoantigen peptide is from a tissue sample obtained from a subject, the method further comprising a tissue sample preparation step prior to step (1), wherein the tissue preparation step comprises: providing the tissue sample, wherein the tissue sample is a frozen tissue sample; grinding the frozen tissue sample, under an impact force of at least 8,000 psi, to thereby obtain a frozen single-cell tissue powder; and treating the frozen single-cell tissue powder to provide a treated tissue sample.

7. The method of claim 6, wherein: in the providing the tissue sample of the tissue preparation step, the tissue sample is snap-frozen in liquid nitrogen; and in the grinding the frozen tissue sample, the impact force is approximately 10,000 psi, approximately 12,000 psi, or approximately 15,000 psi.

8. The method of claim 6, wherein the treating the frozen single-cell tissue powder comprises: lysis, sonication, and centrifugation, wherein the treated tissue sample is from a supernatant after the centrifugation.

9. The method of claim 8, further comprising:
performing an analysis over genomic DNA obtained from a pellet after the centrifugation.

10. The method of claim 6, further comprising a human leukocyte antigen (HLA) molecules enrichment step after the tissue sample preparation step and prior to step (1), wherein the HLA molecules enrichment step comprises:
passing the treated tissue sample through an HLA enrichment column, wherein the HLA enrichment column comprises a matrix with anti-HLA antibodies immobilized thereon.

11. The method of claim 10, after the HLA molecules enrichment step, the mixing of the at least one guard peptide with the target peptide of step (1) further comprises an elution step comprising applying an elution buffer having a low pH to the HLA enrichment column to thereby obtain an eluate containing the neoantigen peptide, wherein the elution buffer comprises the at least one guard peptide.

12. The method of claim 11, further comprising a clean-up step after the elution step and prior to step (2), wherein the clean-up step comprises:
passing the eluate through a trap column for at least one time to thereby trap the neoantigen peptide therewithin, wherein the trap column comprises a matrix capable of binding with the neoantigen peptide but having a lower or no binding affinity to impurities; and
eluting the trap column to thereby obtain a cleaned eluate.

13. The method of claim 12, wherein step (2) comprises: passing the cleaned eluate through a size exclusion column (SEC) for collecting a neoantigen peptide-containing fraction.

14. The method of claim 13, wherein at least two consecutive steps of the HLA molecules enrichment step, the elution step, the clean-up step, and step (2) are automatic.

15. The method of claim 14, wherein all steps of the HLA molecules enrichment step, the elution step, the clean-up step, and step (2) are automatic.

* * * * *